US010928321B2

(12) United States Patent
Rawle

(10) Patent No.: US 10,928,321 B2
(45) Date of Patent: Feb. 23, 2021

(54) PORTABLE DEVICE FOR DETECTING MOLECULE(S)

(71) Applicant: UBIQUITOME LIMITED, Auckland (NZ)

(72) Inventor: Christopher Bruce Rawle, Dunedin (NZ)

(73) Assignee: Ubiquitome Limited

( * ) Notice: Subject to any disclaimer, the term of this patent is extended or adjusted under 35 U.S.C. 154(b) by 0 days.

(21) Appl. No.: 14/383,468

(22) PCT Filed: Mar. 8, 2013

(86) PCT No.: PCT/NZ2013/000033
§ 371 (c)(1),
(2) Date: Sep. 5, 2014

(87) PCT Pub. No.: WO2013/133725
PCT Pub. Date: Sep. 12, 2013

(65) Prior Publication Data
US 2015/0111287 A1 Apr. 23, 2015

Related U.S. Application Data

(60) Provisional application No. 61/608,786, filed on Mar. 9, 2012.

(51) Int. Cl.
*G01N 21/64* (2006.01)
*B01L 7/00* (2006.01)
(Continued)

(52) U.S. Cl.
CPC ............ *G01N 21/6452* (2013.01); *B01L 7/52* (2013.01); *B01L 9/06* (2013.01); *C12Q 1/686* (2013.01);
(Continued)

(58) Field of Classification Search
None
See application file for complete search history.

(56) References Cited

U.S. PATENT DOCUMENTS 2,267,948 A 12/1941 Rantsch
4,713,219 A 12/1987 Gerken et al.
(Continued)

FOREIGN PATENT DOCUMENTS

CA 2005622 A1 6/1991
DE 102004039564 A1 2/2006
(Continued)

OTHER PUBLICATIONS

Donaldson et al., "Detection, quantitation and identification of enteroviruses from surface waters and sponge tissue from the Florida Keys using real-time RT-PCR" Water Res. 36: 2505-2514, 2002.
(Continued)

*Primary Examiner* — Edwin C Gunberg
(74) *Attorney, Agent, or Firm* — Morriss O'Bryant; Compagni Cannon, PLLC.

(57) ABSTRACT

An optical assembly 140 for a portable device for detecting molecule(s) within reaction vessels 110 comprises a collimator 403, a beam splitter arrangement and a plurality of guide arrangements 143. The collimator 403 collimates an excitation beam from an excitation source 400. The beam splitter arrangement splits the excitation beam from the collimator into a plurality of split excitation beams. Each beam splitter splits an incoming beam into two beams. In the case where the beam splitter arrangement comprises more than one beam splitter, the beam splitters are arranged in tiers such that a first tier comprises one beam splitter for receiving the excitation beam from the collimator, and each of the other tiers comprises one or more beam splitters. Each beam splitter in at least one of the other tiers receives a split
(Continued)

excitation beam from a previous tier. Each guide arrangement 140 guides a respective one of the plurality of split excitation beams along an excitation path A from the beam splitter arrangement into a reaction vessel 110 containing a sample to stimulate an emission of a reaction light from the sample. Each guide arrangement 140 further guides reaction light from the sample along a detection path B towards a detector arrangement 142.

19 Claims, 36 Drawing Sheets

Specification includes a Sequence Listing.

(51) Int. Cl.
| | | |
|---|---|---|
| *B01L 9/06* | (2006.01) | |
| *C12Q 1/686* | (2018.01) | |
| *C12Q 1/689* | (2018.01) | |
| *C12Q 1/70* | (2006.01) | |
| *G02B 27/14* | (2006.01) | |
| *G01N 21/15* | (2006.01) | |
| *G01N 21/03* | (2006.01) | |

(52) U.S. Cl.
CPC .............. *C12Q 1/689* (2013.01); *C12Q 1/701* (2013.01); *G01N 21/6486* (2013.01); *B01L 2300/0654* (2013.01); *G01N 21/0332* (2013.01); *G01N 2021/158* (2013.01); *G01N 2021/6419* (2013.01); *G01N 2021/6421* (2013.01); *G01N 2021/6463* (2013.01); *G01N 2201/0221* (2013.01); *G01N 2201/068* (2013.01); *G01N 2201/0612* (2013.01); *G02B 27/146* (2013.01)

(56) References Cited

U.S. PATENT DOCUMENTS

| | | | |
|---|---|---|---|
| 4,988,630 A | 1/1991 | Chen et al. | |
| 5,270,011 A | 12/1993 | Altherr | |
| 5,567,617 A | 10/1996 | Caprio et al. | |
| 5,861,124 A | 1/1999 | Hosoi et al. | |
| 5,994,056 A | 11/1999 | Higuchi | |
| 6,084,717 A | 7/2000 | Wood et al. | |
| 6,407,395 B1 | 6/2002 | Perov et al. | |
| 6,603,546 B1 | 8/2003 | Barbieri et al. | |
| 6,814,934 B1 | 11/2004 | Higuchi | |
| 6,844,185 B2* | 1/2005 | Tashiro ................ | C12Q 1/6816 250/553 |
| 6,992,748 B2* | 1/2006 | Koh .................... | G02F 1/13471 349/196 |
| 7,961,314 B2 | 6/2011 | Lundquist et al. | |
| 2001/0012612 A1* | 8/2001 | Petersen ................ | B01L 3/502 435/5 |
| 2002/0150933 A1 | 10/2002 | Ehricht et al. | |
| 2002/0197636 A1 | 12/2002 | Emoto | |
| 2003/0160957 A1 | 8/2003 | Oldham et al. | |
| 2004/0149725 A1 | 8/2004 | Brown | |
| 2005/0145273 A1 | 7/2005 | Atwood et al. | |
| 2006/0131596 A1 | 6/2006 | Ouderkirk et al. | |
| 2007/0065074 A1* | 3/2007 | Hillendahl ......... | G01N 21/6452 385/33 |
| 2009/0269835 A1 | 10/2009 | Ceremony et al. | |
| 2009/0283512 A1 | 11/2009 | Huhn et al. | |
| 2010/0124766 A1 | 5/2010 | Ng et al. | |
| 2011/0152108 A1 | 6/2011 | Brenan et al. | |
| 2012/0279954 A1 | 11/2012 | Ceremony et al. | |
| 2012/0295249 A1 | 11/2012 | Cherubini et al. | |
| 2013/0330247 A1 | 12/2013 | Wilson et al. | |
| 2016/0051982 A1 | 2/2016 | Rawle | |

FOREIGN PATENT DOCUMENTS

| | | |
|---|---|---|
| EP | 2498089 A2 | 9/2012 |
| JP | 2003329580 A | 11/2003 |
| JP | 2009118798 A | 6/2009 |
| JP | 2012024000 A | 2/2012 |
| WO | WO 2004/031342 A1 | 4/2004 |
| WO | WO-2008030914 A2 | 3/2008 |
| WO | WO 2011/086498 A2 | 7/2011 |
| WO | WO-2011124918 A1 | 10/2011 |
| WO | WO 2012/012779 A2 | 1/2012 |
| WO | WO 2013/133725 A1 | 9/2013 |

OTHER PUBLICATIONS

Heim et al., "Rapid and quantitative detection of human adenovirus DNA by real-time PCR" J. Med. Virology 70:228-239, 2003.
Kageyama et al., "Broadly reactive and highly sensitive assay for Norwalk-like viruses based on real-time quantitative reverse transcription-PCR" J. Clin. Microbiol. 41:1548-1557, 2003.
Le Cann et al., "Quantification of human astroviruses in sewage using real-time RT-PCR", Res. Microbiol. 155:11-15, 2004.
PCT/NZ2013/000033 International Search Report and Written Opinion dated Jul. 18, 2013.
PCT/NZ2014/000028 International Search Report and Written Opinion dated May 9, 2014.
Shu et al., "Design and performance of the CDC real-time reverse transcriptase PCR swine flu panel for detection of 2009 A (H1N1) pandemic influenza virus" J. Clin. Microbiol. 49:2614-2619, 2011.
Thomas et al., "Tracking verocytotoxigenic *Escherichia coli* O157, O26, O111, O103 and O145 in Irish cattle", Int. J. Food Microbiol. 153: 288-296, 2012.
European Application No. 13757679 Supplementary Partial European Search Report dated Oct. 2, 2015.
European Application No. 13757679.9 Extended European Search Report dated Mar. 3, 2016.
European Application No. 14760298.1 Partial European Search Report dated Apr. 11, 2016.
European Application No. 14760298.1 Extended European Search Report dated Aug. 24, 2016.
U.S. Appl. No. 14/773,077 Non-Final Office Action dated Sep. 7, 2016.
Benz, Klaus-Werner, et al. Introduction to Crystal Growth and Characterization with a contribution by Anna Mogilatenko, Wiley-VCH, published online on Aug. 1, 2014, pp. 1-9.
NPL Nation Physical laboratory, Kaye & Laby tables of physical and chemical constants, 2.3.6 specific heat capacities, pp. 1 -6, 2017.
U.S. Appl. No. 14/773,077 Final Office Action dated Aug. 30, 2017.

\* cited by examiner

Wild type 1:1

GFP 1:1

Wild type 1:16

GFP 1:16

PORTABLE DEVICE FOR DETECTING MOLECULE(S)

RELATED APPLICATIONS

This application is filed pursuant to 35 U.S.C. § 371 as a United States National Phase Application of International Application No. PCT/NZ2013/000033, entitled "PORTABLE DEVICE FOR DETECTING MOLECULE(S)" filed on Mar. 8, 2013, which claims the benefit of U.S. Provisional Application No. 61/608,786, filed Mar. 9, 2012, each of which are incorporated herein by reference in their entirety.

The instant application contains a Sequence Listing which has been submitted in ASCII format via EFS-Web and is hereby incorporated by reference in its entirety. Said ASCII copy, created on Jan. 13, 2015 is named 47138-701-831-SL.txt and is 4 Kilobytes in size.

FIELD OF THE INVENTION

The present invention relates to a portable device for detecting molecule(s). In preferred embodiments, the device may be used for one or more of: amplification and detection of nucleic acids including analysis of polymerase chain reactions (such as quantitative polymerase chain reactions), protein analysis, ligand analysis, or fluorescence analysis of any chemical reactions, for example.

BACKGROUND

Systems and methods for detecting molecule(s) are widely known and used.

Amplification of nucleic acids can be performed using quantitative polymerase chain reaction (Q-PCR) analysis for example. Generally for a Q-PCR analysis, the temperature of a sample within a reaction vessel is repeatedly cycled between a higher temperature at which the template DNA is denatured, and a lower temperature at which the primers in the sample anneal to a targeted DNA sequence and the DNA replicates. This thermal cycling is commonly repeated up to 40 times until the DNA in the sample is amplified or replicated sufficiently to enable detection of a fluorescing reagent dye bound to the DNA.

Proteins within a sample can be detected through antibody binding approaches for example. Fluorescently labelled antibodies can be mixed with a sample and the protein-antibody complexes captured. Presence of florescence indicates the presence of the protein in the sample.

Detection of metabolites can be performed for example. For this use a sample is mixed with a reporter dye. The metabolite in the sample either directly or indirectly converts the reporter to a fluorescent dye in proportion to the amount of metabolite in the original sample.

The Q-PCR method is described generally in U.S. Pat. No. 5,994,056 to Russell Higuchi entitled "Homogenous methods for nucleic acid amplification and detection", for example. This document discloses a method for detecting amplification by exposing the reaction mixture to ultraviolet light and detecting fluorescence of ethidium bromide fluorescent dye using a spectra fluorometer.

Various apparatuses for performing Q-PCR analysis, protein analysis, or ligand analysis are commercially available and used in laboratories by skilled and trained users to amplify and quantify a targeted molecule.

Such apparatuses generally include some form of thermal block adapted to receive at least one reaction vessel containing a reaction mixture including the sample, heating/cooling means thermally coupled to the thermal block, excitation means for exciting the reaction mixture, and detection means for optically detecting fluorescence of a reagent dye bound to target in the reaction mixture, in response to the excitation.

Each reaction vessel is generally sealed/covered by a substantially transparent cover to prevent the sample within the reaction vessel from escaping the reaction vessel during the amplification processes while still allowing excitation radiation from an excitation source to enter into the reaction vessel and allowing a fluorescence from the reaction vessel to be detected. During the heating and cooling processes, the sample within the reaction vessel evaporates and condenses on the cover of the reaction vessel. The evaporation and condensation of the sample mixture on the cover of the reaction vessel interferes with the optical path of the radiation beam into the reaction vessel and of the fluorescence from the sample within the reaction vessel. The condensation also starves the chemical reaction of its components changing the fidelity of the assay. The optical interference and changes to assay performance reduces the accuracy of the detection.

Existing apparatuses for detection of molecules are generally designed exclusively for use in a laboratory environment, and may be adapted to thermally cycle a large array of samples (for example, in 96 or more reaction vessels or wells as in a microtiter plate) at the same time. As a result, these apparatuses are generally relatively large, heavy, and inefficient in terms of power use, in particular when analysing only a small number of samples. These apparatuses are also commonly expensive and/or complex.

An example of such an apparatus is described in U.S. Pat. No. 6,814,934 to Russell Higuchi, entitled "Instrument for monitoring nucleic acid amplification". This document discloses a detection system comprising a thermal cycler and an independently-housed spectra fluorometer, whereby the fluorometer is optically coupled with the reaction vessels by way of fibre optic cables. Although integration of the thermal cycler and fluorometer is suggested in this document, there is no detailed disclosure of an integrated apparatus, let alone an apparatus which is small, efficient, and portable.

There is a need for a suitable apparatus for detecting molecule(s) which is compact and portable, robust, efficient and/or relatively simple to operate. Such a portable apparatus has potential uses "in the field" (ie outside the laboratory environment) by semi-skilled users with limited or no training, for environmental testing for example.

It is an object of at least preferred embodiments of the present invention to provide a portable device for detecting molecule(s) that addresses the disadvantages of the existing devices, or to at least provide the public with a useful alternative.

SUMMARY OF THE INVENTION

In accordance with a first aspect of the present invention, there is provided an optical assembly for a portable device for detecting molecule(s) within reaction vessels, the optical assembly comprising:
 a collimator for collimating an excitation beam from an excitation source;
 a beam splitter arrangement having one or more beam splitters, the beam splitter arrangement being configured to split the excitation beam from the collimator into a plurality of split excitation beams, the or each beam splitter configured to split an incoming beam into two beams, wherein in the case where the beam splitter arrangement comprises more than one beam splitter, the beam splitters are arranged in tiers such that a first tier comprises one beam splitter for receiving the excitation beam from the collimator, and each of the other tiers comprises one or more beam splitters, each beam splitter in at least one of the other tiers being configured to receive a split excitation beam from a previous tier; and a plurality of guide arrangements, each guide arrangement being configured to guide a respective one of the plurality of split excitation beams along an excitation path from the beam splitter arrangement into a reaction vessel containing a sample to stimulate an emission of a reaction light from the sample, and being further configured to guide reaction light from the sample along a detection path towards a detector.

The term 'comprising' as used in this specification and claims means 'consisting at least in part of'. When interpreting statements in this specification and claims which include the term 'comprising', other features besides the features prefaced by this term in each statement can also be present. Related terms such as 'comprise' and 'comprised' are to be interpreted in similar manner.

In an embodiment, the optical assembly further comprises an excitation source for transmitting the excitation beam. In a further embodiment, the excitation source is a laser diode. Alternatively, the excitation source may be a light-emitting diode (LED). In a further embodiment, the collimator is part of the excitation source. In an alternative embodiment, the collimator is separate from the excitation source. In a further embodiment, the optical assembly comprises a plurality of excitation sources, each excitation source for transmitting an excitation beam at a different wavelength from the other excitation sources, wherein the excitation beams from the excitation sources are combined to form the excitation beam for the beam splitter arrangement. In a further embodiment, the excitation beams are combined to form the excitation beam for the beam splitter arrangement using beam combination optics.

In an embodiment, the excitation beam has a wavelength of between about 346 nm and about 784 nm. In a further embodiment, the excitation beam has a wavelength of between about 460 nm and about 480 nm. In a further embodiment, the wavelength of the excitation beam is about 470 nm. Alternatively, the wavelength of the excitation beam may be about 473 nm. In an alternative embodiment, where the optical assembly comprises a plurality of excitation sources, the excitation beam comprises two or more wavelengths. In a further embodiment, the excitation beam comprises a red wavelength and a blue wavelength, or a green wavelength and a blue wavelength, or a green wavelength and a red wavelength. In a further embodiment, the excitation beam comprises red, green and blue wavelengths. In a further embodiment, the excitation beam has a substantially narrow band of about 1 nm at a wavelength of about 470 nm. In a further embodiment, the excitation beam from the excitation source has a power of at least about 0.01 mW per reaction vessel. In a further embodiment, the excitation beam from the excitation source has a power of at least about 0.05 mW per reaction vessel. In a further embodiment, the excitation beam from the excitation source has a power of at least about 1 mW for a four channel device.

In an embodiment, the collimator comprises a collimating lens. In a further embodiment, the collimating lens has a focal point of between about 4 mm and about 12 mm. In an embodiment, the collimating lens has a focal point of about 8 mm.

In an embodiment, the optical assembly further comprises an attenuator for reducing the power of the excitation beam from the collimator. In a further embodiment, the attenuator comprises a neutral density (ND) filter. In a further embodiment, the attenuator reduces the power of the excitation beam by a factor of about 10. In a further embodiment, the attenuator is positioned between the collimator and the beam splitter arrangement. In a further embodiment, about 10 mW is incident on the ND filter, and about 1 mW exits the ND filter to the beam splitter arrangement. In an alternative embodiment, the optical assembly may comprise at least one attenuator for reducing the power of at least one of the plurality of split excitation beams from the beam splitter arrangement.

In an embodiment, the optical assembly further comprises a wavelength filter for filtering any spectral components in the excitation beam from the collimator that fall within a band of the reaction light from the sample in at least one of the reaction vessels. In a further embodiment, the wavelength filter comprises a laser diode clean-up filter. In a further embodiment, the wavelength filter is adapted to attenuate spectral components having a wavelength of about 500 nm to about 1000 nm in the excitation beam, to prevent interference of the excitation beam and the reaction light. In a further embodiment, the wavelength filter is positioned between the attenuator and the beam splitter arrangement. Alternatively, the wavelength filter may be positioned in between the collimating lens and the attenuator. In a further embodiment, the wavelength filter comprises a coloured glass arrangement. In a further embodiment, the wavelength filter comprises both coloured glass and interference element component(s). In an alternative embodiment, the optical assembly may comprise at least one wavelength filter, the or each wavelength filter for filtering spectral components in at least one of the plurality of split excitation beams from the beam splitter arrangement.

In an embodiment, the optical assembly further comprises an optical aperture for reducing a diameter of the excitation beam from the collimator. In a further embodiment, the optical aperture is provided by a component made of black acetyl. In a further embodiment, the optical aperture is configured to reduce the diameter of the excitation beam to about 3 mm. In a further embodiment, the optical aperture is positioned between the wavelength filter or the attenuator and the beam splitter arrangement. Alternatively, the optical aperture may be positioned between the collimator and attenuator or the wavelength filter. In a further embodiment, the optical aperture is positioned after the collimator and before the first beam splitter element. In an alternative embodiment, the optical assembly may comprise at least one optical aperture, the or each aperture for reducing the diameter of at least one of the plurality of split excitation beams from the beam splitter arrangement.

In an embodiment, at least one beam splitter of said one or more beam splitters is a cube beam splitter that is configured to receive a single beam, and to split the single beam into two split beams, each split beam having substantially the same or different intensities. Alternatively, at least one beam splitter of said one or more beam splitters may be a plate beam splitter that is configured to receive one beam or a plurality of spaced apart beams, and to split the or each beam into two split beams, each split beam having substantially the same or different intensities. In a further embodiment, the beam splitter arrangement may comprise a combination of cube beam splitter(s) and plate beam splitter(s). In a further embodiment, the beam splitter arrangement comprises a plurality of beam splitters, and each beam splitter comprises a cube beam splitter. In a further embodiment, the beam splitter arrangement comprises up to about ten beam splitters. In a further embodiment, two or more beam splitters of the beam splitter arrangement are together a monolithic optical component.

In an embodiment, the beam splitter arrangement comprises $2^n-1$ number of beam splitters configured to split the excitation beam from the collimator into $2^n$ number of split excitation beams of substantially equal intensity and wavelength, n being an integer greater than zero, the or each beam splitter being configured to split an incoming beam into two beams, wherein in the case where n is more than one, the beam splitters are arranged in n number of tiers such that a first tier contains one beam splitter for receiving the excitation beam from the collimator and an $i^{th}$ tier contains $2^{i-1}$ beam splitters, i being an integer ranging from 2 up to n, where the or each respective beam splitter in a tier is associated with two respective beam splitters in a next tier such that two beams split by a respective beam splitter in a tier are split further into four beams by the associated beam splitters in the next tier.

In an embodiment, the beam splitter arrangement is configured to split the excitation beam from the collimator into up to k number of split excitation beams, k being an even integer greater than two, wherein the beam splitters are arranged in m number of tiers, where m is an integer greater than 1 and $k=2\times m$, such that a first tier contains one beam splitter that is configured to receive the excitation beam from the collimator, and to split the incoming beam into two split excitation beams, an $i^{th}$ tier, i being an integer ranging from 2 to m, is configured to receive incoming beams from a previous tier and to split each incoming beam into two split excitation beams, wherein in the case where i is less than m, one of the split excitation beams is directed to the next tier and the other split excitation beam is one of the k split excitation beams, and in the case where i equals m, the $m^{th}$ tier is each split excitation beams from the $m^{th}$ tier is one of the k split excitation beams.

In an embodiment, the $i^{th}$ tier is configured to split each incoming beam into two split excitation beams having a beam intensity of about $$\frac{100}{m-(i-2)}\%$$

and about $$100\left(1-\frac{1}{m-(i-2)}\right)\%$$

respectively, wherein the split excitation beam with the higher intensity is directed to the next tier and the split excitation beam with the lower intensity is one of the k split excitation beams, and each split excitation beams from the $m^{th}$ tier is one of the k split excitation beams, wherein the k split excitation beams have substantially equal intensity and wavelength.

In an embodiment, the beam splitter arrangement is configured to split the excitation beam from the collimator into up to k number of split excitation beams, k being an even integer greater than two, wherein the beam splitters are arranged in (m+n) number of tiers, where m and n are integers indicating the number of primary tiers and secondary tiers respectively, m being greater than one and n being greater than zero, and $k=2\times m\times(n+1)$, such that the first tier, which is one of the primary tiers, contains one beam splitter that is configured to receive the excitation beam from the collimator, and to split the incoming beam into two split excitation beams, an $i^{th}$ tier, which is one of the primary tiers, i being an integer ranging from 2 to m, is configured to receive incoming beams from a previous tier and to split each incoming beam into two split excitation beams, wherein in the case where i is less than m, one of the split excitation beams is directed to the next tier and the other split excitation beam is directed to the $(m+1)^{th}$ tier, and in the case where i equals m, the split excitation beams from the $m^{th}$ tier are directed to the $(m+1)^{th}$ tier of the secondary tiers, a $j^{th}$ tier, which is one of the secondary tiers, j being an integer ranging from m+1 to m+n, is configured to receive incoming beams from a previous tier and to split each incoming beam into two split excitation beams, wherein in the case where j is less than n, one of the split excitation beams is directed to the next tier and the other split excitation beam is one of the k split excitation beams, and in the case where j equals m+n, each split excitation beam from the $(m+n)^{th}$ tier is one of the k split excitation beams.

In an embodiment, the $i^{th}$ tier is configured to split each incoming beam into two split excitation beams having a beam intensity of about $$\frac{100}{m-(i-2)}\%$$

and about $$100\left(1-\frac{1}{m-(i-2)}\right)\%$$

respectively, wherein the split excitation beam with the higher intensity is directed to the next tier and the split excitation beam with the lower intensity is directed to the $(m+1)^{th}$ tier, and the split excitation beams from the $m^{th}$ tier are directed to the $(m+1)^{th}$ tier. In a further embodiment, the $j^{th}$ tier is configured to split each incoming beam into two split excitation beams having a beam intensity of about $$\frac{100}{(m+n)-(j-2)}\%$$

and about $$100\left(1-\frac{1}{(m+n)-(j-2)}\right)\%$$

respectively, wherein the split excitation beam with the higher intensity is directed to the next tier and the split excitation beam with the lower intensity is one of the k split excitation beams, and each split excitation beam from the m+n$^{th}$ tier is one of the k split excitation beams, wherein the k number of excitation beams have substantially equal intensity and wavelength.

In an embodiment, the beam splitter arrangement comprises a polarising cube beam splitter and a half-wave plate associated with the polarising cube beam splitter, the polarising cube beam splitter and half-wave plate being arranged such that an excitation beam passes through the half-wave plate before being split by the polarising cube beam splitter. In a further embodiment, at least the cube beam splitter in the first tier of the beam splitter arrangement is a polarising cube beam splitter having an associated half-wave plate. In a further embodiment, the beam splitter arrangement comprises a non-polarising cube beam splitter. In a further embodiment, where there is more than one tier, the beam splitter arrangement comprises a combination of at least one half-wave plate, at least one polarising cube beam splitter, and at least one non-polarising cube beam splitter. In a further embodiment, there is more than one tier, the cube beam splitter in the first tier comprises a half-wave plate and an associated polarising cube beam splitter, and the cube beam splitters in the other tiers are non-polarising cube beam splitters. Alternatively, where there is more than one tier, the beam splitter arrangement may comprise at least two polarising cube beam splitters, each beam splitter having an associated half-wave plate. In a further embodiment, all cube beam splitters in the beam splitter arrangement are non-polarising cube beam splitters. In that embodiment, one or more linear polarisers may be provided to discard excess excitation light. In an alternative embodiment, the beam splitter arrangement may comprise a polarising beam splitter without an associated half-wave plate. In that embodiment, the polarising beam splitter may be rotated to produce two split excitation beams of substantially equal intensities.

In an embodiment, the beam splitter arrangement of the device for detecting molecule(s) in two reaction vessels comprises one beam splitter for splitting the excitation beam into two split excitation beams of substantially equal intensity and wavelength, each split excitation beam for a respective one of the reaction vessels. In a further embodiment, the beam splitter is a polarising cube beam splitter having associated therewith a half-wave plate configured to rotate a polarisation of the excitation beam from the excitation source. Alternatively, the beam splitter may be a non-polarising cube beam splitter.

In an embodiment, the beam splitter arrangement of the device detecting molecule(s) in four reaction vessels has two tiers. In a further embodiment, a first tier is configured to receive the excitation beam from the collimator and to split that beam into two split excitation beams and a second tier is configured to receive the split excitation beams from the first tier and to split those beams into four split excitation beams. In a further embodiment, the first tier comprises a half-wave plate and a polarising cube beam splitter. In a further embodiment, the second tier comprises two non-polarising cube beam splitters. In a further embodiment, the half-wave plate is configured to rotate a polarisation of the excitation beam from the excitation source before the excitation beam is split by the polarising cube beam splitter in the first tier into two split components. In a further embodiment, each of the non-polarising cube beam splitters in the second tier is configured to split the split component from the polarising cube beam splitter in the first tier into two further split components. In a further embodiment, the beam splitter arrangement is configured to output four split excitation beams of substantially equal intensity and wavelength, each split excitation beam for a respective one of the reaction vessels. In a further embodiment, the guide arrangements are configured to guide the beams into four reaction vessels. The reaction vessels may be separately or integrally formed.

In an embodiment, the beam splitter arrangement of the device for detecting molecule(s) in six reaction vessels has three tiers, such that
 a first tier is configured to receive the excitation beam from the collimator and to split the excitation beam from the collimator into two beams of substantially equal intensities,
 a second tier is configured to receive two incoming beams from the first tier and to split each incoming beam into a split excitation beam of about 33% intensity and a split excitation beam of about 67% intensity,
 a third tier is configured to receive the two split excitation beams of about 67% intensity from the second tier and to split each incoming beam into two split excitation beams of substantially equal intensities,
wherein the six split excitation beams of substantially equal intensity and wavelength comprise the split excitation beams of about 33% intensity from the second tier and the split excitation beams from the third tier. In a further embodiment, the guide arrangement is configured to guide the beams into six reaction vessels. The reaction vessels may be separately or integrally formed.

In a embodiment, the beam splitter arrangement of the device for detecting molecule(s) in eighteen reaction vessels has five tiers, three of which are primary tiers and two which are secondary tiers, such that
 a first tier is configured to receive the excitation beam from the collimator and to split the excitation beam from the collimator into two beams of substantially equal intensities,
 a second tier is configured to receive two incoming beams from the first tier and to split each incoming beam into a split excitation beam of about 33% intensity and a split excitation beam of about 67% intensity,
 a third tier is configured to receive the two split excitation beams of about 67% intensity from the second tier and to split each incoming beam into two split excitation beams of substantially equal intensities,
 a fourth tier of the secondary tiers is configured to receive the two 33% intensity split excitation beams from the second tier and four split excitation beams from the third tier and to split each incoming beam into a split excitation beam of about 33% intensity and a split excitation beam of about 67% intensity, and
 a fifth tier is configured to receive the six split excitation beams of about 67% intensity from the fourth tier and to split each incoming beam into two split excitation beams of substantially equal intensities,
wherein the eighteen split excitation beams of substantially equal intensity and wavelength comprise six split excitation beams of about 33% intensity from the fourth tier and twelve split excitation beams from the fifth tier. In a further embodiment, the guide arrangement is configured to guide the beams into eighteen reaction vessels. In a further embodiment, the reaction vessels may be separately or integrally formed. In a further embodiment, the first, second, third, fourth and fifth tiers comprise cube beam splitters. In an alternative embodiment, the first, second, third, fourth and fifth tiers comprise plate beam splitters. In a preferred embodiment, the first, second, third, fourth and fifth tiers comprise a combination of cube beam splitters and plate beam splitters. In a further embodiment, the first, second and third tier comprise cube beam splitters, and the fourth and fifth tiers each comprises a plate beam splitter.

In an embodiment, the beam splitter arrangement comprises a beam steering device for allowing the tiers to be positioned in a desired arrangement relative to each other and/or for allowing beam splitters within a tier to be positioned in a desired arrangement relative to each other. In a further embodiment, the beam steering device comprises a mirror that is substantially about 100% optically reflective.

In an embodiment, the optical assembly comprises a linear polariser. Preferably, the linear polariser trims the laser power (via polariser rotation) from the beam splitter arrangement such that each laser channel is then of substantially equal power. Preferably, the linear polariser is positioned between the beam splitter arrangement and the guide arrangement. In a further embodiment, the device is for detecting molecule(s) in two reaction vessels and comprises two linear polarisers, each linear polariser being arranged to receive a respective one of the excitation split beams from the beam splitter arrangement. Alternatively, the device may be for detecting molecule(s) in four reaction vessels and comprises four linear polarisers, each linear polariser being arranged to receive a respective one of the excitation split beams from the beam splitter arrangement.

In an embodiment, each guide arrangement may comprise at least one common element for guiding a split excitation beam from the beam splitter arrangement to the reaction vessel and for guiding the reaction light from the reaction vessel to the detector. In a further embodiment, each guide arrangement comprises a dichroic element. In a further embodiment, the excitation path from each guide arrangement to the respective reaction vessel is substantially collinear or parallel with the detection path from the respective reaction vessel to the guide arrangement. In a further embodiment, the dichroic element is oriented at an angle of about 45° with respect to the excitation path of a split excitation beam from the beam splitter arrangement and at an angle of about 45° with respect to the detection path of the reaction light from the reaction vessel. In a further embodiment, the dichroic element is substantially reflective for wavelengths of the excitation beam and substantially transmissive for wavelengths of the reaction light. In a further embodiment, the dichroic element is configured to fold the excitation path from the beam splitter arrangement toward the respective reaction vessel by an angle of about 90°. Alternatively, the dichroic element may be substantially transmissive for wavelengths of the excitation beam from the arrangement of beam splitters and substantially reflective for wavelengths of reaction light. In a further embodiment, the dichroic element is configured to fold the detection path from the reaction vessel toward the respective detector by an angle of about 90°. In a further embodiment, the dichroic element is positioned after the linear polariser. In a further embodiment, the device is for detecting molecule(s) in two reaction vessels, and comprises two dichroic elements, each dichroic element being arranged to receive a respective one of the excitation split beams from the beam splitter arrangement. In a further embodiment, the device is for detecting molecule(s) in four reaction vessels, and comprises four dichroic elements, each dichroic element being arranged to receive a respective one of the excitation split beams from the beam splitter arrangement. In a further embodiment, the dichroic element of a guide arrangement is separate from the dichroic element of at least one other of the guide arrangements. In an alternative embodiment, the dichroic element of a guide arrangement may be common to at least one other of the guide arrangements. In a further embodiment, where a plurality of wavelengths of excitation beams are used or where the reaction light comprises multiple reaction light wavelengths, the dichroic element may be replaced by a multi-transition interference filter, such as a trichroic element, a notch filter, or a multi-bandpass filter for example.

In an embodiment, each guide arrangement may comprise an element for guiding a split excitation beam from the beam splitter arrangement to the reaction vessel and a separate element for guiding the reaction light from the reaction vessel to the detector. In a further embodiment, the guide arrangement comprises a first filter element and a second filter element positioned on or facing opposite sides of the reaction vessel, wherein the reaction vessel is substantially optically transparent, the first filter element being configured to guide a respective one of the split excitation beams along the excitation path from the beam splitter arrangement into the reaction vessel, and the second filter element being configured to guide reaction light from the sample along the detection path towards the detector. In a further embodiment, the first filter element is configured to pass the excitation beam from the beam splitter arrangement toward the reaction vessel and to reflect the reaction light from the reaction vessel. In a further embodiment, the second filter element is configured to pass the reaction light from the reaction vessel toward the detector and to attenuate or block the excitation beam. In a further embodiment, the first filter element and/or second filter element comprises a dichroic element. In a further embodiment, the first filter element and/or second filter element are integral with the reaction vessel or with a holder of the reaction vessel. In a further embodiment, the first filter element and second filter element of a guide arrangement is separate from the first filter element and second filter element of at least one other of the guide arrangements. In an alternative embodiment, the first filter element and/or second filter element of a guide arrangement may be common to at least one other of the guide arrangements. In a further embodiment, where a plurality of wavelengths of excitation beams are used or where the reaction light comprises multiple reaction light wavelengths, the dichroic element may be replaced by a multi-transition interference filter, such as a trichroic element, a notch filter, or a multi-bandpass filter for example.

In an embodiment, the optical assembly further comprises a focusing lens for imaging a respective one of the split excitation beams from the first guide into one of the reaction vessels and/or for imaging reaction light from the reaction vessel(s) to the detector. Preferably, the optical assembly further comprises a second collimator for collimating reaction light from the respective reaction vessel. Preferably, the second collimator is a collimating lens. Preferably, the focusing lens and the collimating lens form part of a single focusing/collimating lens. In a further embodiment, the device is for detecting molecule(s) in two reaction vessels, and comprises two focusing/collimating lenses, each lens being arranged to receive a respective one of the excitation split beams from the beam splitter arrangement. In a further embodiment, the device is for detecting molecule(s) in four reaction vessels, and comprises four focusing/collimating lenses, each lens being arranged to receive reaction light from the respective reaction vessel.

In an embodiment, the optical assembly further comprises detectors for receiving the reaction light from the reaction vessels. In a further embodiment the device is for detecting molecule(s) in two reaction vessels and comprises two detectors, each detector being associated with a respective one of the reaction vessels. In a further embodiment, the device is for detecting molecule(s) in four reaction vessels and comprises four detectors, each detector being associated with a respective one of the reaction vessels.

In an embodiment, the detector comprises a photodiode for generating an electrical signal proportional to the received reaction light. In a further embodiment, the photodiode is an avalanche photodiode.

In an embodiment, the detector further comprises a bandpass filter for passing a wavelength or range of wavelengths of the reaction light and attenuating other wavelengths. In a further embodiment, the bandpass filter is configured to pass wavelengths in the interval of about 442 nm to about 814 nm. In a further embodiment, the bandpass filter is configured to pass wavelengths in the interval from about 520 nm to about 560 nm in the reaction light. In a further embodiment, the bandpass filter is configured to pass a wavelength of Sybr Green fluorescence, or fluorescence from other similar green emitting flourophores such as FAM for example, from the sample. Any suitable bandpass filter could be used for passing a wavelength of the reaction light and attenuating all other wavelengths. By way of example only, any of the following fluorophores could be used, with a corresponding bandpass filter (dye—excitation in nm—emission in nm): SYBR—497-520; FAM—495-520; TET—521-536; JOE—520-548; VIC—538-554; HEX—535-556; R6G—524-557; Cy3—550-570; TAMRA—555-576; NED—546-575; Cy3.5-581-596; ROX—575-602; Texas Red—583-603; Cy5—649-670; Cy5.5—675-694. Alternatively, as another example, any of the Alexa Fluor dyes that cover a suitable portion of the spectrum could be used.

In an embodiment, the detector further comprises a glass filter for removing non-collimated light components from the reaction light. In a further embodiment, the glass filter attenuates wavelengths less than about 500 nm. The bandpass filter and glass filter suitably both block the same wavelengths. The glass filter suitably blocks off-axis light which can penetrate the bandpass filter (which is manufactured using dielectric coatings). Alternatively, the glass filter element could be incorporated into the bandpass filter.

In an embodiment, the detector further comprises an imaging lens for imaging the reaction light onto the photodiode. In a further embodiment, the imaging lens is an aspheric lens having a focal length of between about 8 mm and about 20 mm. In a further embodiment, the focal length is about 12 mm.

In an embodiment, where the guide arrangement is one dichroic element, the detectors and the beam splitter arrangement are positioned such that the excitation path of each split excitation beam from the beam splitter arrangement to the guide arrangement is substantially transverse to the detection path of the reaction light from the guide arrangement to the respective detectors. Preferably, each detector is positioned such that the detection path from the respective reaction vessel to the respective guide arrangement is substantially transverse to the detection path from the guide arrangement to the detector. Alternatively, the beam splitter arrangement may be positioned such that the excitation path from the beam splitter arrangement to the respective guide arrangement is substantially transverse to the excitation path from the guide arrangement to the respective reaction vessel.

In an alternative embodiment, where the guide arrangement comprises the first filter element and second filter elements positioned on or facing opposite sides of the reaction vessel, the detectors and the beam splitter arrangement are positioned on opposite sides of the reaction vessel such that the excitation path of each split excitation beam from the beam splitter arrangement to the first filter element is substantially parallel with the detection path of the reaction light from the reaction vessel to the second filter element. For example, the first filter element could be positioned facing a bottom side of the reaction vessel, while the second filter element could be positioned facing a top side of the reaction vessel.

In an embodiment, the device is suitable or configured for one or more amplification of nucleic acids including analysis of polymerase chain reactions (such as quantitative polymerase chain reactions), protein analysis, ligand analysis, or fluorescence analysis of chemical reactions. In a further embodiment, the device is suitable or configured for all of: analysis of polymerase chain reactions (such as quantitative polymerase chain reactions), protein analysis, ligand analysis, and fluorescence analysis of chemical reactions. In a further embodiment, the device may alternatively or additionally be suitable or configured for detection and/or analysis of Raman phenomena or two photon processes.

In accordance with a second aspect, the invention may broadly be said to consist in a device for detecting molecule (s), the device comprising a sample chamber adapted to receive and contact a reaction vessel, the sample chamber comprising:

a vessel receptacle thermally coupled to a heat exchange device, the vessel receptacle being shaped to receive and substantially encompass the reaction vessel, and having a relatively high thermal conductivity and low thermal mass;

a housing substantially enclosing the vessel receptacle and having an aperture at or substantially adjacent an open end of the vessel receptacle to permit insertion of the reaction vessel in the vessel receptacle; and wherein the vessel receptacle is substantially insulated from the housing.

In an embodiment, the vessel receptacle comprises a substantially conical body having a bore for receiving the reaction vessel, and a substantially planar base for thermal coupling with the heat exchange device, wherein the conical body diverges from the planar base towards the open end.

In an embodiment, the vessel receptacle comprises copper. Alternatively, the vessel receptacle may comprise silver or aluminium, or a combination of any one of copper, silver, gold and aluminium. In a further embodiment, the vessel receptacle has a thermal conductivity higher than about 200 $Wm^{-1}K^{-1}$. In a further embodiment, the vessel receptacle has a specific heat capacity of up to about $1.0\ Jg^{-1}K^{-1}$ at 25° C.

In an embodiment, where the vessel receptacle is configured to receive four reaction vessels, the mass of the vessel receptacle is up to about 16 g.

In an embodiment, the housing comprises white Acetyl, nylon, or polytetrafluoroethylene (PTFE). In a further embodiment, the housing has a thermal conductivity of about $0.25\ Wm^{-1}K^{-1}$.

In an embodiment, the vessel receptacle is substantially insulated from the housing via an air gap. Alternatively, an insulative material may be provided between the vessel receptacle and the housing. In a further embodiment, the insulative material has a thermal conductivity of up to about $0.03\ Wm^{-1}K^{-1}$. The insulative material may be aerogel, fibreglass, polystyrene, or other similar material(s), for example.

In an embodiment, the heat exchange device comprises a thermoelectric cooling (TEC) device.

In an embodiment, the TEC device has a first side in physical contact with the vessel receptacle, and a second side in physical contact with a heat sink.

In an embodiment, the heat sink is thermally coupled to a casing of the device for detecting molecule(s).

Alternatively, the device may include a further TEC device having a first side in physical contact with the heat sink, and a second side thermally coupled to a casing of the device.

In an embodiment, the or each TEC device may be a single-stage, two-stage or multiple-stage TEC device.

In an embodiment, the device for detecting molecule(s) further comprises:
- a controller associated with the heat exchange device and configured to control a temperature profile of the sample chamber to perform a reaction;
- an excitation assembly for inducing a reaction light in a reaction mixture in the reaction vessel; and
- a detector for optically detecting said fluorescence.

In an embodiment, the controller comprises a microcontroller communicatively coupled to a controller of the heat exchange device and a temperature sensor at or adjacent the vessel receptacle, forming a closed-loop feedback control system.

In an embodiment, the excitation assembly and detector are each adapted to be optically coupled with a reaction vessel via the aperture in the housing, by way of respective excitation and detection optical paths.

In an embodiment, both the excitation and detection optical paths are folded. Alternatively, either the excitation optical path or the detection optical path is folded.

In an embodiment, the excitation assembly comprises an excitation source. In a further embodiment, the excitation source is a light emitting diode (LED). In a further embodiment, the excitation assembly may comprise a laser source.

In an embodiment, the detector comprises a photodiode configured to detect fluorescence emitted from within the reaction vessel.

In an embodiment, the device further comprises a dichroic mirror adapted to fold or reflect said excitation light from the excitation source substantially orthogonally with respect to the excitation light from the excitation source towards the aperture in the housing.

In an embodiment, the dichroic mirror allows said fluorescence emitted from within the reaction vessel substantially co-axial with the aperture to pass substantially without reflection or refraction.

In an embodiment, the dichroic filter may be replaced by a multi-transition interference filter, such as a trichroic element, a notch filter, or a multi-band bandpass filter.

In an embodiment, the detection optical path comprises a turning mirror adapted to reflect said fluorescence emitted from within the reaction vessel substantially orthogonally towards the photodiode.

In an embodiment, the excitation arrangement assembly further comprises a collimating lens and a clean-up filter.

In an embodiment, the detector further comprises a long-pass filter.

In an embodiment, the device further comprises a power source comprising at least one battery adapted to power the apparatus in use.

In an embodiment, the device is for detecting molecule(s) in a plurality of reaction vessels and the device comprises an optical assembly as described in the first aspect of the invention. In a further embodiment, the heat exchange device of the device for detecting molecule(s) in a plurality of reaction vessels comprises a plurality of TEC devices, each TEC device arranged to be in thermal communication with one or more of the reaction vessels. In a further embodiment, the device comprises two vessel receptacles and is for detecting molecule(s) in two reaction vessels, the device comprising two TEC devices, each TEC device thermally coupled to a respective one of the vessel receptacles. Alternatively, the device may comprise one TEC device that is thermally coupled to both vessel receptacles. In a further embodiment, the device comprises four vessel receptacles and is for detecting molecule(s) of samples in four reaction vessels, the device comprising plurality of TEC devices thermally coupled to the vessel receptacles.

In an embodiment, the device is suitable or configured for one or more of amplification of nucleic acids including analysis of polymerase chain reactions (such as quantitative polymerase chain reactions), protein analysis, ligand analysis, or fluorescence analysis of chemical reactions. In a further embodiment, the device is suitable or configured for all of: analysis of polymerase chain reactions (such as quantitative polymerase chain reactions), protein analysis, ligand analysis, and fluorescence analysis of chemical reactions. In a further embodiment, the device may alternatively or additionally be suitable or configured for detection and/or analysis of Raman phenomena or two photon processes.

In accordance with a third aspect of the present invention, there is provided a heater for heating a substantially transparent or translucent cover of a reaction vessel, the heater comprising:
- a board having a primary aperture through which an excitation beam and/or a reaction light is configured to pass into/from a reaction vessel via the cover;
- at least one heating element configured to heat the cover, the heating element(s) positioned proximate to the primary aperture and being arranged on a front face of the board which is adapted to face the cover; and
- a thermal conductor arranged on a back face of the board and having an arrangement corresponding substantially to the arrangement of heating element(s) on the front face, the conductor being in thermal communication through the board with the heating element(s), and the conductor being connectable or connected to a sensor for sensing a temperature of the heating element(s).

In an embodiment, the board further comprises an insulative material arranged around the heating element(s) to substantially frustrate heat between the heating element(s) and the remainder of the board. In a further embodiment, the insulative material comprises at least one secondary aperture. In other embodiments, the board may not comprise secondary aperture(s).

In an embodiment, the board is a printed circuit board (PCB). In a further embodiment, the board has a thickness of about 0.6 mm. In a further embodiment, the conductor is an electrically and thermally conductive track printed on the board. In a further embodiment, the conductor is a copper track.

In an embodiment, the sensor comprises a resistance temperature detector (RTD) having a resistance property that varies in response to the sensed temperature. In a further embodiment, the sensor comprises a platinum resistance temperature detector.

In an embodiment, the heating element(s) is/are configured to radiate heat onto the cover based on at least the sensed temperature. In a further embodiment, the heating element(s) is/are coupled to a pulse-width modulator (PWM) for controlling the heat output by the heating elements. Alternatively, the heating element(s) is/are coupled to a comparator which is configured to control the heating element(s) based on at least the sensed temperature and a predetermined temperature value. In a further embodiment, the predetermined temperature value is about 100° C.

In an embodiment, the heating element(s) is/are arranged to be positioned at about 1.5 mm to about 3 mm from the cover of the reaction vessel. In a further embodiment, the heating element(s) is/are arranged to be positioned about 2 mm from the cover of the reaction vessel.

In an embodiment, where more than one reaction vessel may be present, the board comprises more than one primary aperture therethrough, each primary aperture for facilitating the passage of an excitation beam and/or a reaction light into/from a respective one of the reaction vessels, and the heater comprises heating elements positioned proximate to the primary apertures on the first face and thermal conductor (s) on the back face.

In an embodiment, the heater comprises more than one heating element positioned around the primary aperture. In a further embodiment, the heating elements that are positioned around the primary aperture are conductively connected to each other. Preferably, the heating elements positioned around the primary aperture are thermally and/or conductively connected to one or more heating elements proximate to another primary aperture in the board. In a further embodiment, the thermal conductor on the back face of the board is thermally and/or conductively connected to one or more conductors on the back face.

In an embodiment, the heater is used in a device for detecting molecule(s) which comprises the optical assembly of the first aspect of the invention as previously described. Additionally or alternatively, the heater may be used in the device of the second aspect of the invention for detecting molecule(s) as previously described. Alternatively, the heater may be used in any suitable device to prevent or mimimise the formation of condensation on a component of the system, such as when operating a device in a cold room or extreme environment (outside during winter or in the tropics) where the reaction temperature and the ambient temperature differ.

In this specification where reference has been made to patent specifications, other external documents, or other sources of information, this is generally for the purpose of providing a context for discussing the features of the invention. Unless specifically stated otherwise, reference to such external documents or such sources of information is not to be construed as an admission that such documents or such sources of information, in any jurisdiction, are prior art or form part of the common general knowledge in the art.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term '(s)' following a noun means the plural and/or singular form of that noun.

As used herein the term 'and/or' means 'and' or 'or', or where the context allows both.

Where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Embodiments of the present invention will now be described by way of example only and with reference to the accompanying drawings in which:

FIG. 37b shows a second layer of the lens heater shown in FIG. 37a;

DETAILED DESCRIPTION OF PREFERRED EMBODIMENTS

Embodiments of the present invention relate to a compact handheld portable device for detecting molecule(s). The device may be suitable or configured for amplification and detection of nucleic acids in a sample. For example, the device could be used for polymerase chain reaction (PCR) analysis (including quantitative PCR analysis). The device may additionally or alternatively be suitable or configured for one or more of: protein analysis, ligand analysis, or fluorescence analysis from any chemical reaction for example. Further, the device may be used for detecting molecule(s) within a single reaction vessel, or in a plurality of samples from the same or different sources within a plurality of reaction vessels.

Figure 1:
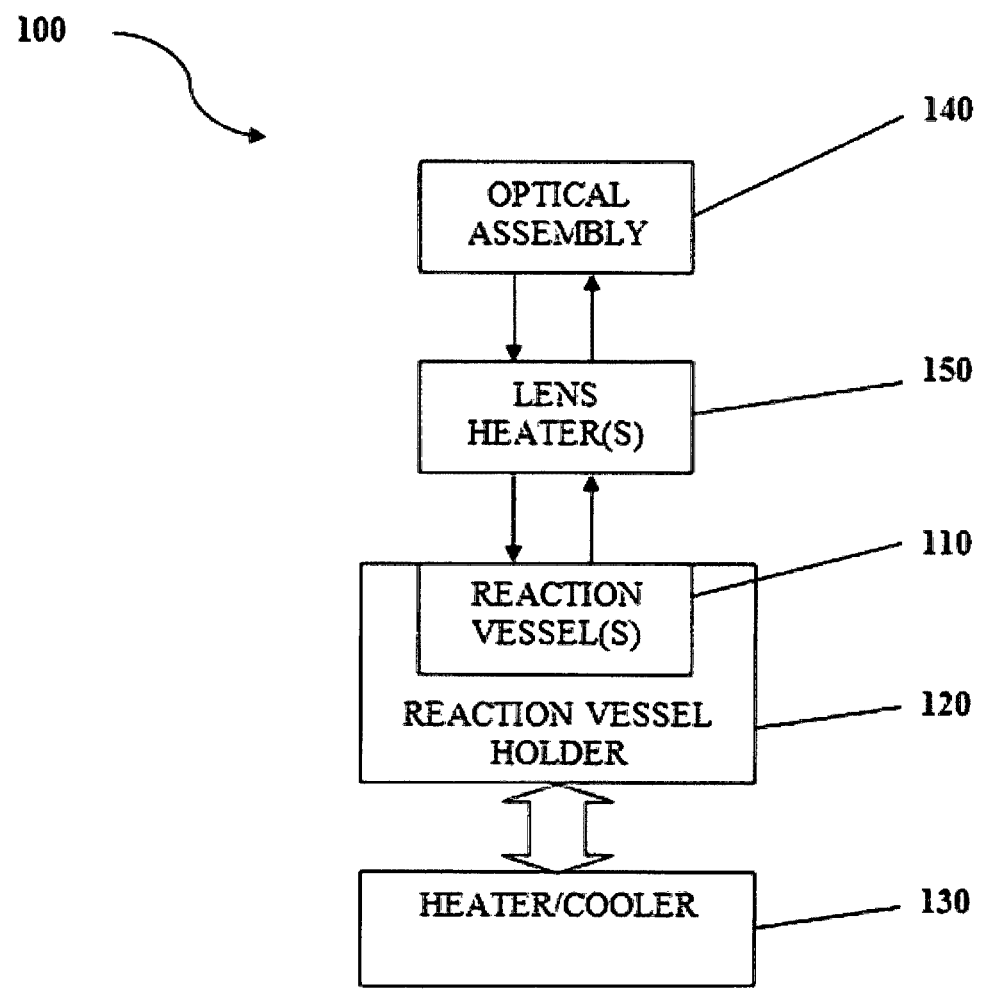
FIG. 1 shows a general block diagram of a device of an embodiment of the present invention.

Referring to FIG. 1, the device 100 of an embodiment of the present invention generally comprises a reaction vessel holder 120 for receiving one or more reaction vessels 110 containing a sample. A heater/cooler (or heat exchange device) 130 is coupled to the reaction vessel holder 120 to control the temperature of the sample within the reaction vessel(s) 110. For example, the heater/cooler 130 is configured to increase and/or decrease the temperature of the sample within the reaction vessel(s) 110 held by the reaction vessel holder 120 and/or to maintain the temperature at a desired level. Where the device 100 is suitable or configured for amplification and detection of nucleic acids, the process of heating and/or cooling the samples within the reaction vessels 110 in one or more stages results in amplification of the nucleic acids in the sample.

The device 100 further comprises an optical assembly 140 for detection of the molecule(s) in the sample(s) within the reaction vessel(s) 110. Generally, the optical assembly 140 is configured to transmit a beam of excitation radiation toward the reaction vessel(s) 110 which stimulates an emission of a reaction light such as fluorescence from the sample within the reaction vessel(s) 110. The optical assembly 140 is further configured to receive the reaction light from the reaction vessel(s) 110. The optical assembly 140 may be coupled to a controller for analysis of the detected molecule(s).

The device 100 may also comprise a reaction vessel cover heater 150 through which the excitation beam and the reaction light may pass. The reaction vessel cover heater 150 is configured to heat the cover(s) of the reaction vessel(s) 110 to prevent the sample(s) from evaporating and condensing on the cover(s) of the reaction vessel(s) 110 during the heating and cooling processes. In some embodiments of the device, the reaction vessel cover heater 150 may not be present.

These components will be described in further detail below.

The Reaction Vessel

Figure 2:
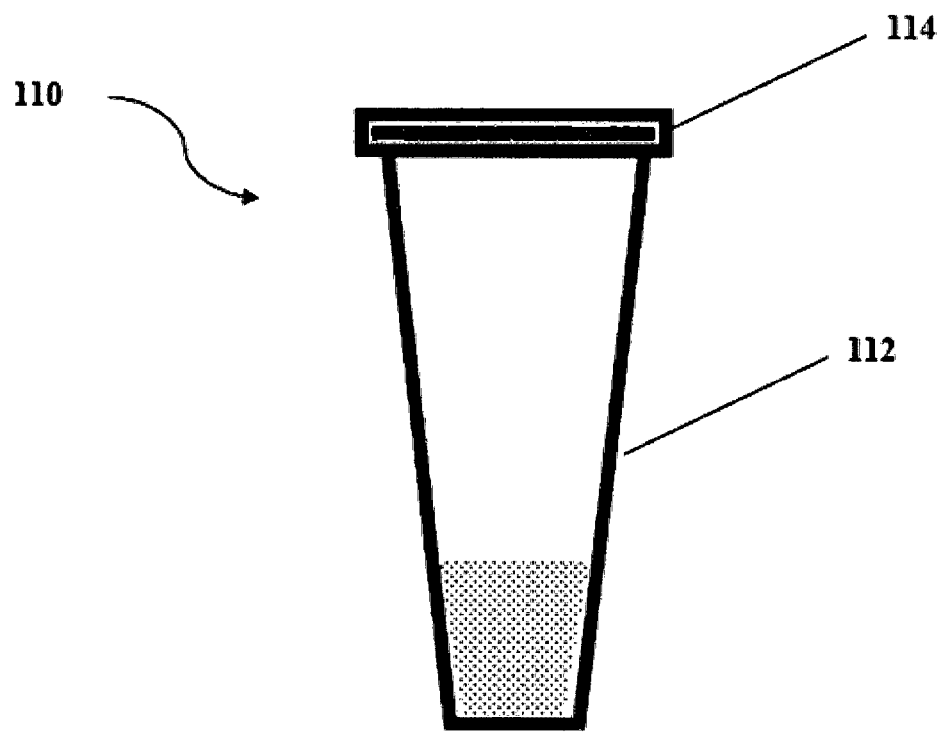
FIG. 2 shows an example reaction vessel that may be used in the device of the present invention.

An example reaction vessel 110 which contains the sample to be analysed is shown in FIG. 2. The reaction vessel 110 may be a small low-cost and disposable plastic test tube.

The reaction vessel has a tubular body 112 with a substantially conical distal end and a mouth at a proximal end. The reaction vessel is provided with a removable cover 114 which is used to substantially seal the mouth of the body 112 during the heating/cooling process to avoid the sample from evaporating outside the reaction vessel 110 when heated by the heater/cooler 130 which would contaminate the device 100 and affect future results. The cover 114 may be a separate component from the body 112 of the reaction vessel 110. For example, the cover 114 may be a thin transparent sheet which covers the mouth of the reaction vessel 110. Alternatively, the cover 114 may be for example, hingedly connected to the body 112. At least the cover 114 of the reaction vessel 110 is substantially transparent or translucent so that an optical path can be established between the sample to be analysed and the optical assembly 140, as will be described in further detail below.

Reaction vessels of the type described in U.S. Pat. Nos. 4,713,219 or 5,270,011, for example, may be suitable for use in embodiments of the present invention. Embodiments of the invention will be described below with respect to such a reaction vessel although it is to be appreciated that the invention may be easily modified or adapted for use with any suitable reaction vessel.

Where the device is for detecting molecules in a plurality of reaction vessels, the reaction vessels may be separately or integrally formed.

The Reaction Vessel Holder

Figure 3:
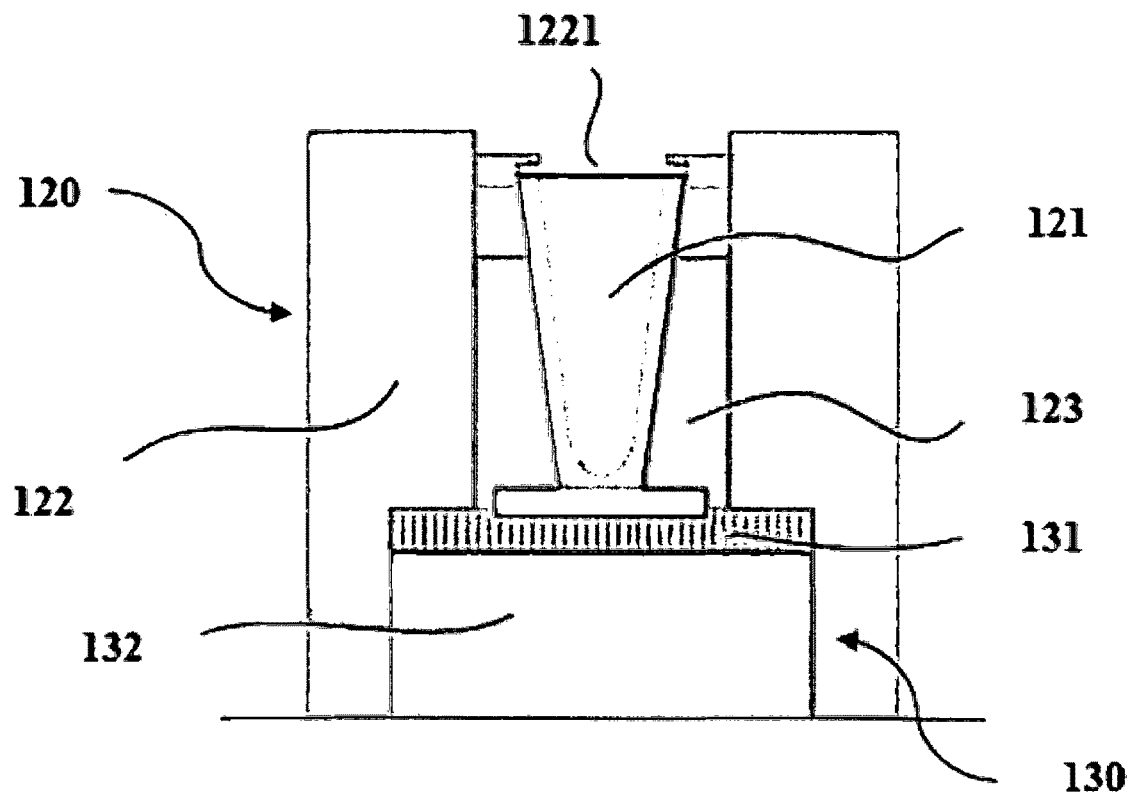
FIG. 3 shows a cross-sectional side view of a reaction vessel holder and heater/cooler an embodiment of the present invention.

Referring to FIG. 3, the reaction vessel holder 120 is adapted to receive one or more reaction vessels (not shown) containing a sample to be analysed. The reaction vessel holder 120 provides good thermal coupling between the heater/cooler 130 and a reaction vessel (such as the reaction vessel 110 shown in FIG. 2 for example).

The preferred embodiment of the reaction vessel holder 120 comprises one or more vessel receptacles 121 and a housing 122. The vessel receptacle(s) 121 is/are insulated from the housing 122, via an insulating material 123 for example.

The vessel receptacle 121 preferably has a high thermal conductivity and low thermal mass to facilitate rapid heat transfer between the heater/cooler 130 (described in further detail below), vessel receptacle 121, and the sample within the reaction vessel 110 (or vice versa) for maximum efficiency.

The thermal mass refers to the ability of an object to retain heat. An object with a low thermal mass has a low heat capacity or low specific heat capacity, and requires little heat to increase the temperature of the object. The object will have a low mass.

The preferred material for the vessel receptacle 121 is copper, which has a thermal conductivity k of approximately 380 $Wm^{-1}K^{-1}$ to 401 $Wm^{-1}K^{-1}$ and a specific heat capacity of about 0.385 $Jg^{-1}K^{-1}$ at 25° C. Other materials with a high thermal conductivity in the range of about 200 $Wm^{-1}K^{-1}$ to about 401 $Wm^{-1}K^{-1}$ could be used for the vessel receptacle 121. Materials with a low specific heat capacity in the range of about 0.3 $Jg^{-1}K^{-1}$ to about 0.9 $Jg^{-1}K^{-1}$ at 25° C. can be used for the vessel receptacle 121. Materials such as gold, silver or aluminium, or a combination of materials for example, could be used for the vessel receptacle 121 without departing from the scope of the invention. Approximate values of the thermal conductivity and specific heat capacity of materials that could be used for the vessel receptacle 121 are shown below:

| Material | Thermal conductivity ($Wm^{-1}K^{-1}$) | Specific heat capacity at 25° C. ($Jg^{-1}K^{-1}$) |
|---|---|---|
| Aluminium | 200-250 | 0.904 |
| Copper | 350-400 | 0.386 |
| Gold | 310-320 | 0.129 |
| Silver | 400-430 | 0.233 |

The vessel receptacle 121 has a specific heat capacity of up to about 1.0 $Jg^{-1}K^{-1}$ at 25° C. Where the vessel receptacle 121 is configured to receive four reaction vessels, the mass of the vessel receptacle 121 may be more than 0 g and up to about 16 g. The mass is considered low as 16 g is 'small' compared to the mass of the overall device (which may be up to about 1.62 kg for example). 16 g is also the maximum metallic mass that can be temperature cycled at an acceptable rate and duration with a Lithium-ion battery bank (occupying ~40% of the upper casing volume) which is discussed in further detail below.

Figure 4:
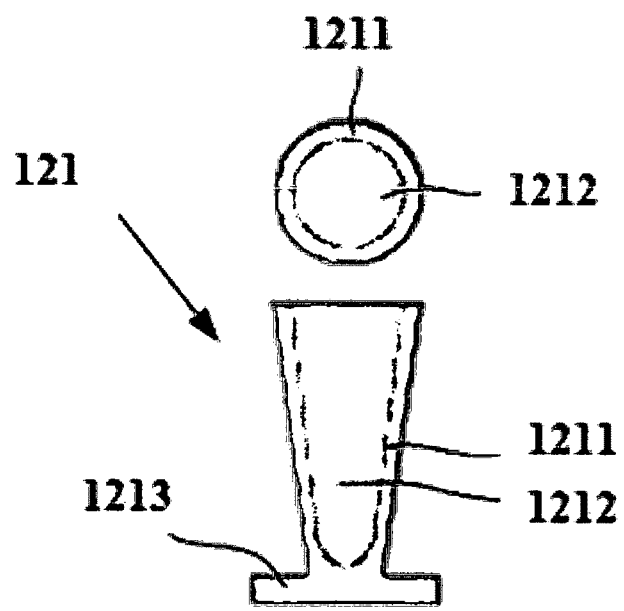
FIG. 4 shows a top view and cross-sectional side view of a vessel receptacle of the reaction vessel holder shown in FIG. 3.

The vessel receptacle 121, shown in further detail in FIG. 4, has a body 1211 having a bore 1212 which is preferably shaped to receive and substantially enclose or 'cup' a reaction vessel (such as for example the reaction vessel 110 shown in FIG. 2). When a reaction vessel is placed into the vessel receptacle 121, the top of the reaction vessel may project beyond the vessel receptacle 121 to maintain the maximum possible surface area contact between the reaction vessel and the vessel receptacle 121, while allowing the reaction vessel to be easily removed from the vessel receptacle 121.

The external shape of the body 1211 corresponds substantially with that of the bore 1212, whereby the body 1211 comprises a single continuous wall forming a substantially (inverted) conical or frustoconical shape corresponding substantially with the shape of the reaction vessel. The wall of the body 1211 may have a thickness of about 1 mm for example. This design minimises the mass of the vessel receptacle 121 and allows rapid changes in heat of the sample within the reaction vessel.

The body 1211 of the vessel receptacle 121 diverges outwardly from a substantially planar base 1213, which is formed integrally with the body 1211. The base 1213 provides a greater surface area to physically contact the heater/cooler 130 and to establish a good thermal coupling between the vessel receptacle 121 and the heater cooler 130.

Referring again to FIG. 3, the remainder of the vessel receptacle 121 is substantially surrounded by an insulative material 123 to minimise heat loss and to maximise efficiency by ensuring heat in the vessel receptacle 121 is transferred to or from the reaction vessel with minimal losses. The insulative material 123 is configured to inhibit convection between the vessel receptacle 121 and the housing 122. The insulative material 123 comprises aerogel such as silica aerogel. Aerogel ties air up in small packet volumes to inhibit convection between the vessel receptacle 121 and the housing 122. The insulative material 123 may additionally or alternatively comprise fibreglass, polystyrene, or similar material(s). In an alternative embodiment, rather than using an insulative material 123, an air gap may be provided between the vessel and housing (in region 123) to insulate the vessel from the housing. The insulative material 123 preferably has a thermal conductivity of less than about 0.03 $Wm^{-1}K^{-1}$. Silica aerogel typically has a thermal conductivity in the range of about 0.004 to about 0.03 Wm$^{-1}$K$^{-1}$. An air gap typically has a thermal conductivity of about 0.03 Wm$^{-1}$K$^{-1}$.

The vessel receptacle 121 and insulative material 123 is contained within a housing 122 which has a relatively low thermal conductivity of less than about 0.25 Wm$^{-1}$K$^{-1}$, and is preferably made from white acetal, nylon, or polytetrafluoroethylene (PTFE) for example. PTFE has the benefits of being lightweight, easy to machine, heat resistant, and having a relatively low thermal conductivity (approximately 0.25 Wm$^{-1}$K$^{-1}$). The housing 122 has an opening or aperture 1221 at or adjacent the mouth of the vessel receptacle 121 to enable insertion and removal of the reaction vessel into/from the vessel receptacle 121, and to further provide an optical path between the reaction vessel held by the vessel receptacle 121 and the optical assembly (which will be discussed in further detail below).

In other embodiments of the invention, the reaction vessel holder 120 may be provided with a plurality of vessel receptacles integral with the planar base, for the simultaneous detection of molecules in a plurality of samples in a plurality of reaction vessels.

According to alternative embodiments, the reaction vessel holder may be in the form of a cassette housing that comprises one or more reaction chambers that can be closed. In these embodiments, the reaction vessels may be removable from or integral with the reaction vessel holder. The or each reaction chamber has a low volume and is configured to receive a sample for molecule detection. The or each reaction chamber is configured so that no air gap is present above the reaction mixture. By having no air gap into which the reaction mixture can evaporate, the need for lens heaters is eliminated. The housing may be disposable. The housing is optically transparent on at least one side to allow an excitation light to enter the reaction chamber that stores a sample and to allow a reaction light to exit the reaction chamber. According to an alternative embodiment, the housing is optically transparent on a first side to allow an excitation light to enter the reaction chamber and on a second side to allow a reaction light to exit the reaction chamber. The first and second sides may be on opposite sides of the housing. For example, a first side may be a bottom side of the housing while the second side is a top side of the housing, or vice-versa. In one embodiment, the reaction chambers in a housing are separable from each other. For example, a row of reaction chambers may be frangibly separated from other reaction chambers in the housing.

Heater/Cooler

The device comprises a heater/cooler device (or a heat exchange device) 130 for heating and/or cooling the sample in one or a plurality of stages. Referring again to FIG. 3, according to a preferred embodiment of the invention, the heater/cooler generally comprises a thermoelectric cooling (TEC) device 131 and a heat sink/fan 132.

A TEC device is generally a substantially planar solid-state device which uses the Peltier effect to transfer heat from one side of the device to the other upon application of a direct current (DC) voltage. By reversing the direction of the current, the direction of heat transfer can similarly be reversed.

The TEC device is ideal for use in the portable device of preferred embodiments of the present invention where the temperature of the sample must be alternately heated and cooled such as for example in a Q-PCR analysis. The TEC device has no moving parts, is relatively small and lightweight, can be easily powered by battery or a relatively low-voltage source, and can both heat and cool the sample in the reaction vessel.

Referring to FIG. 3, in a preferred embodiment of the invention, a first side of the substantially planar TEC device 131 is in direct physical contact with the base 1213 of the vessel receptacle 121 for an efficient thermal coupling therebetween. Alternatively, the first side of the TEC device 131 may be indirectly connected to the base 1213 of the vessel receptacle 121. In that alternative configuration, the TEC device 131 is still in substantial thermal communication with the base 1213. The second, opposing, side of the TEC device 131 is in physical contact with the heat sink 132. The heat sink may for example comprise a metallic mass and a fan to actively dissipate an excess of heat. The heat sink 132 dissipate(s) heat from the second side of the TEC device 131 when the sample is cooled, and provides a source of heat when the sample is heated.

The heat sink 132 is preferably thermally coupled with the exterior casing of the device, which may also act as a heat sink/source. The casing is preferably a metallic material having a relatively high thermal conductivity, typically less than that of the heat sink 132 and/or vessel receptacle 120, but significantly higher than the insulative material 123 and of the housing 122. For example, the casing may have a thermal conductivity between about 12 Wm$^{-1}$K$^{-1}$ and about 240 Wm$^{-1}$K$^{-1}$. Suitable materials for the casing may include stainless steel or aluminium for example. The casing will be described in further detail below.

Each TEC device could be a single- or two-stage TEC device. Alternatively, the TEC device could be a multiple-stage TEC device, comprising three or more stages. Preferably the device is a two-stage TEC device which is a single unit with two TECs positioned in the unit. A typical single stage TEC device has a maximum temperature differential of approximately 70° C. TEC temperature differentials are additive and therefore a two-stage TEC device has a maximum temperature differential of approximately 140° C. For the device of the present invention to operate reliably in the field, it must be capable of operating reliably and consistently in a wide range of environmental conditions and ambient temperatures. In another embodiment of the invention, the device may be provided with a further TEC device between the heat sink 132 and the apparatus casing. In this configuration, the heat sink 132 becomes a thermal reservoir and the further TEC device is adapted to maintain the heat sink at a substantially constant temperature, preferably in the region of 30-40° C., while the first TEC device 131 is adapted to vary the temperature of the vessel receptacle 121 by transferring heat between the heat sink 132 (thermal reservoir) and the vessel receptacle 121 as necessary.

In either the single- or two-stage configuration, as appropriate, either or both of the 'first' and 'further' TEC devices may actually comprise a plurality of independently controlled TEC devices or modules, typically provided side-by-side in a plane. In a preferred embodiment of a device having four vessel receptacles, the 'first' TEC device comprises three two-stage TEC devices in parallel, with the vessel receptacles thermally coupled to the TEC devices. The TEC devices are further thermally coupled to a unitary thermal reservoir or heat sink.

The operation of the TEC device 131 is controlled by a controller which is described in further detail below.

Optical Assembly for Detection of Molecule(s)

Figure 5:
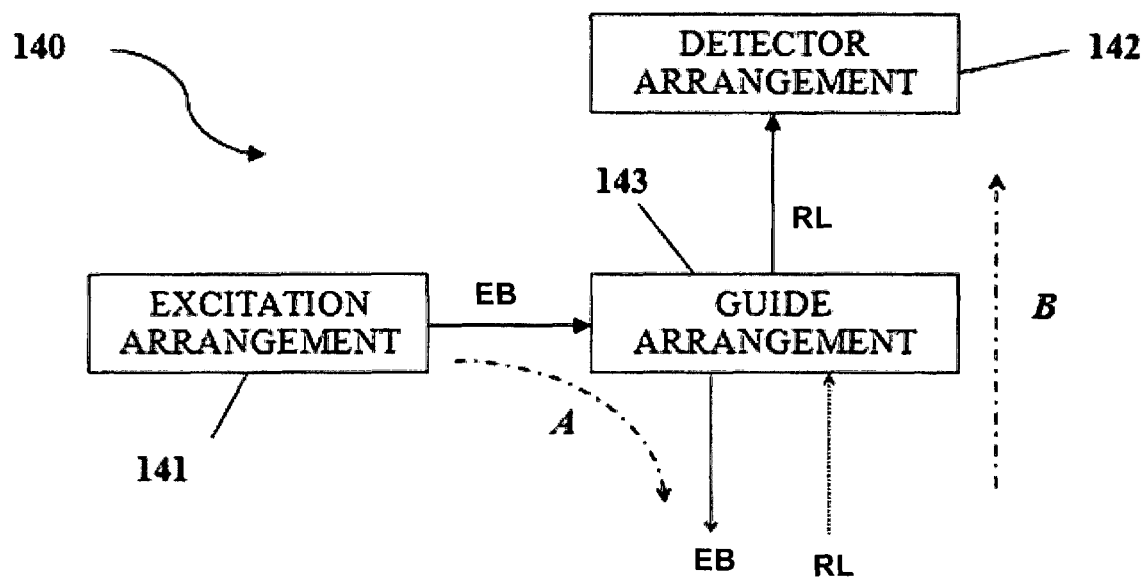
FIG. 5 shows general block diagram of an optical assembly of an embodiment of the present invention.

FIG. 5 shows the general block diagram of the optical assembly 140 of the present invention. The optical assembly 140 is a modular optical unit configured to evenly distribute an excitation radiation beam EB to one or more samples within one or more of the reaction vessels. The optical assembly 140 is further configured to measure reaction light RL such as fluorescence for example from the sample(s) within the reaction vessel(s). The optical assembly 140 is miniaturised for incorporation into the portable hand held compact device of embodiments of the present invention.

The optical assembly 140 comprises an excitation arrangement 141 which is configured to generate one or more excitation radiation beams EB. The excitation beam(s) EB follow(s) an excitation path A to the reaction vessel(s). The (or each) excitation beam is used for illuminating the sample within a reaction vessel in the device. Upon excitation by the excitation means, successful amplification of the target molecules (for example DNA) will result in fluorescence or emission of reaction light at a wavelength (different from the wavelength of the excitation beam) from the sample or a reporter dye. The excitation arrangement 141 and detector arrangement 142 are preferably both designed specifically to excite and detect fluorescence of a particular dye, which in the case where the device is used for Q-PCR analysis of nucleic acids is most preferably the SYBR® Green dye available from Invitrogen Corporation of Carlsbad, Calif. However, the device may be easily modified or adapted for use with any other suitable dye having emission wavelengths in the range of about 442 nm to about 814 nm, such as those described in the 'Summary of the Invention' section above for example.

The reaction light RL follows a detection path B to a detector arrangement 142 which is part of the optical assembly 140 for detection. The optical assembly 140 further comprises a guide arrangement 143 for guiding the excitation path A of an excitation beam EB from the excitation arrangement 141 toward a reaction vessel. The guide arrangement 143 is further configured to guide the detection path B of the reaction light RL from the reaction vessel to the detector arrangement 142.

Figure 6:
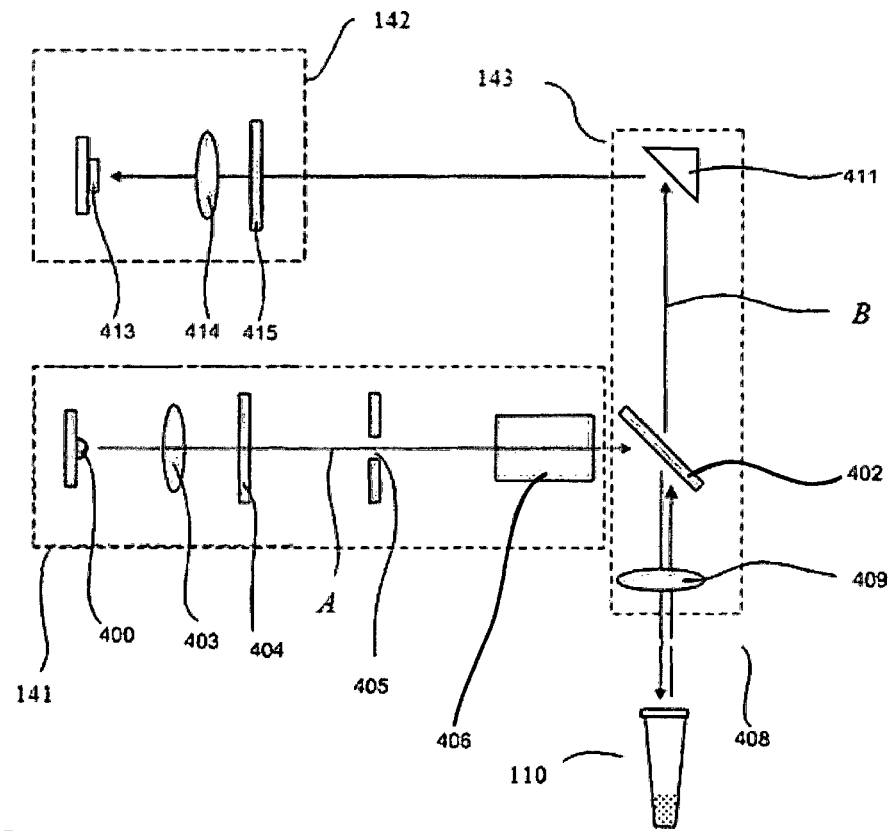
FIG. 6 shows a general layout of the optical assembly of an embodiment of the present invention for detecting molecule(s) within a single reaction vessel.
Figure 7:
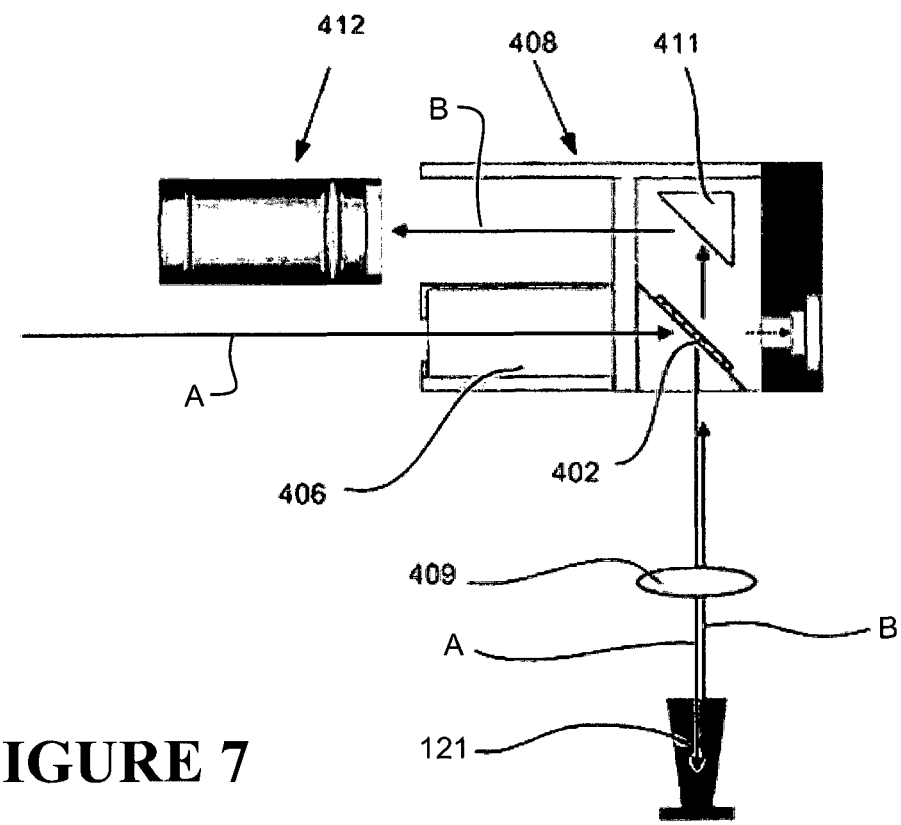
FIG. 7 shows a side view of the component layout of the optical assembly of an embodiment of the present invention for detecting the molecule(s) within a single reaction vessel.
Figure 8:
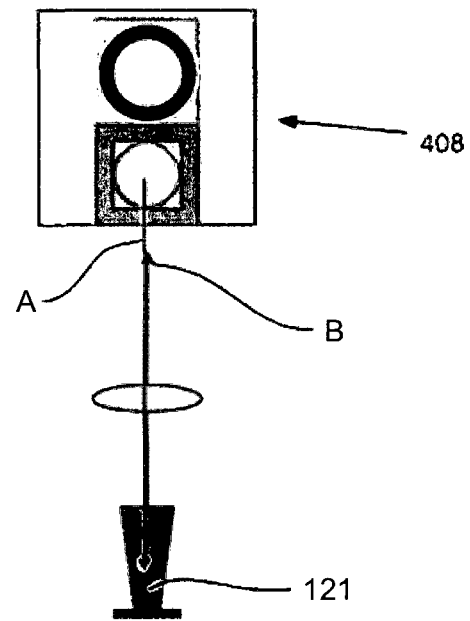
FIG. 8 shows a front view of the component layout of the optical assembly of an embodiment of the present invention for detecting the molecule(s) within a single reaction vessel.

The different sections of the optical assembly will be discussed in further detail below with reference to FIGS. 6 to 8 which show a general component layout of an embodiment of a device for detection of molecule(s) in a single reaction vessel 110.

Figure 11:
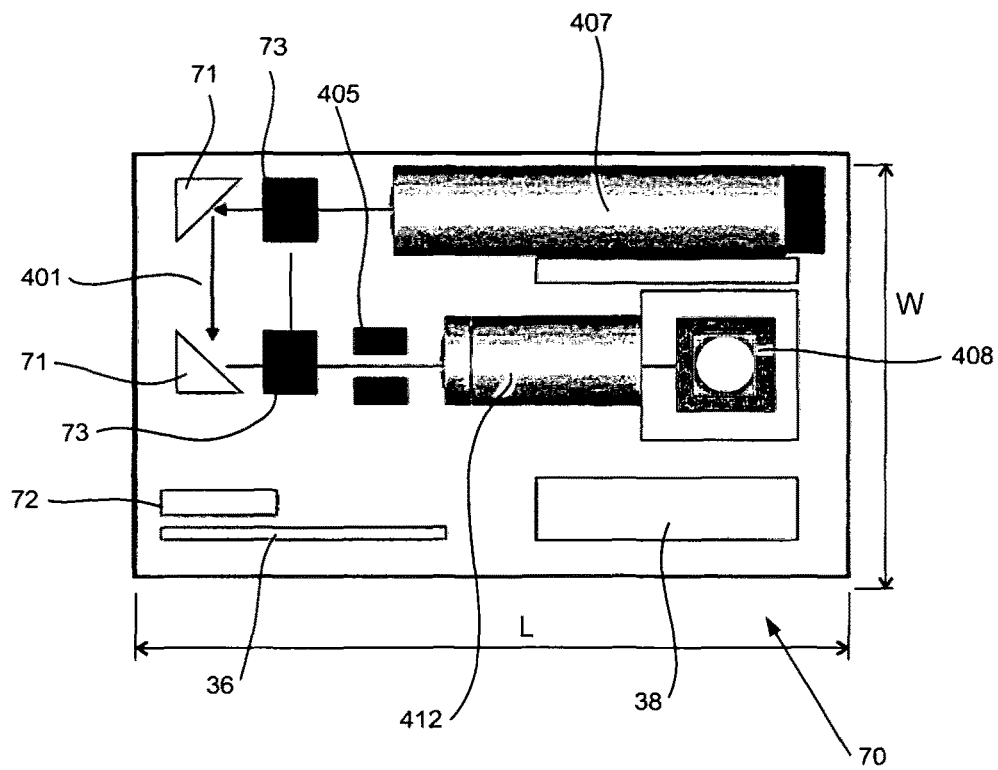
FIG. 11 shows a top view of an upper casing of the device for detecting molecule(s) in a single reaction vessel according to an embodiment of the present invention.
Figure 12:
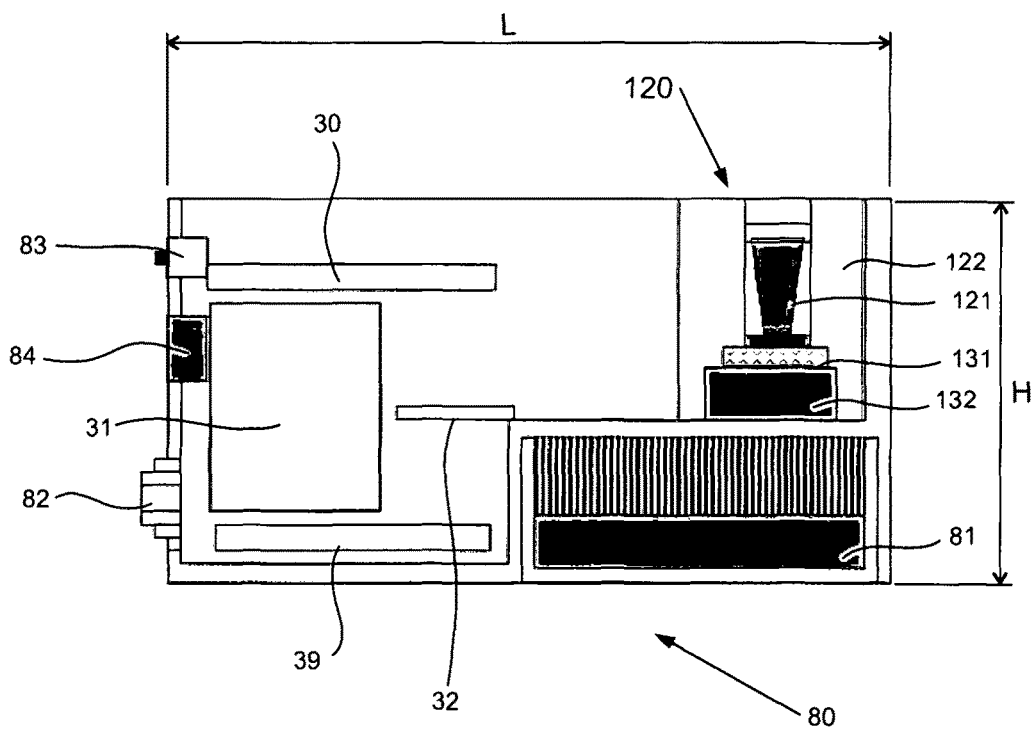
FIG. 12 shows a side view of a lower casing of the device for detecting molecule(s) in a single reaction vessel according to an embodiment of the present invention.

FIGS. 11 and 12 show an example layout of a device for detecting molecule(s) within a single reaction vessel. The device comprises a heater/cooler which has been previously described. The device may further comprise a reaction vessel cover heater which is described in further detail below with reference to FIGS. 36 to 39.

The Excitation Arrangement 141

The excitation arrangement 141 comprises an excitation source 400 for generating the excitation beam. The excitation source 400 may be a laser light source or a light emitting diode (LED). Suitable excitation sources include for example a Nichia laser diode configured to emit an excitation beam having a wavelength of about 470 nm or 473 nm, or a Luxeon® Rebel 5 model 470 nm, 500 mW LED available from Philips Lumileds Lighting Company of San Jose, Calif. However, any excitation beam having a wavelength in the range of about 346 nm to about 784 nm may be used for example.

According to some embodiments, the excitation arrangement comprises a plurality of excitation sources. In these embodiments, each excitation source is configured to transmit an excitation beam at a different wavelength from the other excitation sources. The excitation beams from the excitation sources are combined to form the excitation beam for the beam splitter arrangement. The excitation arrangement comprises beam combination optics for combining the plurality of excitation beams to form the excitation beam for the beam splitter arrangement. In one embodiment, the excitation beam for the beam splitter arrangement comprises a red wavelength and a blue wavelength, or a green wavelength and a blue wavelength, or a green wavelength and a red wavelength. In an alternative embodiment, the excitation beam for the beam splitter arrangement comprises red, green and blue wavelengths. The use of a plurality of excitation wavelengths allows for a plurality of tests to be carried out on a sample. The use of a plurality of wavelengths provides the device with the ability to measure fluorescent reporters at a plurality of wavelengths.

The excitation source 400 is optically coupled with the reaction vessel 110 in the vessel receptacle 121 to provide an excitation beam to the sample through the translucent cover 114 of the reaction vessel 110, via the aperture 1221 in the housing 122 of the reaction vessel holder 120 which have been previously described with reference to FIGS. 2 to 4. The excitation optical path A is 'folded' so that the excitation source 400 is not necessarily co-axial with the reaction vessel 110. The excitation optical path length thus exceeds the straight-line distance between the excitation source 400 and the reaction vessel 110, thereby minimising the physical size of the device without compromising the optical path length. The excitation source 400 is directed at an angle substantially orthogonal to the longitudinal axis of the reaction vessel 110 and aperture 1221 of the housing 122 of the reaction vessel holder 120.

A collimator in the form of a collimating lens 403 is used to collimate the excitation beam from the excitation source 400. The collimating lens 403 may be a C240TME-A, f=8 mm aspheric collimating lens supplied by Thorlabs. The collimating lens 403 may be an aspheric collimating lens. The collimating lens 403 may have a focal length of about 8 mm or about 12 mm to provide a substantially collimated beam of excitation radiation to the reaction vessel 110. For embodiments where the excitation source 400 is a laser light source, the collimating lens 403 collimates the highly divergent excitation beam from the laser diode into a near as possible collimated/parallel beam. This allows a laser diode clean up filter (an interference type filter) which may be part of the excitation arrangement 141 to operate correctly. The main requirement for collimated light however is in the distance independent beam splitting and projection (to the sample) system. Because collimated light looks/behaves similarly for most practical purposes at the source or in the far field (some distance from the source) there is no need to have long optical path lengths as for systems with divergent/convergent light beams as found in imaging and focusing systems (such as where the light source is sent through a diverging optic in order to irradiate a number of sample wells in what is effectively the far field. The use of collimated light starting at the light source allows for a compact construction of the device. In one embodiment, the collimating lens 403 is part of the excitation source 400. In an alternative embodiment, the collimating lens may be separate from the excitation source.

The collimated beam then passes through an attenuator 404 to reduce power levels of the excitation beam, if required, to suitable values. If the power level of the excitation beam is suitable, the attenuator 404 may not be present. The attenuator 404 according to the preferred embodiment of the invention is a neutral density filter. The neutral density filter used in the device may be an NE510B filter supplied by Thorlabs for example. The filter 404 is most preferably a clean-up or band-pass filter which in particular filters out any wavelengths in the vicinity of the fluorescence wavelength of intercalating dye added to the sample. According to the preferred embodiment of the invention, the clean-up filter has a centre wavelength of about 470 nm and a bandwidth of approximately 10 nm. The neutral density filter (ND filter) has attenuating properties that are wavelength independent. The device uses a OD=1.0 neutral density ND filter to reduce the incident laser energy by a factor of 10. This is because the Nichia 470 nm laser diode is approximately ten times more powerful than what is required when running at the recommended stable operating current.

The excitation arrangement 141 further comprises a wavelength filter for removing broadband spontaneous emission component of laser output. In the case where the excitation source 400 is a laser source, the wavelength filter is a laser line clean up filter. The laser diode clean-up filter may be a MaxDiode LD01-473/10-12.5 filter supplied by Semrock for example. The laser diode clean up filter is a dielectric type interference filter which requires nominally collimated light to perform as described in the data sheet. The laser line clean-up filter ensures that no portion of the excitation light falls within the spectrum of the reaction light from the sample. While 99.9% of the laser diode energy is constrained to within ~1 nm of the peak wavelength of 470 nm small amounts of light due to spontaneous emission can fall within the sample fluorescence interval which is currently ~500-600 nm.

The excitation beam A passes through an optical aperture 405 which is formed within a black acetyl material. The optical aperture 405 is used to remove any stray light. The optical aperture 405 is also used to reduce the diameter of the excitation beam A and to further create a well defined edge in the excitation beam commensurate with the remainder of the optical system.

The excitation beam A may further pass through a shroud 406. The shroud functions to prevent scattering light from entering or exiting the light propagation volume, and acts to keep wiring out of the light propagation volume.

Where the device is used for detecting molecule(s) in more than one reaction vessel, the excitation arrangement 141 may further comprise a beam splitter arrangement (which is described below with reference to FIGS. 14 and 15 for example) for splitting the excitation beam into a number of split excitation beams (or channels), each split excitation beam being used to illuminate the sample in a respective one of the reaction vessels. A device for detecting molecule(s) in a plurality of reaction vessels according to an embodiment of the present invention will be discussed in further detail below.

The excitation arrangement 141 may further comprise one or more linear polarisers for each channel, to attenuate the portion of incident light that is not aligned with the optical axis of the polarising element. The linear polariser(s) have a substantially circular circumference. As the laser diode light is at all times linearly polarised throughout the optical assembly 140, the linear polarisers offer the means to precisely trim the laser power (through rotating the polariser). Laser power is trimmed to better than 1% in this way. The importance of trimming the laser power is two-fold. Firstly, the fluorescent signal from the samples is proportional (outside of saturation effects) to the incident laser power. Widely differing signals from identical samples is not desirable. Secondly, photo bleaching effects of the sample (if present) will vary among otherwise identical samples due to variation in incident laser power thereby compromising the quality of the gathered data further.

The excitation arrangement 141 may include one or more additional steering mirror(s) to further fold the excitation optical path A as necessary for the device to remain compact.

The Guide Arrangement 143

The guide arrangement 143 is used to guide an excitation path A of an excitation beam from the excitation arrangement 141 into a reaction vessel 110 containing a sample to stimulate an emission of a reaction light from the sample. The guide arrangement 143 is further used to guide a detection path B of the reaction light from the sample towards a detector arrangement 142.

The guide arrangement 143 comprises filter element that, in the embodiment currently described, is a dichroic ('two colour') element 402. The dichroic element 402 is configured to be substantially reflective for wavelengths of the excitation beam from the excitation arrangement 141. Particularly, the dichroic element 402 is highly reflective (~100% R) for wavelengths of about 470 nm. The dichroic element 402 is further configured to be transmissive for wavelengths of the reaction light from the reaction vessel. Particularly, the dichroic element 402 is highly transparent/transmissive (~95% T) for wavelengths of about 500 nm to about 1000 nm.

A suitable dichroic element will be selected depending on the wavelength of the excitation beam and the wavelengths of the reaction light. For example, the dichroic element 402 may be a Brightline Di01-488-10×15 dichroic element provided by Semrock for example. The dichroic element 402 directs the excitation beam to the sample (via an imaging lens). Additionally, the dichroic element 402 is the first excitation filter element before the detector(s). The dichroic element 402 substantially blocks scattered excitation laser light from the reaction vessel 110 reaching the detector arrangement 142.

The dichroic element 402 is oriented at about 45° to the excitation path A from the excitation arrangement 141, and at about 45° to the detection path B from the reaction vessel such that the dichroic element reflects the incident excitation beam from the excitation source at an angle of about 90° with respect to the incident beam towards the longitudinal axis of the reaction vessel.

Fluorescence of the dye which is emitted substantially coaxial with the reaction vessel 110 passes substantially straight through a focussing/imaging lens 409 (which will be discussed in further detail below) and, importantly, the dichroic element 402, thereafter following a detection optical path B that is separate from the excitation path A from the excitation arrangement 141. The dichroic element 402 thus allows said fluorescence emitted from the reaction vessel 110 to pass substantially without reflection or refraction.

In an alternative embodiment, the dichroic element 402 may be transmissive at the wavelengths of the excitation beam and reflective at the wavelengths of the reaction light.

In an alternative embodiment, where the excitation arrangement is configured to transmit an excitation beam having a plurality of excitation wavelengths or where the reaction light comprises multiple reaction light wavelengths, the dichroic element may be replaced by a suitable multi-transition interference filter element, such as a trichroic element, a notch filter, or a multi-bandpass filter for example. An example of a suitable multi-transition interference filter may for example be a BrightLine® triple-band bandpass filter from Semrock. Alternatively, the dichroic element may be replaced by an arrangement of dichroic elements.

The guide arrangement 143 may further comprise a focussing/collimating lens 409. The lens 409 is arranged to image/focus excitation beam from the dichroic element 402 into the reaction vessel 110. The lens is further configured to collimate reaction light exiting the reaction vessel 110. The lens 409 has a focal length f of about 18 mm.

In order to precisely target the small volume of sample (typically present in only the lower ~1/10th of the reaction vessel 110), the excitation beam must be focused into this region. In this manner, a localized fluorescence volume is defined within the sample as dictated by the focused laser beam. The local laser intensity is higher in the focused region thereby producing enhanced fluorescence from this region. This is desirable provided saturation and bleaching effects are avoided through careful adjustment of laser power and irradiation duration. The effect of the localized fluorescent volume is to provide a fluorescent volume more akin to a point light source than a distributed light source (which occurs if a beam, focused or otherwise, is incident over the entire sample volume). The light from a point source is more readily collimated, from which it can be seen that due to the reversible nature of light ray propagation the imaging lens collimates that light impinging on it from the sample fluorescent volume (by virtue of the imaging lens focal point being located in the fluorescent volume).

Similar to the excitation arrangement 141, the detector arrangement 142 may also be arranged to receive reaction light from the reaction vessel via a folded light path. The guide arrangement 143 includes a turning mirror 411, which is preferably a dielectric mirror highly reflective at the fluorescence wavelength, arranged at 45° relative to the detection path from the dichroic element 402 to reflect the emitted fluorescence substantially orthogonally to the detector arrangement 142. The turning mirror 411 'folds' the detection optical path B to direct the emitted fluorescence towards the detector assembly 142.

In still other alternative embodiments, the guide arrangement may comprise an element for guiding a split excitation beam from the beam splitter arrangement to the reaction vessel and a separate element for guiding the reaction light from the reaction vessel to the detector. In one embodiment, the guide arrangement comprises a first filter element and a second filter element positioned on or facing opposite sides of the reaction vessel, wherein the reaction vessel is substantially optically transparent. For example, the first filter element may face a bottom side of the reaction vessel, while the second filter element may face a top side of the reaction vessel, or vice-versa. The first filter element is configured to guide a respective one of the split excitation beams along the excitation path from the beam splitter arrangement into the reaction vessel. The first filter element is configured to pass the excitation beam from the beam splitter arrangement toward the reaction vessel and to reflect the reaction light from the reaction vessel. According to other embodiments, the first filter element is configured to attenuate or block the reaction light from the reaction vessel. The second filter element is configured to guide reaction light from the sample along the detection path towards the detector. The second filter element is configured to pass the reaction light from the reaction vessel toward the detector and to attenuate or block the excitation beam. The first filter element and/or second filter element may comprise a dichroic element and/or a glass filter. Further, the first filter element and/or second filter element may be integral with the reaction vessel or reaction vessel holder that is substantially optically transparent. For example, a side of the reaction vessel holder may be coated with a material that reflects the reaction light while passing the excitation beam. In these embodiments, the guide arrangement comprises an imaging/focusing lens that is positioned between the second filter element and the detector. In these embodiments, the excitation optical path from the beam splitter arrangement and the detection optical path from the reaction vessels are substantially parallel and not folded.

The Detector Arrangement 142

The near collimated fluorescent light from the sample imaging lens 409 passes the dichroic element 143 and then within a very short space (~3 mm) is incident of the detector arrangement 142. The device may contain one detector arrangement 142 for each reaction vessel in the device. Therefore, a device for analysing the molecule(s) in four reaction vessels for example may contain four detector arrangements. Where the system comprises a plurality of detector arrangements, each detector arrangement is independent of each other. Each detector arrangement 142 is contained in a cylindrical housing which allows for easy removal/installation and modularity. The detector arrangements) 142 is/are connected to sensitive high gain transimpedance type amplifiers or a multiple input channel charge integrating integrated circuit. In an alternative configuration, the device may contain a single detector arrangement for all reaction vessels in the device. The detector arrangement may, for example, comprise a compact CCD camera.

The detector arrangement 142 comprises a silicon photodetector 413. The silicon photodetector 413 is configured to generate an electrical signal proportional to incident light intensity (for further amplification via electrical means). The silicon photodiode 413 may be for example an FDS100 photodiode provided by Thorlabs of Newton, N.J.

The detector arrangement 142 further comprises an imaging lens 414. The imaging lens 414 images/focuses fluorescent light onto the silicon photodiode 413. The imaging lens 414 is preferably an imaging aspheric lens having a focal length f of about 12 mm.

The detector arrangement 142 preferably further comprises a long-pass filter 415 to remove any noise (stray wavelengths) which may be erroneously detected by the photodiode 413, affecting the results of the detection. The long-pass filter may be for example a glass absorbing type long-pass filter with cut-off wavelength of 500 nm. The glass filter is configured to remove off axis (non-collimated) light components and is generally more reliable compared to a dielectric element having a performance that is angle sensitive.

The detector arrangement 142 further comprises a bandpass filter which is arranged to pass a reaction light (which may, for example, be the Sybr Green wavelength) from sample fluorescence. The bandpass filter may be a notch type interference filter with transmission band in the interval 520-560 nm where the dye used is Sybr Green. The filter is included primarily to reject residual excitation light and also light outside of the main sample fluorescence band, including any traces of ambient light. The filter lowers the noise floor of the device and improves signal to noise (S/N). Exemplary variants to this configuration, and alternative types of reporter dyes that can be used in the device and reaction light wavelengths, are described in the Summary of the Invention section above.

The detection optical path B in a device for detection of molecule(s) in a single reaction vessel is folded just once, by the turning mirror 411. The detector assembly 412 is therefore preferably arranged substantially orthogonally in the same plane with respect to the vessel receptacle 110 and turning mirror 411.

The Controller

Figure 9:
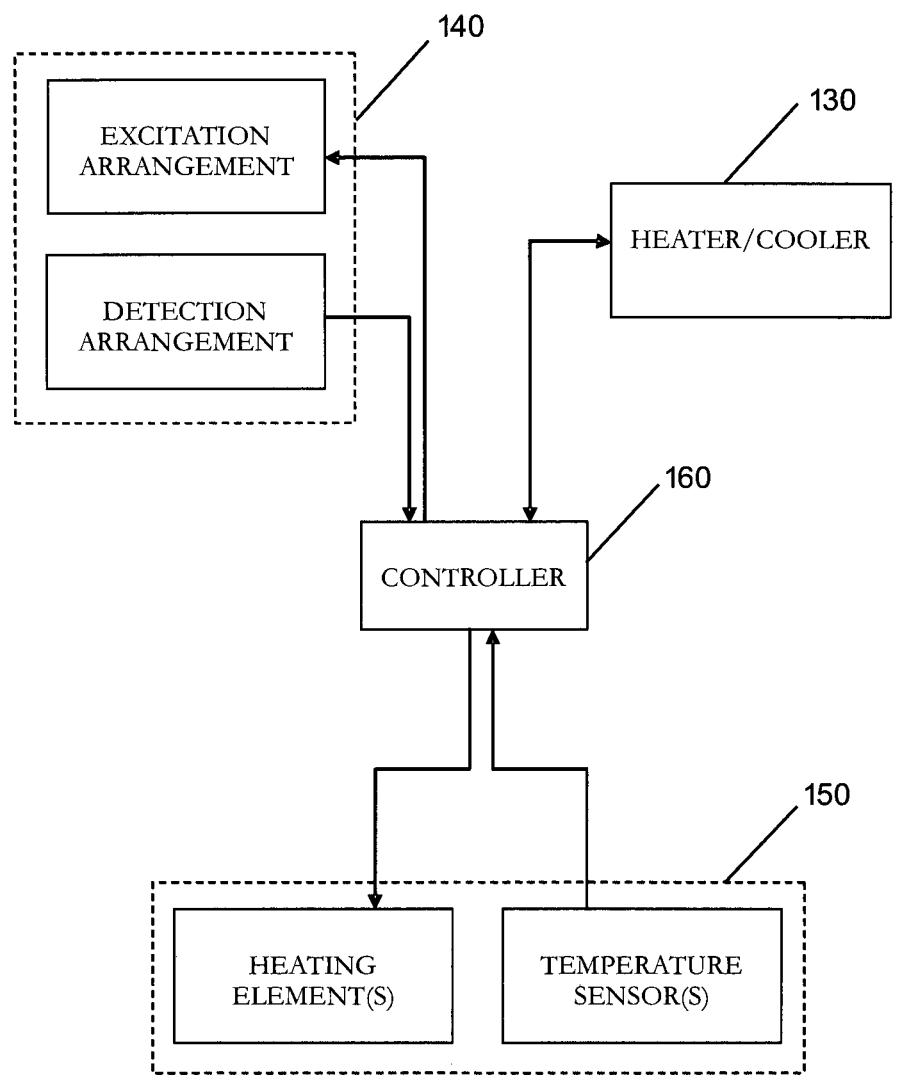
FIG. 9 shows a general block diagram of the interaction between the controller of an embodiment of the present invention and other components of an embodiment of the device.

Referring to FIG. 9, the device of embodiments of the present invention further comprises a controller 160 for controlling various functions of the device. The controller 160 is configured to control with feedback the heater/cooler 130 for heating and/or cooling the reaction vessel(s). The controller 160 is further configured to control the excitation arrangement of the optical assembly 140 to generate the excitation beam(s) for illuminating the sample within the reaction vessel(s). Measurements of the reaction light measured by the detection arrangement(s) of the optical assembly 140 are communicated to the controller 160. Further, where the device comprises a reaction vessel cover heater 150, the controller 160 is configured to control the heating element(s) of the reaction vessel cover heater 150 (which will be discussed in further detail below) and to control the heat output by the heating element(s) of the reaction vessel cover heater 150 based on feedback from the temperature sensor(s) of the reaction vessel cover heater.

The controller 160 is configured to control the temperature profile of the vessel receptacle to heat and cool the sample to various predetermined temperatures for specific periods of time, for example to amplify the nucleic acids in the sample. The required temperatures and periods are known to a person skilled in the relevant art.

The controller 160 is preferably communicatively coupled with the heater/cooler 130 and a temperature sensor (such as a thermistor) associated with the reaction vessel holder to form a closed-loop feedback control system capable of accurately reaching and maintaining the required temperatures. Suitable control methods are known to those skilled in the art, and may comprise a proportional-integral-derivative (PID) control scheme, for example. The controller 160 may be programmed with one or more functions to control the temperature profile of the sample(s) within the reaction vessel(s) accordingly depending on the application of the device. For example, the controller 160 may be pre-programmed with a function to cycle the temperature of the sample(s) for amplification and detection of nucleic acids including Q-PCR applications. Further, the controller 160 may be pre-programmed with additional or alternative functions to maintain the temperature of the sample(s) and/or to increase or decrease the temperature of the sample(s) if the device is used for other applications for detection of molecule(s). The function(s) of the controller may be user-selectable during the run-time of the device.

Figure 10:
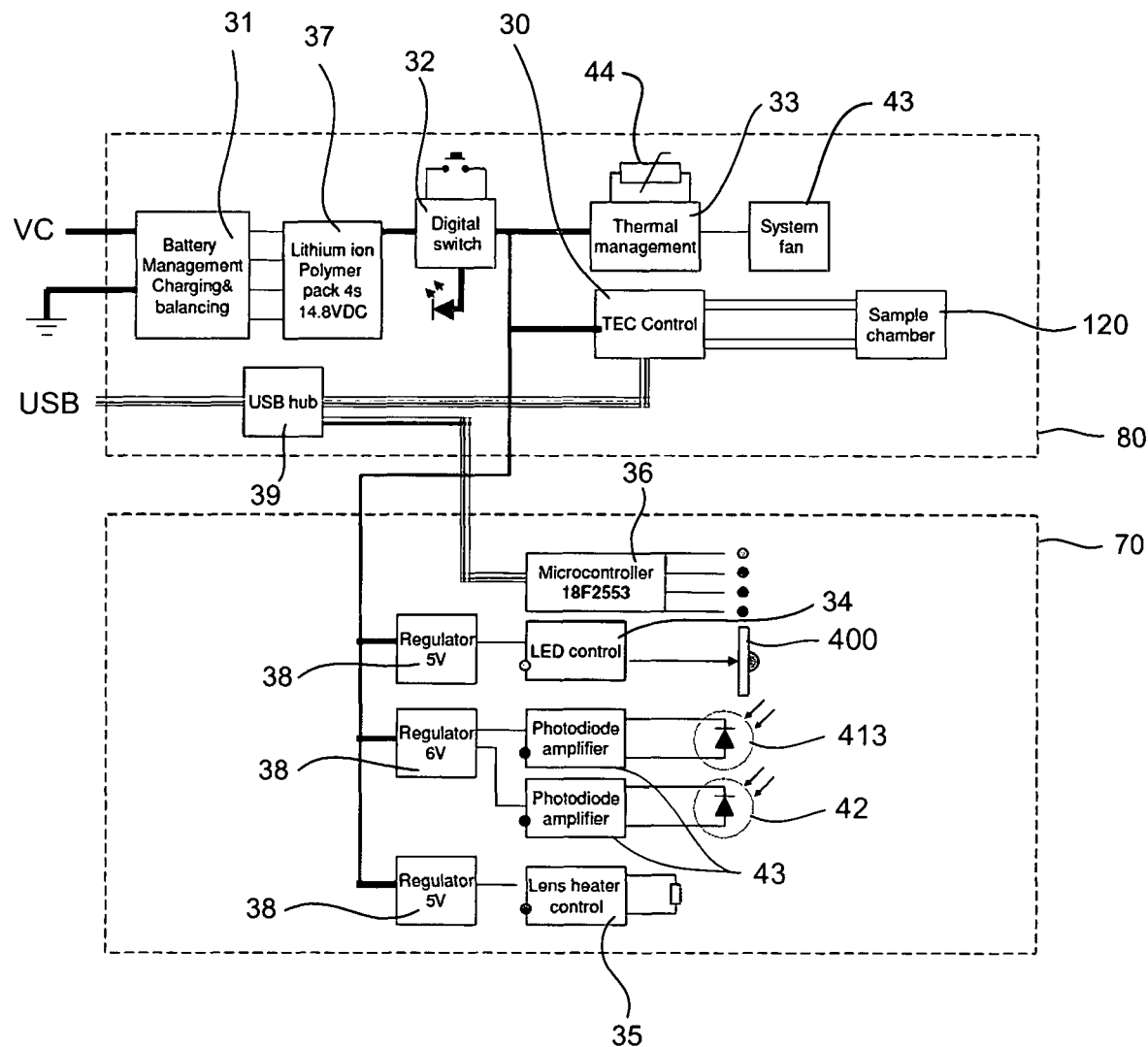
FIG. 10 shows a block diagram of a controller for a device for detecting molecule(s) in a single reaction vessel according to an embodiment of the present invention.

Shown in FIG. 10, the controller 160 preferably includes a battery management module 31 for managing charging of the batteries which may power the device; power switch 32 for turning the device on and/or off; thermal management module 33 for sensing the internal temperature of the apparatus through a thermistor 44 and controlling the system fan 43 to manage the temperature of the device; LED control module 34 for controlling activation of the excitation source 400; and reaction vessel cover heater control module 35 for controlling the temperature of the reaction vessel cover heater; and microcontroller 36.

Microcontroller 36 is electrically and communicatively coupled to the LED control module 34 and lens heater control 35 via digital outputs to selectively activate the excitation means and reaction vessel cover heater. The microcontroller 36 is also electrically and communicatively coupled to two photodiodes—the fluorescence detector photodiode 413 and LED monitor sensor photodiode 42 via analogue inputs to receive an analogue signal indicative of the level of light received by the photodiodes 413, 42. The fluorescence detector photodiode 413 is for receiving the reaction light from the reaction vessel, while the LED monitor sensor photodiode 42 is for monitoring the intensity of the excitation beam. The LED monitor sensor photodiode 42 is used to correct the fluorescence data if necessary and/or may provide a feedback signal to the LED control module 34 to keep the intensity of the excitation beam within a predetermined range. Photodiode amplifiers 43 are provided to provide suitable amplification of the signals detected by the photodiodes 413, 42. An integral analogue to digital converter (ADC) converts those signals to a digital value which is read, stored, and communicated by the microcontroller to an external device via a USB or other suitable interface.

The functions of the controller 160 are distributed among a number of integrated circuits of the embedded system, such as the TEC control 30, battery management module 31, thermal management module 33, LED control module 34, lens heater control module 35, and microcontroller 36.

It will be appreciated by those skilled in the art that the controller according to the embodiments of the present invention may be implemented purely in hardware consisting of one or more components which may include discrete electronic components or integrated circuits. Alternatively, or additionally, the controller of embodiments of the present invention may be implemented at least in part using programmable hardware components, such as programmable logic devices (PLDs) or field programmable gate arrays (FPGAs), or by software executed by a computing means or processor which may include the microcontroller or a general purpose personal computer (PC) programmed accordingly. Typically, however, the invention would be implemented as an embedded system using a combination of the aforementioned components, as described with respect to the preferred embodiment of the invention. In particular, the functions of the controller are preferably distributed among a number of integrated circuits of the embedded system, such as the TEC control, battery management module, thermal management module, LED control module, lens heater control module, and microcontroller, for example, but may alternatively be performed centrally by a single integrated or discrete circuit (such as microcontroller) without departing from the scope of the invention.

Power Supply

Since the preferred embodiment of the invention is portable and adapted for use in the field, it is preferably battery-powered. The device (in particular the low thermal mass of the vessel receptacle) is therefore designed specifically to maximise power efficiency and prolong battery life.

Referring to FIG. 10, the battery power source 37 may comprise a series of four 3.7 V to 4.2 V single cell lithium ion batteries (flat pack format) for a nominal voltage of 14.8 V (3.7 V×4). Alternatively, the battery power source 37 may comprise electrically parallel inter-connected lithium-ion cells for a 3.0 V to 4.2 V nominal operating range (discharged to fully-charged). A boost converter may be used to provide a stable operating voltage of 5 V from which all subsystems are powered. The boost converter is compact, safe and efficient. The apparatus may further comprise a plurality of high-efficiency voltage regulators 38 providing a regulated power supply of the correct voltage to the various electronic components of the apparatus.

The device preferably also includes a power socket 82 (shown in FIG. 12) adapted to receive external power VC (preferably a 20 V DC input) to operate the device and/or to recharge the battery power source 37. Alternatively, the external power source may be a 5V DC source when the battery power source comprises parallel inter-connected lithium-ion cells for a 3.0 V to 4.2 V nominal operating range. The power socket 82 preferably provides a magnetic coupling with a power supply cable in order to permit a high charge current of about 5 Amps to the device. In another embodiment, the power socket 82 is a standard high amperage two terminal (centre positive) power jack.

The Component Layout

The device of one embodiment of the present invention comprises an upper casing 70 (shown in FIG. 11) and a lower casing 80 (shown in FIG. 12). The device shown in FIGS. 11 and 12 show a device for amplification and detection of molecule(s) in a single reaction vessel.

The lower casing 80 is engageable with the upper casing 70 such that the device has a closed configuration and an open configuration. In the closed configuration, the upper casing 70 covers the reaction vessel in the lower casing 80 and molecule detection of the sample within the reaction vessel can take place. In the open configuration, the reaction vessel can be placed into or removed from the lower casing 80.

The upper casing 70 slidably engages the lower casing 80. However, any other form of suitable engagement may be implemented between the lower casing 80 and the upper casing 70. For example, the upper casing 70 may be connected to the lower casing 80 via a hinge so that the upper casing 70 is pivotable relative to the lower casing 80 about the hinge. Alternatively, the upper casing 70 may be detachable from the lower casing 80, and the upper casing 70 engages the lower casing 80 in a clip-on engagement. However, the sliding arrangement is preferred, as the other configurations result in the internals and umbilical cabling being extensively exposed to the environment and natural light, and difficulties can be encountered with achieving correct alignment of the optics and balancing of the device. In an alternate arrangement, the umbilical cabling is replaced by sprung sliding electrical interconnects which allow complete and un-tethered separation of the upper casing 70 and lower casing 80.

Referring to FIG. 11, the upper casing 70 houses the optical assembly for detection of the sample(s) in the lower casing 80 of the device. The upper casing 70 houses the excitation lamp assembly 407, detector head assembly 408, and detector assembly 412, steering mirrors 71, optical aperture 405, and optionally additional filter(s) 73 which were previously discussed. The upper casing 70 may also house the regulators 38, microcontroller 36 and associated printed circuit board (PCB), and a LED driver circuit 72.

As shown in FIG. 11, the excitation source, collimating lens 403, and clean-up filter 404 are integrated in an excitation lamp assembly 407. The shroud and dichroic mirror are integrated in the detector head assembly 408. The detector head assembly 408 is preferably aligned, in use, directly above the sample chamber 110 with a focusing/imaging lens 409 having a focal length of 12 mm substantially adjacent the lid of the reaction vessel in use.

Referring to FIG. 12, the lower casing 80 contains the reaction vessel holder 120 which is arranged to hold the reaction vessel. As shown in the figure, the reaction vessel holder 120 is placed substantially at an end within the lower casing 80. However, it should be appreciated that the reaction vessel holder 120 may be placed anywhere within the lower casing 80, for example in the center of the lower casing 80. The lower casing 80 further houses the heater/cooler which comprises the thermoelectric cooling (TEC) device 131 for heating the reaction vessel 110 held by the reaction vessel holder 120, and a heat sink 132 and/or a fan 81 for cooling the heat sink 132. The lower casing 80 further comprises the digital power switch circuit 32, USB interface circuit 39, battery management module 31, TEC control module 30, power switch 83, system light 84, and power socket 82.

The upper casing 70 and lower casing 80 are formed of a metallic material having a relatively high thermal conductivity, typically less than that of the heat sink and/or vessel receptacle for cost and/or weight reasons, but significantly higher than the insulative material of the reaction vessel holder 120. Suitable materials may include materials which have a thermal conductivity in the range of about 12 $Wm^{-1}K^{-1}$ and 240 $Wm^{-1}K^{-1}$ such as stainless steel or aluminium for example.

The upper and lower casings are preferably of a substantially similar size. In one embodiment, the dimensions (length×width×height) of the upper casing 70 are L=109 mm×W=68 mm×H=47 mm, and the dimensions of the lower casing 80 are L=109 mm×W=68 mm×H=59 mm.

Example Embodiments of Portable Device for Detection of Molecule(s) in a Plurality of Reaction Vessels According to preferred embodiments of the present invention, the device can be used for detection of molecule(s) within a plurality of reaction vessels. Implementation of such a device will be discussed in detail below with reference to FIGS. 13 to 35. In the following description of the embodiments for a plurality of reaction vessels, parts having like reference numerals as those used in the previous section with the addition of a prime ('), or a double prime ("), or a triple prime ('") indicate like parts. Unless stated otherwise, these like parts operate substantially in a similar manner to that described above.

First, second and third example embodiments of the device will be described in detail below. It should be understood that the invention is not limited to the two embodiments described below. Combinations of different features from the different example embodiments may be possible and are within the scope of the invention. For example, third example embodiments of the device may comprise the reaction vessel holder, the heater/cooler, and the controller of the first example embodiments and the optical assembly of the second example embodiments.

First Example Embodiments of the Device

The Reaction Vessel Holder

Figure 13:
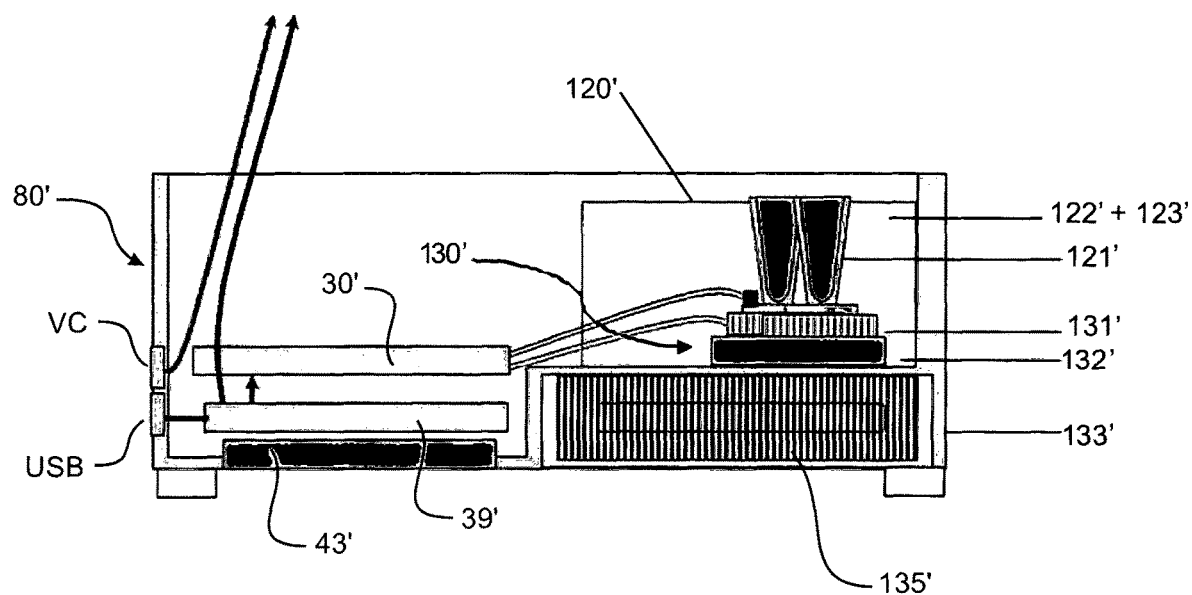
FIG. 13 shows a side view of a lower casing of the device for detecting molecule(s) in four reaction vessels according to first example embodiments of the present invention.

Referring to FIG. 13, the device comprises a lower casing 80'. The lower casing 80' houses the reaction vessel holder 120' and the heater/cooler 130'. The reaction vessel holder 120' comprises four vessel receptacles 121', each vessel receptacle being arranged to receive a respective one of the reaction vessels.

The reaction vessels holder 120' comprises a housing 122' which houses the vessel receptacles 121' and an insulative material 123' such as aerogel or any other suitable materials described above (or alternatively an air gap) which substantially fills the space between the vessel receptacles 121' and the housing 122'.

The Heater/Cooler

Referring again to FIG. 13, the heater/cooler 130' comprises three TEC devices 131', two of which are shown in FIG. 13. The TEC devices 131' are thermally coupled to four vessel receptacles 121'.

The TEC devices 131' physically contact a plate 132' made of a substantially thermally conductive material, such as those described previously. In one embodiment, the plate 132' comprises copper. The plate 132' has a surface area of about two times that of the TEC devices, to facilitate heat transfer to and from the TEC devices.

The metallic casing of the device functions as a heat sink 133', part of which is positioned below the plate 132'. A grille type heat sink and/or fan 135' is separated from (while still being in thermal communication with) the plate 132' by a partition which forms part of the lower casing. The partition is a thermally conductive material.

A TEC control module 30' is coupled to the TEC devices 131' for controlling the heat output by these devices 131'. The TEC control module is further coupled to the vessel receptacles 121' to measure the temperature of the receptacles 121'. The TEC control module 30' is further coupled to a USB hub or interface circuit 39'. A system fan 43' for cooling the components of the device.

Three TEC devices 131' are used in parallel thermally in order to obtain the desired heat pumping capacity. Each TEC is two stage, in order that a maximum temperature differential of about 140° C. can be achieved across the TEC devices from the 'hot' side (the vessel receptacle side) to the 'cold' side (the heat sink side). Two stage elements are required if the ambient temperature is below about 25° C. as the samples may need to be cycled to about 95° C. and single stage TEC devices can typically generate up to 70° C. difference between the hot and cold sides. The vessel receptacles are thermally coupled to the 'hot' face of the TEC elements.

The vessel receptacles 121' are each thermally continuous in order to ensure that the temperature gradient throughout each vessel receptacle is close to zero at all times in order to ensure that each sample sees the same temperature at any given moment. The base 1213 of each vessel receptacle 121' interfaces with the parallel arrangement of TEC devices 131' via a thin and flat section of plate of suitable material of high thermal conductivity, such as copper for example. The vessel receptacles 121' are pressed and soldered into that plate. The vessel receptacles 121' are clamped firmly to the TEC devices below via non conductive screws which locate into the copper heat transfer plate 132'.

The vessel receptacles 121' and TEC assembly are shrouded in the housing 122' which allows only the open mouths of the vessel receptacles to protrude for reaction vessel 110 insertion. The housing thermally insulates the vessel receptacles from the casing and limits convection from the vessel receptacles. Teflon sleeves (not shown) are used to hold the exterior of the vessel holder mouths concentric within matching holes in the housing 122'. As described above in relation to FIG. 3, the housing 122' will be made of a suitable material. In one embodiment, the material is nylon or a similar material, which has a low coefficient of thermal expansion. However, Teflon may be used for the sleeves as the thin cross section is inconsequential in this configuration and the thermal conductivity of Teflon is substantially similar to that of nylon. The Teflon sleeves will limit the heat losses from the vessel receptacles to the housing via conduction, by providing a small contact area.

The Optical Assembly

Figure 14:
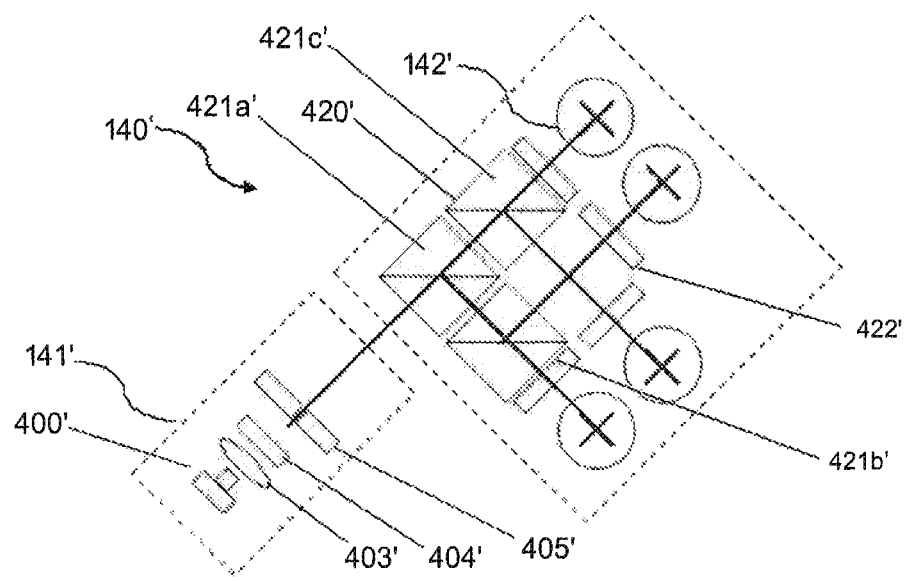
FIG. 14 shows a schematic general beam splitter arrangement of the device according to the first example embodiments of the present invention.
Figure 15:
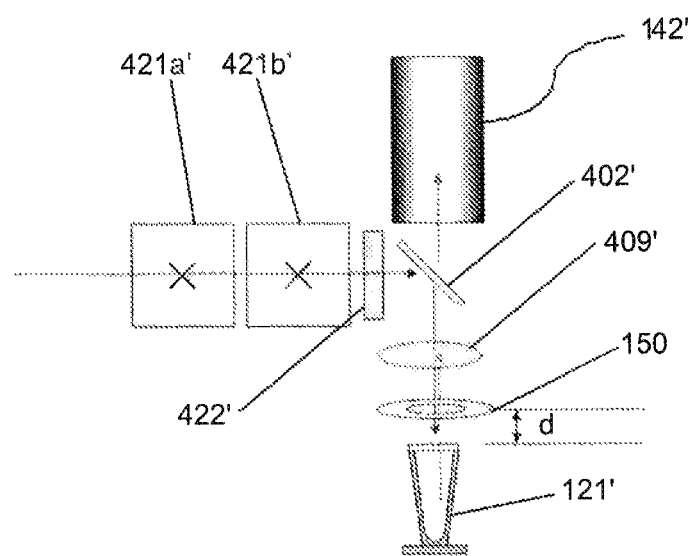
FIG. 15 shows a schematic four-channel beam splitter arrangement of the device according to the first example embodiments of the present invention.

FIGS. 14 and 15 show the optical assembly 140' of this embodiment of the present invention.

The excitation source 400' used in the excitation arrangement is a Nichia laser diode. The laser diode is configured to emit an excitation beam having a suitable wavelength such as 470 nm for example. The laser diode is the sole excitation source in the device. At a wavelength of 470 nm, the excitation source 400' is configured to generate an excitation beam with a narrow band (~1 nm) light. The excitation arrangement may alternatively comprise a plurality of excitation sources, as previously described, where the excitation arrangement is configured to generate an excitation beam having a plurality of excitation wavelengths.

The excitation arrangement 141' is similar to the previously described excitation arrangement. The excitation beam from the excitation source 400' passes through a collimating lens 403' which collimates the excitation beam. The collimated excitation beam is passed through first a neutral density filter 404' and then a laser line clean-up interference filter. The excitation beam is then passed through a 2 mm diameter optical aperture 405'.

The excitation beam then goes through a beam splitter arrangement 420' for splitting the excitation beam. The beam splitter arrangement 420' comprises one or more beam splitters for splitting the excitation beam.

A beam splitter is defined as an optical element that receives one input beam and 'splits' it to two components. One beam splitter cannot produce more than two beams from a single incoming beam without additional optical elements (mirrors, corner cubes and other reflective elements). There exist other optical elements (dispersive elements such as prism and diffraction grating) which can split a single monochromatic beam into a plurality of beams (zeroth, first, second order and so on). These are dispersive elements and not beam splitters in the context of the specification. A grating is not suitable for the embodiment device of the present invention for spatial and intensity purposes (the zeroth, first, second, third and higher order beams all have different power from a grating). In some embodiments, the beam splitter may be configured to split selected beams but not others. For example, the beam splitter may be configured to split beams at the excitation wavelength(s) and allow beams at other wavelengths to pass.

In an alternative embodiment, two or more beam splitters in the beam splitter arrangement are together a monolithic optical component. Optical index matching material is used to fill interstitial air gaps and to fuse together adjacent beam splitters in the monolithic optical component. The monolithic optical component can be assembled from a plurality of pieces of optical material of the required geometry (for example trapezoidal and/or right angle parts. An example of a monolithic component will be described by way of example with reference to the second example embodiments of the device in FIGS. 27a and 27b.

Where two or more reaction vessels are present in the first example embodiments of the device, the beam splitter arrangement comprises one or more beam splitters configured to split the excitation beam from the collimator into a plurality split excitation beams. In general, according to the first example embodiments, a device for m number of reaction vessels, m being an integer greater than one, comprises at least m−1 number of beam splitters, which are each arranged to receive a single excitation beam and to split the excitation beam from the collimator into m number of split excitation beams. Accordingly, one beam splitter is required to split an incoming excitation beam to produce two split excitation beams, three beam splitters are required to produce four split excitation beams, and ten beam splitters are required to produce eleven split excitation beams. The beam splitter arrangement would preferably have up to ten beam splitters.

Where the beam splitter arrangement comprises more than one beam splitter, the beam splitters are arranged in tiers such that a first tier comprises one beam splitter for receiving the excitation beam from the collimator, and each of the other tiers comprises one or more beam splitters, each beam splitter in one of the other tiers being configured to receive a split excitation beam from a previous tier.

Figure 16:
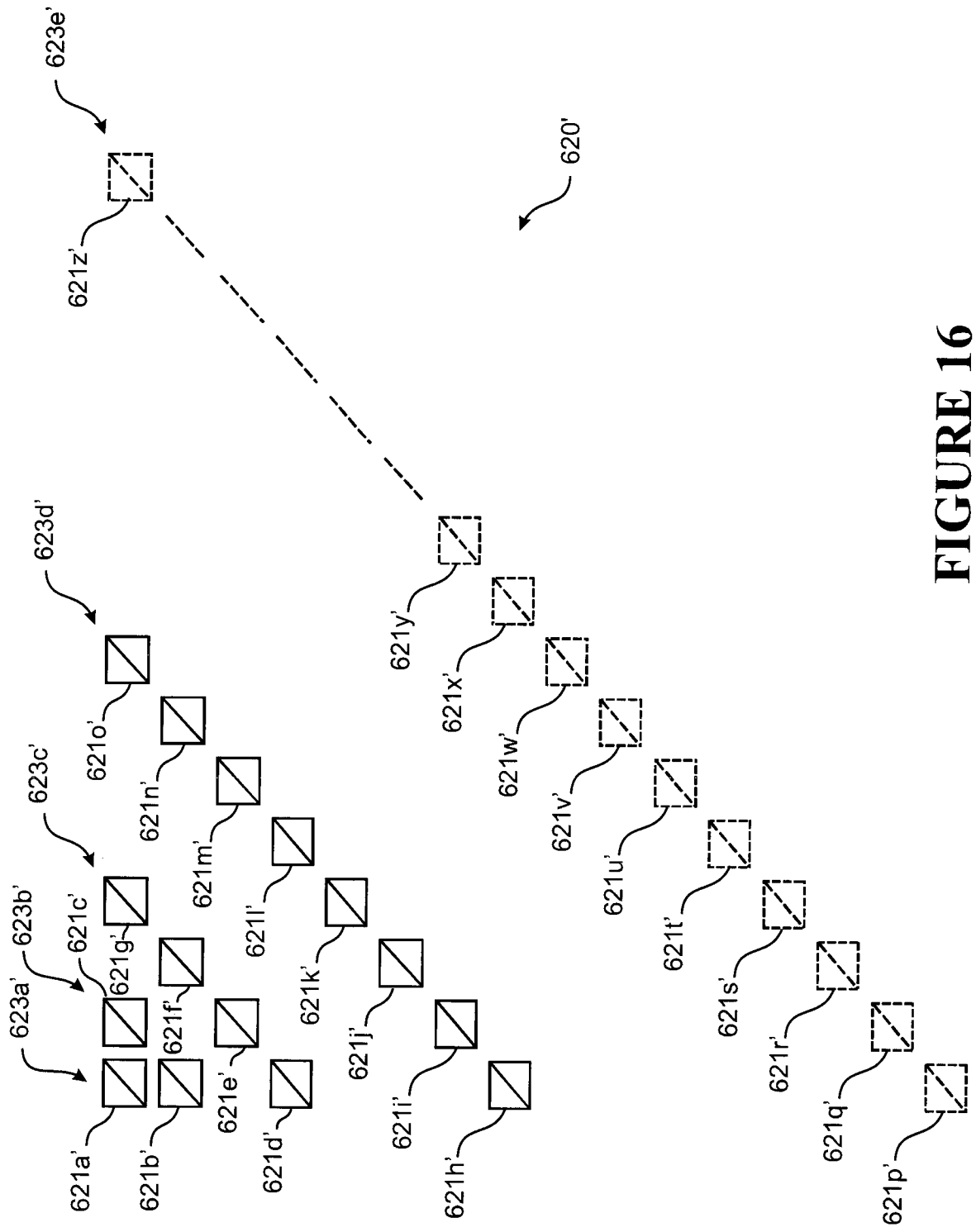
FIG. 16 shows a schematic general beam splitter arrangement of the device according to first example embodiments of the present invention.

Referring to FIG. 16, in one arrangement of beam splitters where more than one reaction vessel or $2^n$ reaction vessels are present in the device (n being an integer greater than zero), the beam splitter arrangement 620' comprises $2^n-1$ number of beam splitters 621$a$'-$z$' and may be arranged in a balanced tier configuration to split the single excitation beam into $2^n$ number of split excitation beams of substantially equal intensity and wavelength, n being an integer greater than zero. In an unbalanced tier configuration where the arrangement of beam splitters do not produce split excitation beams having substantially equal intensity, linear polarisers or neutral density filters could be used at the output(s) of the beam splitter arrangement to substantially equalise the intensity of the different split excitation beams.

In a balanced tier configuration where more than one reaction vessel are present, the beam splitter arrangement 620' has $2^n-1$ number of beam splitters 621$a$'-$z$', each beam splitter adapted to receive a single excitation beam and to split the excitation beam from the collimator into $2^n$ number of split excitation beams of substantially equal intensity and wavelength, n being an integer greater than zero and the number of reaction vessels in the device are less than or equal to $2^n$. In that configuration, the beam splitters 621$a$'-$z$' are arranged in n number of tiers 623$a$'-623$e$' such that a first tier 623$a$' contains one beam splitter 621$a$' for receiving the excitation beam from the collimator, a second tier 623$b$' contains two beam splitters 621$b$'-$c$' for receiving the excitation beams from the first tier 623$a$', a third tier 623$c$' contains four beam splitters 623$d$'-$g$' for receiving the excitation beams from the second tier 623$b$', a fourth tier 623$d$' contains eight beam splitters 623$h$'-$o$' for receiving the excitation beams from the third tier 623$c$', and an $n^{th}$ tier 623$e$' contains $2^{n-1}$ beam splitters 623$p$'-$z$' for receiving excitation beams from the n-$1^{th}$ tier. For beam splitter arrangements with more than one tier, each beam splitter in a tier is associated with two respective beam splitters in a next tier such that two beams split by a respective beam splitter in a tier are split further into four beams by the associated beam splitters in the next tier. Each reaction vessel is associated with a split excitation beam from the beam splitter arrangement.

Figure 17:
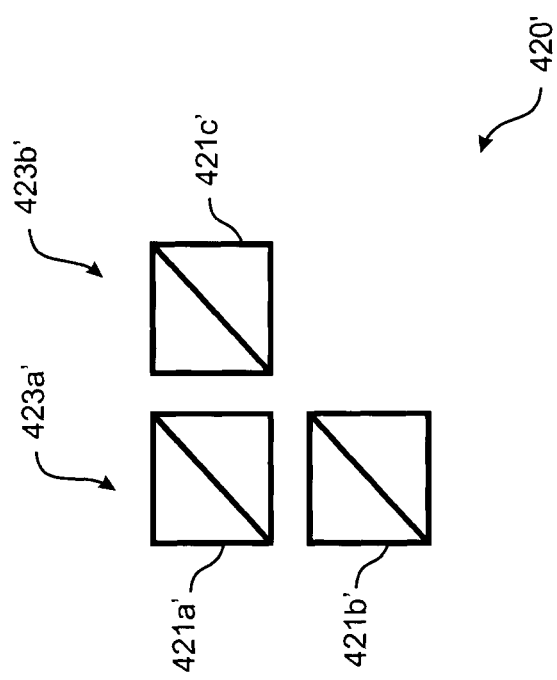
FIG. 17 shows a schematic four-channel beam splitter arrangement of the device according to first example embodiments of the present invention.
Figure 18:
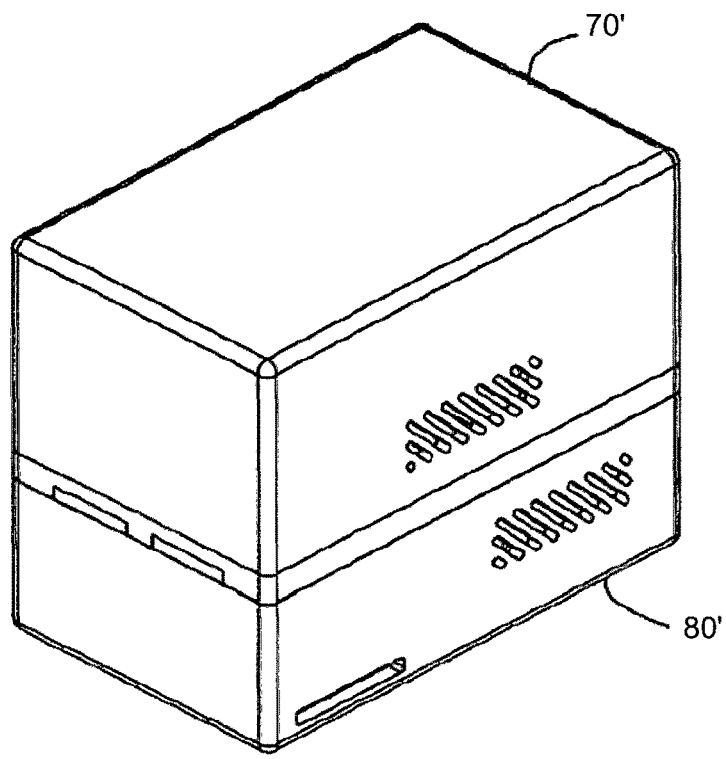
FIG. 18 shows a perspective view of the device of first example embodiments of the present invention in a closed configuration.
Figure 19:
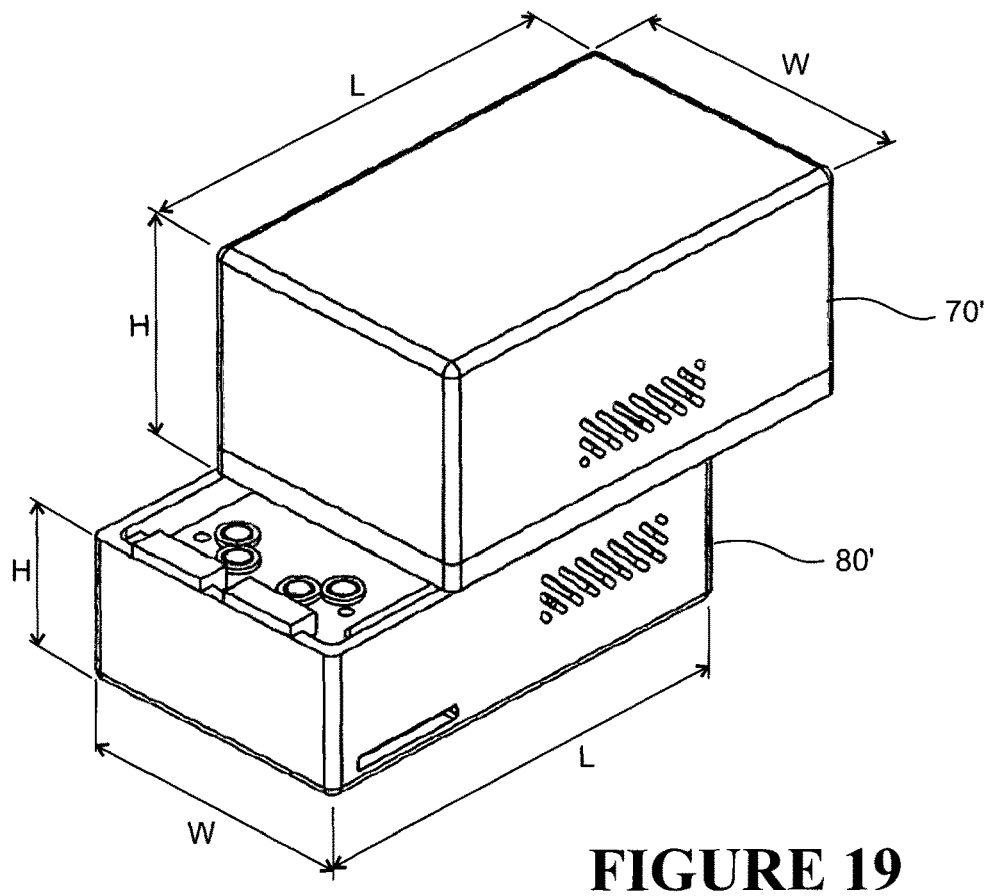
FIG. 19 shows a perspective view of the device shown in FIG. 18 in an open configuration.

FIG. 17 shows an example of a two-tier beam splitter arrangement 420' for a four-channel device shown in FIGS. 14 and 15. The beam splitter arrangement 420' comprises a first tier 423$a$' having one beam splitter 421$a$', and a second tier 423$b$' having two beam splitters 421$b$'-$c$'. The beam splitters 421$b$'-$c$' in the second tier 423$b$' are configured to receive the excitation beams from the beam splitter 421$a$' in the first tier 423$a$'.

FIG. 14 shows an example of a two-tier beam splitter arrangement having a balanced tier configuration. The beam splitter arrangement 420' comprises three cube beam splitters 421$a$'-$c$' for splitting the excitation beam from the excitation source 400' into four split excitation beams. The arrangement of beam splitters is similar to the arrangement shown in FIG. 17. The first tier (which receives the excitation beam from the excitation arrangement) contains a single beam splitter 421$a$'. The second tier contains two cube beam splitters 421$b$'-$c$', each of which receives a beam split by the cube beam splitter 421$a$' in the first tier. The geometry of cube beam splitters in this configuration is compact, robust and simple to align. Cube beam splitter or plate beam splitters could be used in the beam splitter arrangement of the preferred embodiment device. A cube beam splitter is configured to receive a single beam or a plurality of spaced apart beams, and to split the or each beam into two split beams, each split beam having substantially the same or different intensities. In the embodiments described below, a cube beam splitter typically receives a single beam and splits the beam into two split beams. A plate beam splitter is configured to receive one beam or a plurality of spaced apart beams, and to split the or each beam into two split beams, each split beam having substantially the same or different intensities. For the first example embodiments of the device, cube beam splitters are preferred to plate beam splitters as they are more compact/robust and simpler to align. The other key advantage is only one reflection is produced from each internal beam splitting interface, producing clean beams with no secondary ghosting. Where a beam splitter arrangement comprises more than one beam splitter, one or more plate beam splitters could be used to replace two or more beam splitters in the beam splitter arrangement. For example, where a tier of a beam splitter arrangement comprises four beam splitters, two, three, or all of the beam splitters in that tier could be replaced by a single plate beam splitter.

The cube beam splitter arrangement 420' may comprise a polarising cube beam splitter or non-polarising cube beam splitters. Where the arrangement 420' comprises a polarising cube beam splitter, the excitation beam entering the polarising cube beam splitter is first passed through a half wave plate, before being incident onto the polarising cube beam splitter. A polarising cube beam splitter is capable of splitting the excitation beam equally into two split excitation beams. Alternatively, a half wave plate may not be provided, and the polarising beam splitter or the excitation source may be rotated accordingly such that the excitation beam to the polarising beam splitter is split into two beams of substantially equal or unequal intensities. The non-polarising beam splitters can be designed to be wavelength and polarisation independent to produce to split beams of substantially equal intensities (to within about 5%). The beam splitter arrangement may comprise a combination of at least one half-wave plate, at least one polarising cube beam splitter, and at least one non-polarising cube beam splitter. Preferably, in the case where n is more than one, the cube beam splitter in the first tier comprises a half-wave plate and an associated polarising cube beam splitter, and the cube beam splitters in the other tiers are non-polarising beam splitters.

Each beam is passed through a linear polarizer 422' before being reflected through 90° by the dichroic element 402'. In one embodiment, the dichroic element 402' is highly reflective at 473 nm and highly transmissive at wavelengths greater than 500 nm. As described herein, where a plurality of excitation wavelengths are used or where the reaction light comprises multiple reaction light wavelengths, the dichroic element may be replaced by a suitable multi-transition interference filter element, such as a trichroic element, a notch filter, or a multi-bandpass filter for example. An example of a suitable multi-transition interference filter may for example be a BrightLine® triple-band bandpass filter. The multi-transition interference filter is an interference filter that may be used to block or reflect two wavelengths while being transmissive for a different wavelength. Each excitation beam is sent through an imaging/collimating lens 409' which focuses the excitation beam into the reaction vessel held in each reaction chamber. The reaction light emitted from the fluorescent volume formed in the sample at the laser beam focus is then collimated by the former imaging/collimating lens 409'. The collimated light passes through the dichroic element 402' and onto the detector arrangement 142'. As previously described, the detector arrangement 142' is comprised (optically) of first a bandpass interference filter in the green portion of the spectrum in the case where the fluorescent marker is SYBR Green (or generally in the spectrum of the reaction light) followed by an absorbing glass type filter and finally an additional compound filter (absorbing glass and an interference filter) intended to make sure no residual excitation is present. Depending on the nature of the application of the device, the light is then imaged by a spherical or aspherical lens onto a silicon photodiode.

A reaction vessel cover heater 150 is provided between the vessel receptacle 121' and the imaging/collimating lens 409'. Features and function of the lens heater will be described in further detail below. The lens heater 150 is spaced from the vessel receptacle by a distance d of about 2 mm.

Casing

FIGS. 18 to 22 show a device for detecting molecule(s) in four reaction vessels. The device comprises an upper casing 70' and a lower casing 80'. The upper casing 70' is slidable relative to the lower casing 80' between a closed configuration (shown in FIG. 18) and an open configuration (shown in FIG. 19).

Figure 20:
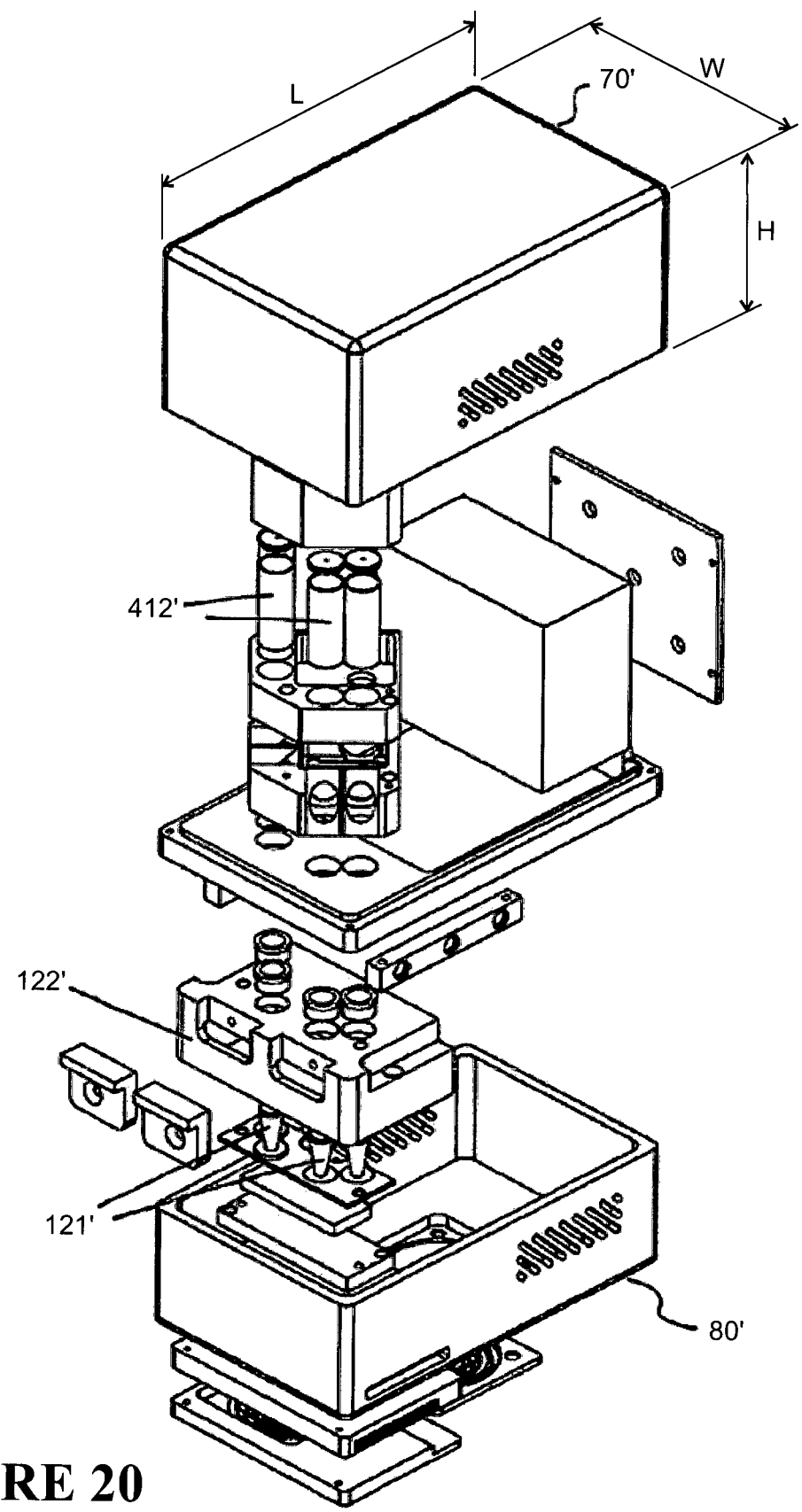
FIG. 20 shows an exploded perspective view of the device shown in FIG. 18.

FIG. 20 shows an exploded perspective view of the device when the device is in the closed configuration. In that configuration, each detector arrangement 412' which is housed within the upper casing 70' has a straight line of sight into a respective one of the vessel receptacles 121' housed within the lower casing 80'.

Figure 21:
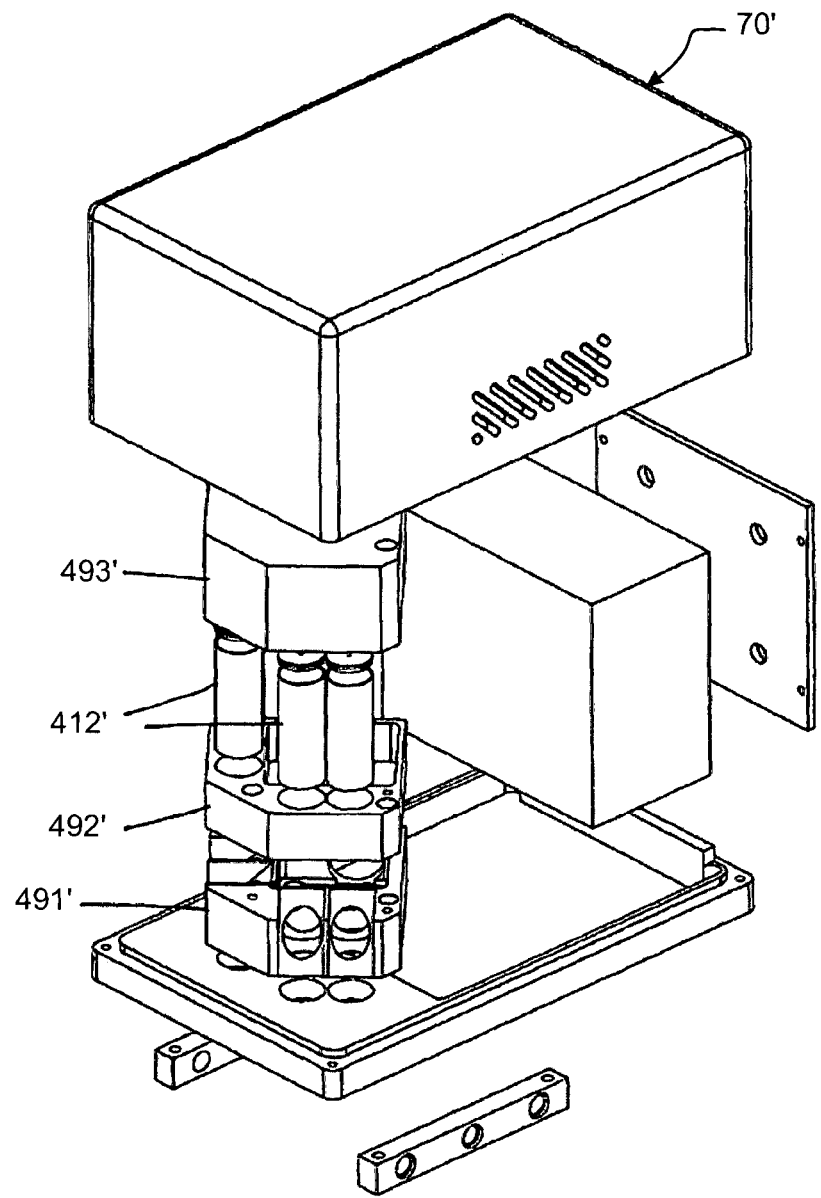
FIG. 21 shows an exploded perspective view of an upper casing and components of the device shown in FIG. 18.

FIG. 21 shows an exploded perspective view of just the upper casing 70'. The upper casing 70' houses the optical assembly. Part of the optical assembly is housed within a tower arrangement comprising a lower section 491', a mid-section 492', and an upper section 493'. The detector assembly 412' and associated electronics are housed within the mid-section 492' of the tower. The lower section 491' of the tower comprises the beam splitter arrangement and the dichroic elements of the optical assembly. The upper section 493' is a cap for mid-section 492'. The lower section 491' has a series of exterior walls, each wall having an aperture and being at an angle of about 45° to the normal. The beam splitter is configured to direct excitation beam through the aperture in these walls. The dichroic elements are configured to rest on these angled walls to thereby reflect an excitation beam from the beam splitter arrangement within the lower section 491' downwards towards the vessel receptacles 121' in the lower casing 80'.

Figure 22:
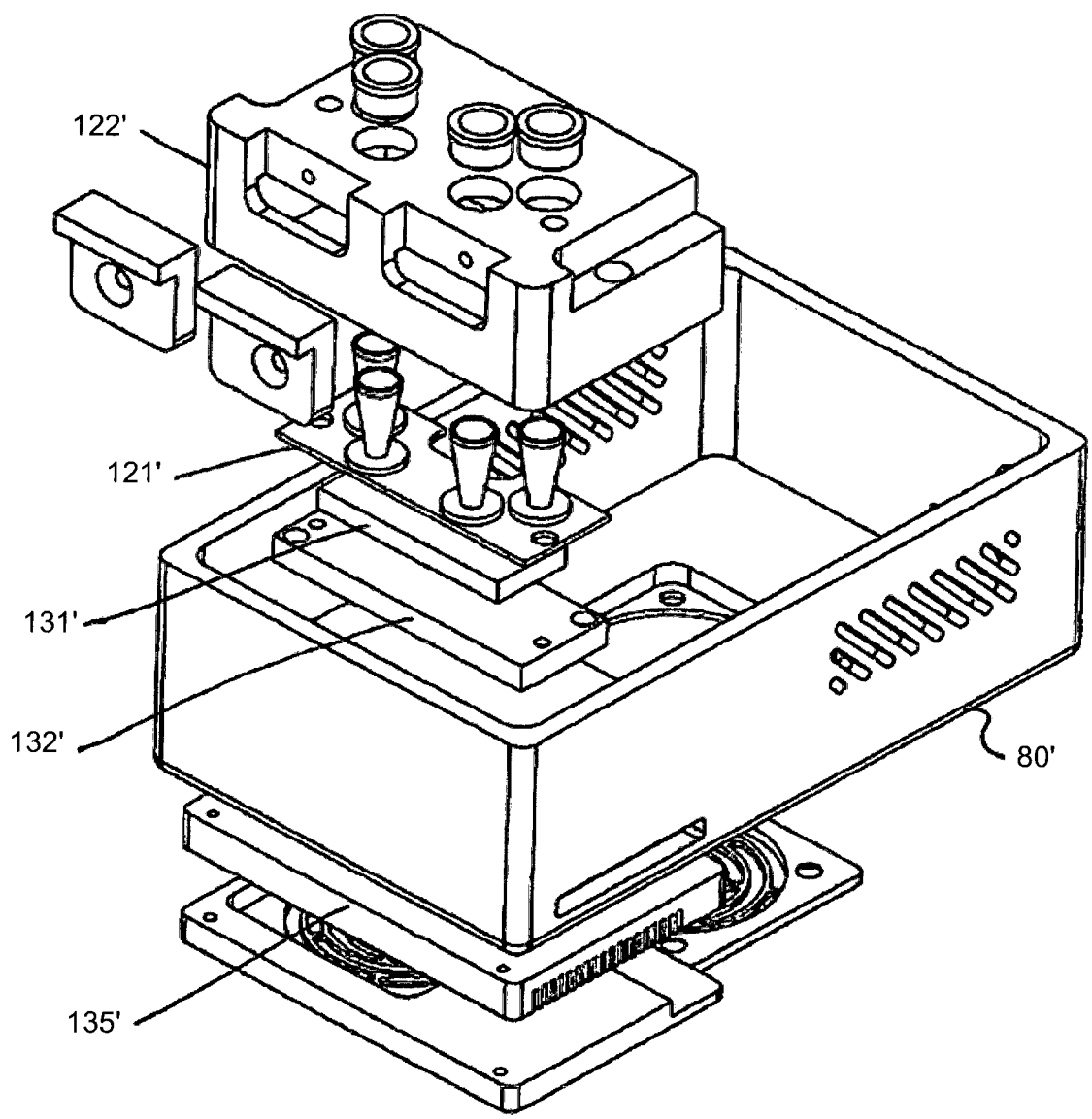
FIG. 22 shows an exploded perspective view of a lower casing and components of the device shown in FIG. 18.

FIG. 22 shows a perspective exploded view of the lower casing 80'. The lower casing 80' houses the reaction vessel holder which includes the vessel receptacles 121', Teflon or Nylon housing 122', the TEC device(s) 131' of which only one is shown, grille-type heat-sink 135' through which air from an integral fan can pass, and the copper heat transfer plate 132' which connects the TEC device 131' to the chassis of the lower casing 80'. The reaction vessels holder is positioned at an end of the lower casing 80'. However, in some embodiments, the reaction vessels holder may be positioned in for example the center of the lower casing 80'.

In one embodiment, the dimensions (length×width×height) of the upper casing 70' are L=134 mm×W=83 mm×H=68 mm, and the dimensions of the lower casing 80' are L=134 mm×W=83 mm×H=42 mm.

Controller

Figure 23:
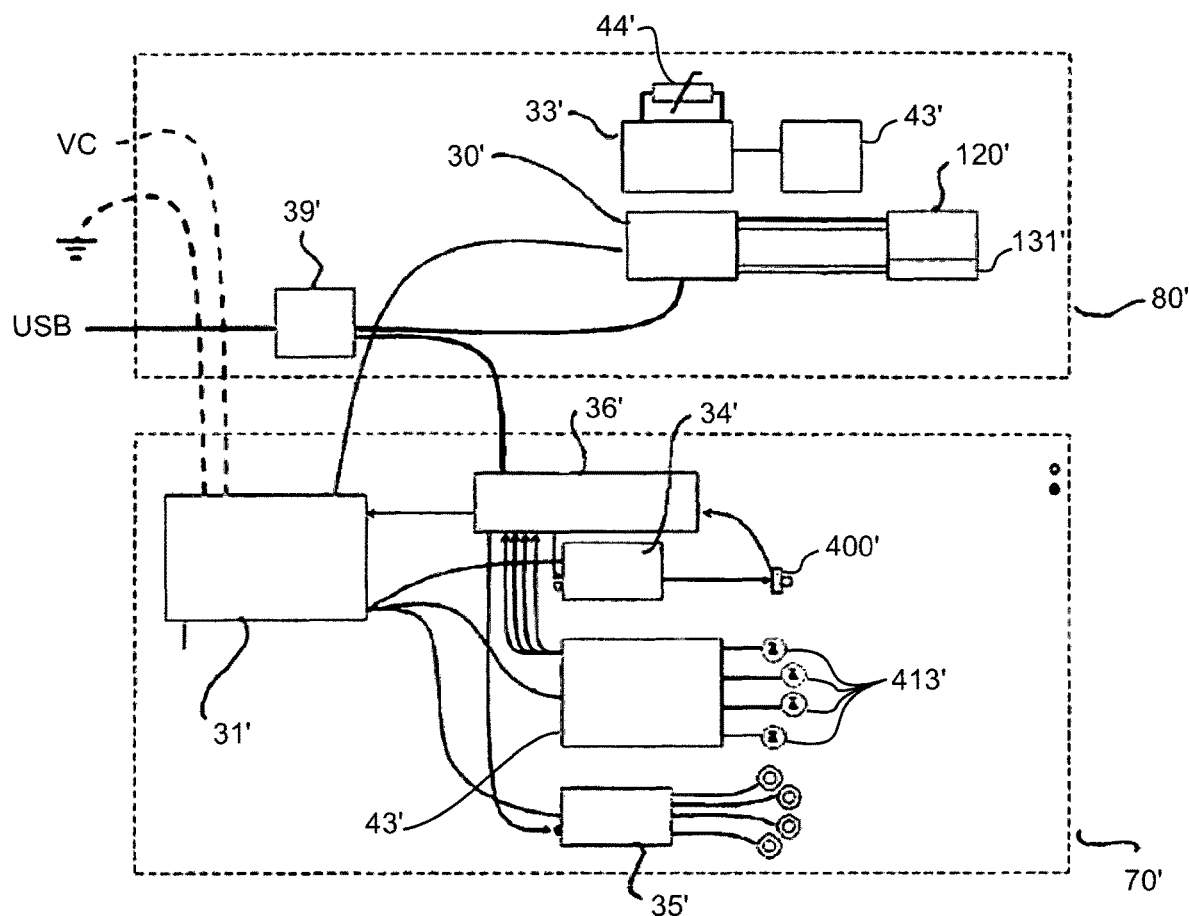
FIG. 23 shows a block diagram of a controller for a device for detecting molecule(s) in four reaction vessels according to first example embodiments of the present invention.

Referring to FIG. 23, the controller for controlling the operation of the device for amplification and detection of samples from four reaction vessels is substantially the same as the controller previously described with reference to the embodiment shown in FIG. 10.

The upper casing 70' comprises the excitation source control module 34', microcontroller 36', detector module 43', and lens heater control module 35'. The excitation source control module 34' is coupled to the excitation source 400'. The excitation source 400' is configured to provide a feedback signal to the microcontroller 36' for adjustment of the excitation beam parameters from the excitation source 400'. The detector module 43' is coupled to the photodetectors 413', and is adapted to power the photodetectors 413', amplify the signal from the photodetectors 413' and buffer the signal if necessary. Unlike the previously described embodiment of the controller, the battery module 31' is now housed in the upper casing 70'. The battery module 31' may be a 4.2V Lithium ion battery, with a boost converter to provide a 5V output voltage for example.

The lower casing 80' comprises the TEC control module 30', the thermal management module 33', the digital switch 32', and the USB hub 39'. In other embodiments of the device, the digital switch is provided in the upper casing and is integrated in the battery or power supply unit pack. The thermal management module 33' is coupled to a case thermistor 44' for measuring a temperature of the device and a system fan 43' for adjusting the temperature of the device accordingly. The TEC control module 30' is electrically connected to the TEC device 131' which is coupled to the sample chambers 120', The lower casing 80' further comprises a port for receiving a voltage VC for charging the battery module 31', and a USB port. The common electrical ground for the device and port for receiving voltage VC are integral to the power jack of the device.

The functions of each of these modules have been discussed previously with reference to the embodiment shown in FIG. 10. The operation of these modules for the embodiment shown in FIG. 23 is substantially the same as the functions of the corresponding modules in the embodiment shown in FIG. 10.

Second Example Embodiments of the Device

The Reaction Vessel Holder

Figure 24:
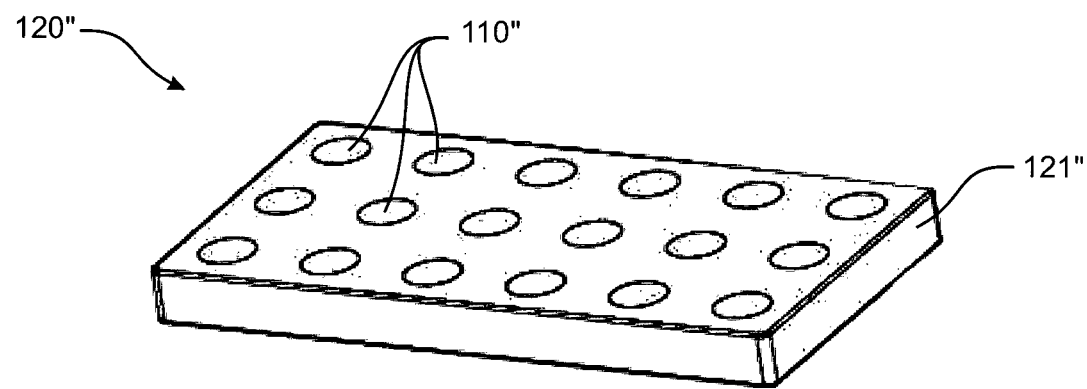
FIG. 24 shows a perspective view of the reaction vessel holder for a device according to second example embodiments of the present invention.

FIG. 24 shows the reaction vessel holder 120" for the reaction vessel of the second example embodiments of the invention. The reaction holder 120" is in the form of a cassette housing 121" that comprises one or more reaction chambers 110" that can be closed. In the embodiment shown, the reaction vessel holder 120" comprises eighteen reaction chambers 110" that are integral with the reaction vessel holder 120". As previously described, the reaction vessels 110" may alternatively be removable from the reaction vessel holder 120".

The or each reaction chamber 110" has a low volume and is configured to receive a sample for molecule detection. By having no air gap above the reaction mixture, the need for lens heaters is eliminated. The housing 121" may be disposable. The reaction vessel holder 120" is optically transparent on bottom side and on a top side to allow an excitation light to enter the reaction chamber 110" from the top or bottom side and to allow a reaction light to exit the reaction chamber 110" from the opposite bottom or top side.

In one embodiment, the reaction chambers 110" in the reaction vessel holder 120" may be separable from each other. For example, a row of reaction chambers may be frangibly separable from other reaction chambers in the housing.

The Optical Assembly

Figure 25:
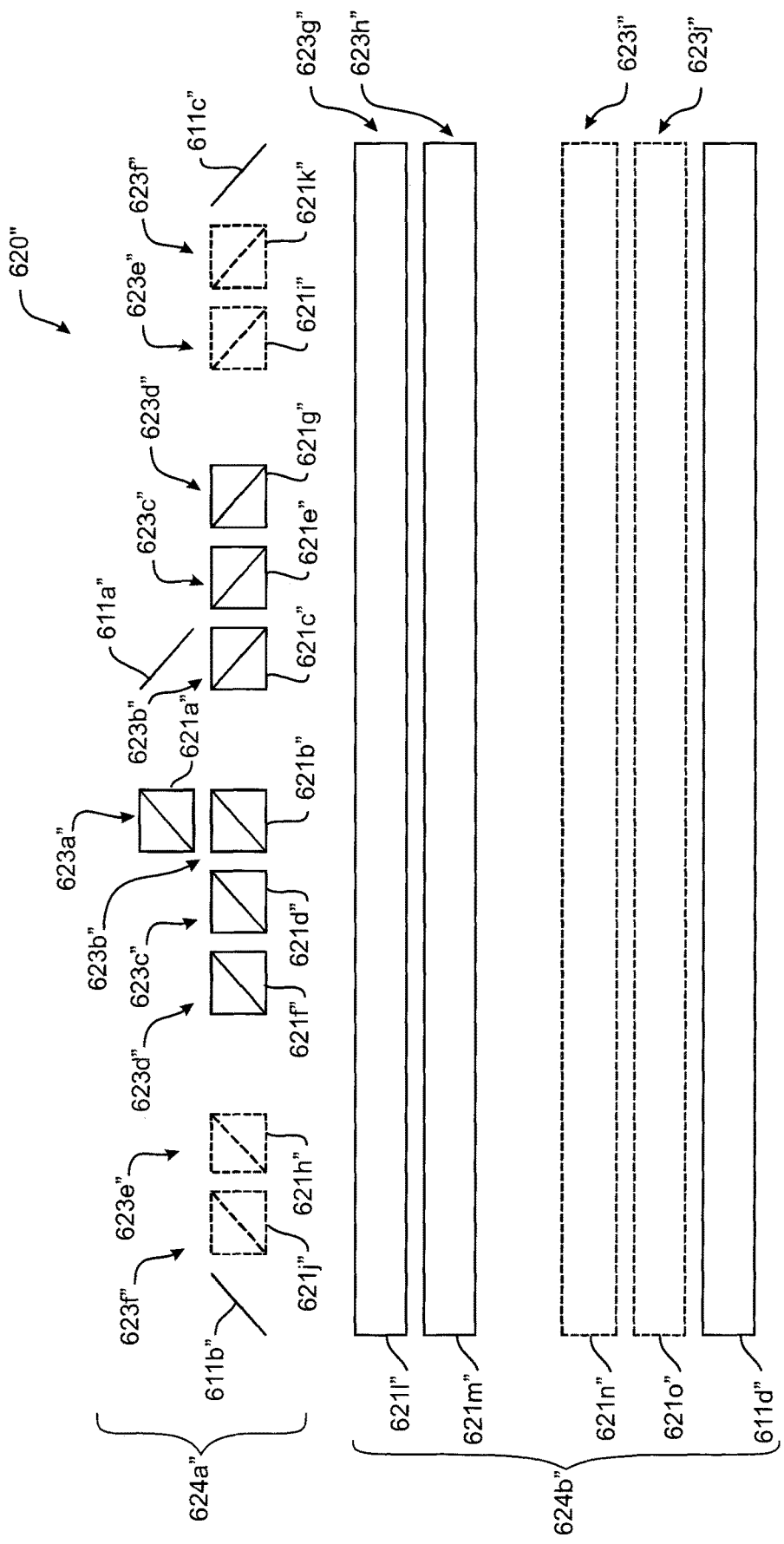
FIG. 25 shows a schematic general beam splitter arrangement of the device according to the second example embodiments of the present invention.

FIG. 25 shows the beam splitter arrangement 620" for second example embodiments of the device. The beam splitter arrangement 620" is configured to split the excitation beam into up to k number of split excitation beams, k being an even integer greater than two, wherein the beam splitters 621a"-o" are arranged in (m+n) number of tiers 623a"-j", where m and n are integers indicating the number of primary tiers 624a" and secondary tiers 624b" respectively, m being an integer greater than one and n being an integer greater than zero, and k=2×m×(n+1). The first tier 623a", which is one of the primary tiers 624a", contains one beam splitter 621a" that is configured to receive the excitation beam, and to split the incoming beam into two split excitation beams.

An $i^{th}$ tier 623b"-f", which is one of the primary tiers 624a", i being an integer ranging from 2 to m, is configured to receive incoming beams from a previous tier 623a"-e" and to split each incoming beam into two split excitation beams. In the case where i is less than m, one of the split excitation beams is directed to the next tier 623c"-f" and the other split excitation beam is directed to the $(m+1)^{th}$ tier 623g". In the case where i equals m, the split excitation beams from the $m^{th}$ tier 623f" are directed to the $(m+1)^{th}$ tier 623g" of the secondary tiers 624b". The second tier 623b" comprises two beam splitters 621b"-c" for receiving the split excitation beams from the first tier 623a" and for splitting each incoming beam into two beams, one of which is directed to the third tier 623c" and the other which is directed to the $(m+1)^{th}$ tier 623g". The third tier 623c" comprises two beam splitters 621d"-e" for receiving the split excitation beams from the second tier 623b" and for splitting each incoming beam into two beams, one of which is directed to the fourth tier 623c" and the other which is directed to the $(m+1)^{th}$ tier 623g". The fourth tier 623d" comprises two beam splitters 621f"-g" for receiving the split excitation beams from the third tier 623c" and for splitting each incoming beam into two beams, one of which is directed to the fifth tier and the other which is directed to the $(m+1)^{th}$ tier 623g". The m-$1^{th}$ tier 623e" comprises two beam splitters 621h"-i" for receiving the split excitation beams from the m-$2^{th}$ tier and for splitting each incoming beam into two beams, one of which is directed to the $m^{th}$ tier 623f" and the other which is directed to the $(m+1)^{th}$ tier 623g". The $m^{th}$ tier 623f" comprises two beam splitters 623j"-k" for receiving the split excitation beams from the m-$2^{th}$ tier 623e" and for splitting each incoming beam into two beams. Each split excitation beam from the $m^{th}$ tier 623f" is directed to the $(m+1)^{th}$ tier 623g".

A $j^{th}$ tier 623g"-j", which is one of the secondary tiers 624b", j being an integer ranging from m+1 to m+n, is configured to receive incoming beams from a previous tier and to split each incoming beam into two split excitation beams. In the case where j is less than n, one of the split excitation beams is directed to the next tier and the other split excitation beam is one of the k split excitation beams. In the case where j equals m+n, each split excitation beam from the $(m+n)^{th}$ tier 623j" is one of the k split excitation beams. The m+$1^{th}$ tier 623g" comprises a plate beam splitter 621l" for receiving the split excitation beams from the previous tiers 623b"-h" and for splitting each incoming beam into two beams, one of which is directed to the m+$2^{th}$ tier 623h" and the other which is one of the k split excitation beams. The m+$2^{th}$ tier 623h" comprises a plate beam splitter 621m" for receiving the split excitation beams from the m+$1^{th}$ tier 623g" and for splitting each incoming beam into two beams, one of which is directed to the m+$3^{th}$ tier and the other which is one of the k split excitation beams. The (m+n-$1)^{th}$ tier 623i" comprises a plate beam splitter 621n" for receiving the split excitation beams from the (m+n-$2)^{th}$ tier and for splitting each incoming beam into two beams, one of which is directed to the $(m+n)^{th}$ tier 623j" and the other which is k split excitation beams. The $(m+n)^{th}$ tier comprises one plate beam splitter 621o" for receiving the split excitation beam from the (m+n-$1)^{th}$ tier 623i". Each split excitation beam from the $(m+n)^{th}$ tier 623j" is one of the k split excitation beams.

The beam splitter arrangement 620" comprises mirrors 611a"-d" to allow a compact positioning of beam splitters. These mirrors 611a"-d" are optional, and according to alternative embodiments of the device, the mirrors may not be present.

In a balanced tier configuration, where the beam splitter arrangement 620" is configured to produce k split excitation beams of substantially equal intensity and wavelength, the $i^{th}$ tier 623b"-f" is configured to split each incoming beam into two split excitation beams having a beam intensity of about $$\frac{100}{m-(i-2)}\%$$

and about $$100\left(1 - \frac{1}{m-(i-2)}\right)\%$$

respectively. The split excitation beam with the higher intensity is directed to the next tier while the split excitation beam with the lower intensity is directed to the $(m+1)^{th}$ tier 623g". The split excitation beams from the $m^{th}$ tier 623f" are directed to the $(m+1)^{th}$ tier 623g". The $j^{th}$ tier 623g"-j" is configured to split each incoming beam into two split excitation beams having a beam intensity of about $$\frac{100}{(m+n)-(j-2)}\%$$

and about $$100\left(1 - \frac{1}{(m+n)-(j-2)}\right)\%$$

respectively. The split excitation beam with the higher intensity is directed to the next tier and the split excitation beam with the lower intensity is one of the k split excitation beams. Each split excitation beam from the m+$n^{th}$ tier 623j" is one of the k split excitation beams.

Figure 26:
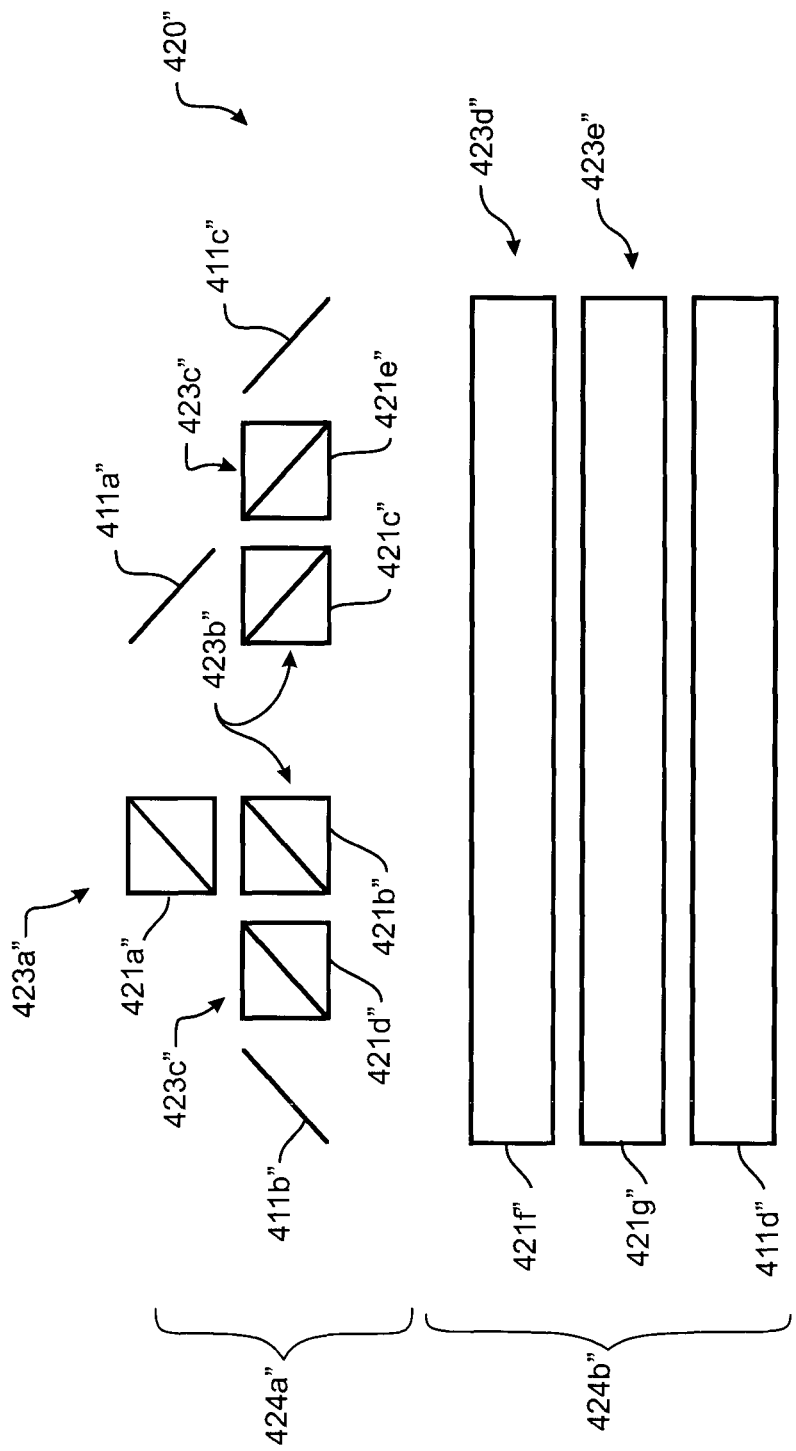
FIG. 26 shows a schematic eighteen-channel beam splitter arrangement of the device according to the second example embodiments of the present invention.

FIG. 26 shows the beam splitter arrangement 420" of the second example embodiments for an eighteen channel device. The beam splitter arrangement 420" of the device for detecting molecule(s) in eighteen reaction vessels has five tiers 423a"-e", three of which 423a"-c" are primary tiers 424a" and two of which 423d"-e" are secondary tiers 424b". A first tier 423a" comprises one beam splitter 421a" and is configured to receive the excitation beam from the collimator and to split the excitation beam into two beams of substantially equal intensities. A second tier 423b" comprises two beam splitters 421b"-c". The second tier 423b" is configured to receive two incoming beams from the first tier 423a" and to split each incoming beam into a split excitation beam of about 33% intensity and a split excitation beam of about 67% intensity. A third tier 423c" comprises two beam splitters 421d"-e". The third tier 423c" is configured to receive the two split excitation beams of about 67% intensity from the second tier 423b" and to split each incoming beam into two split excitation beams of substantially equal intensities. A fourth tier 423d" of the secondary tiers 424b" comprises a plate beam splitter 421f". The fourth tier 423d" is configured to receive the two 33% intensity split excitation beams from the second tier 423b" and four split excitation beams from the third tier 423c" and to split each incoming beam into a split excitation beam of about 33% intensity and a split excitation beam of about 67% intensity. A fifth tier 423e" comprises a plate beam splitter 421g". The fifth tier 423e" is configured to receive the six split excitation beams of about 67% intensity from the fourth tier 423d" and to split each incoming beam into two split excitation beams of substantially equal intensities. The eighteen split excitation beams of substantially equal intensity and wavelength comprise six split excitation beams of about 33% intensity from the fourth tier 423d" and twelve split excitation beams from the fifth tier 423e".

Similar to the first example embodiments of the device, the beam splitter arrangements of the second example embodiments may comprise a polarising cube beam splitter or non-polarising cube beam splitters. Where the beam splitter arrangement comprises a polarising cube beam splitter, the excitation beam entering the polarising cube beam splitter is first passed through a half wave plate, before being incident onto the polarising cube beam splitter. Alternatively, a half wave plate may not be provided, and the polarising beam splitter or the excitation source may be rotated accordingly such that the polarising beam splitter can produce to split beams of substantially equal or unequal intensities. The beam splitter arrangement may comprise a combination of at least one half-wave plate, at least one polarising cube beam splitter, and at least one non-polarising cube beam splitter.

In the embodiment shown in FIGS. 25 and 26, the primary tiers 424a", 624a" comprise cube beam splitters, while the secondary tiers 424b", 624b" comprise plate beam splitters. According to an alternative embodiment, the primary tiers and secondary tiers may both comprise cube beam splitters. According to a further alternative embodiment, the primary and secondary tiers may both comprise plate beam splitters. According to the embodiment shown in FIG. 27, the primary tiers 824a" and secondary tiers 824b" of the beam splitter arrangement 820" comprises only plate beam splitters 821a"-g".

Figure 27A:
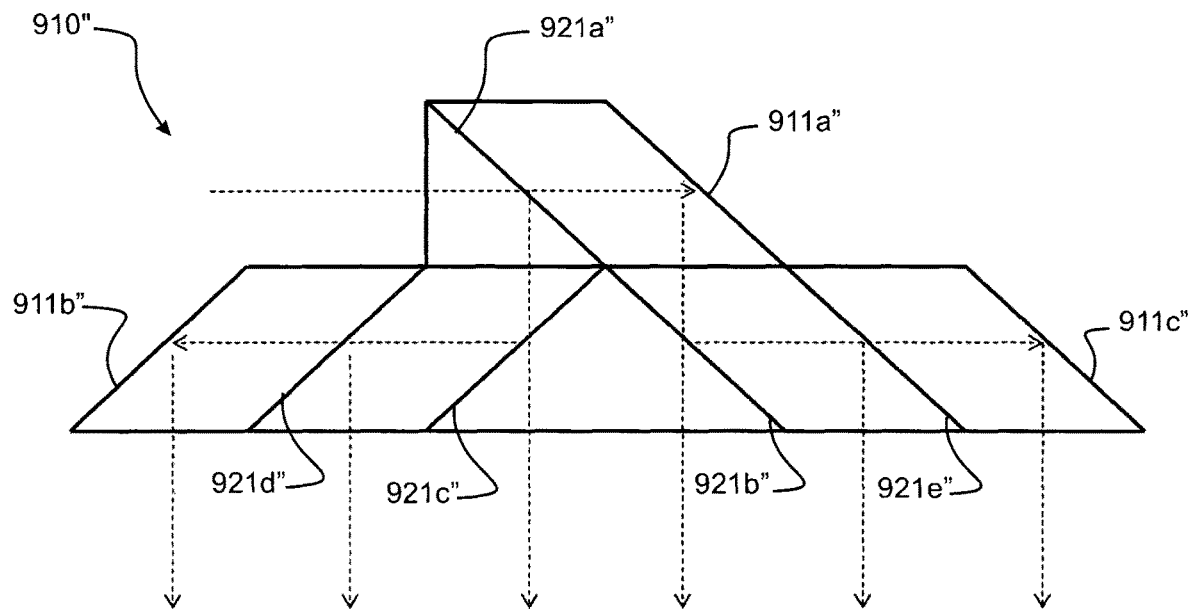
FIG. 27a shows an alternate schematic of the primary tiers of the eighteen-channel beam splitter arrangement of the device according to the second example embodiments of the present invention.
Figure 27B:
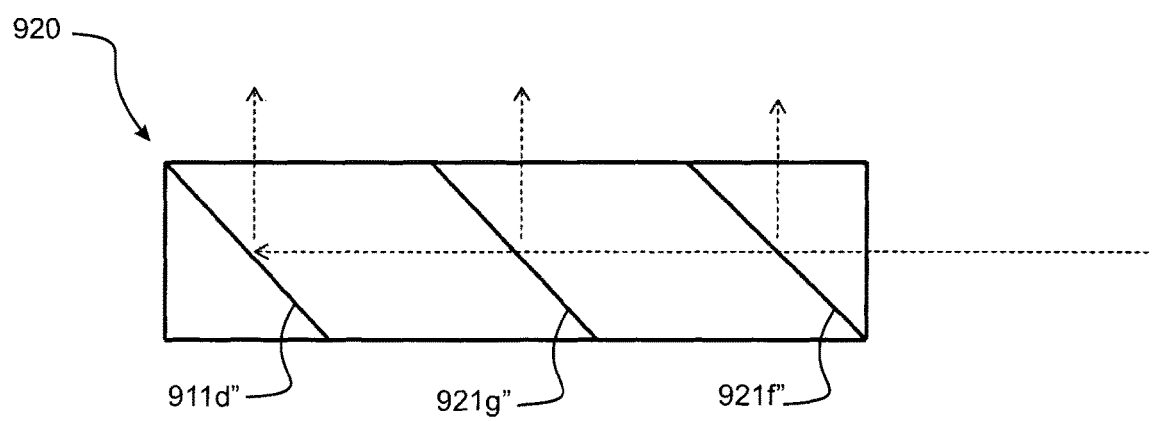
FIG. 27b shows an alternate schematic of the secondary tiers of the eighteen-channel beam splitter arrangement of the device according to the second example embodiments of the present invention.

FIGS. 27a and 27b show an alternative embodiment of the beam splitter arrangement where the beam splitters of the primary tiers are together a primary monolithic optical component 910 (shown in FIG. 27a), and the beam splitters of the secondary tiers are together a secondary monolithic optical component 920 (shown in FIG. 27a). Referring to FIG. 27a, the primary monolithic optical component 910 forms five beam splitters 921a"-e" and three mirrors 911a"-c" and is configured to receive a single excitation beam and to output six split excitation beams. Referring to FIG. 27b, the secondary monolithic optical component 920 forms two beam splitters 921f"-g" and a mirror 911d" and is configured to receive the six split excitation beams output by the primary monolithic optical component 910, and to output eighteen split excitation beams. Optical index matching material is used to fill interstitial air gaps and to fuse together adjacent beam splitters. The monolithic optical components 910, 920 can be formed from a plurality of pieces of optical material of the required geometry (for example trapezoidal and/or right angle parts).

Figure 28:
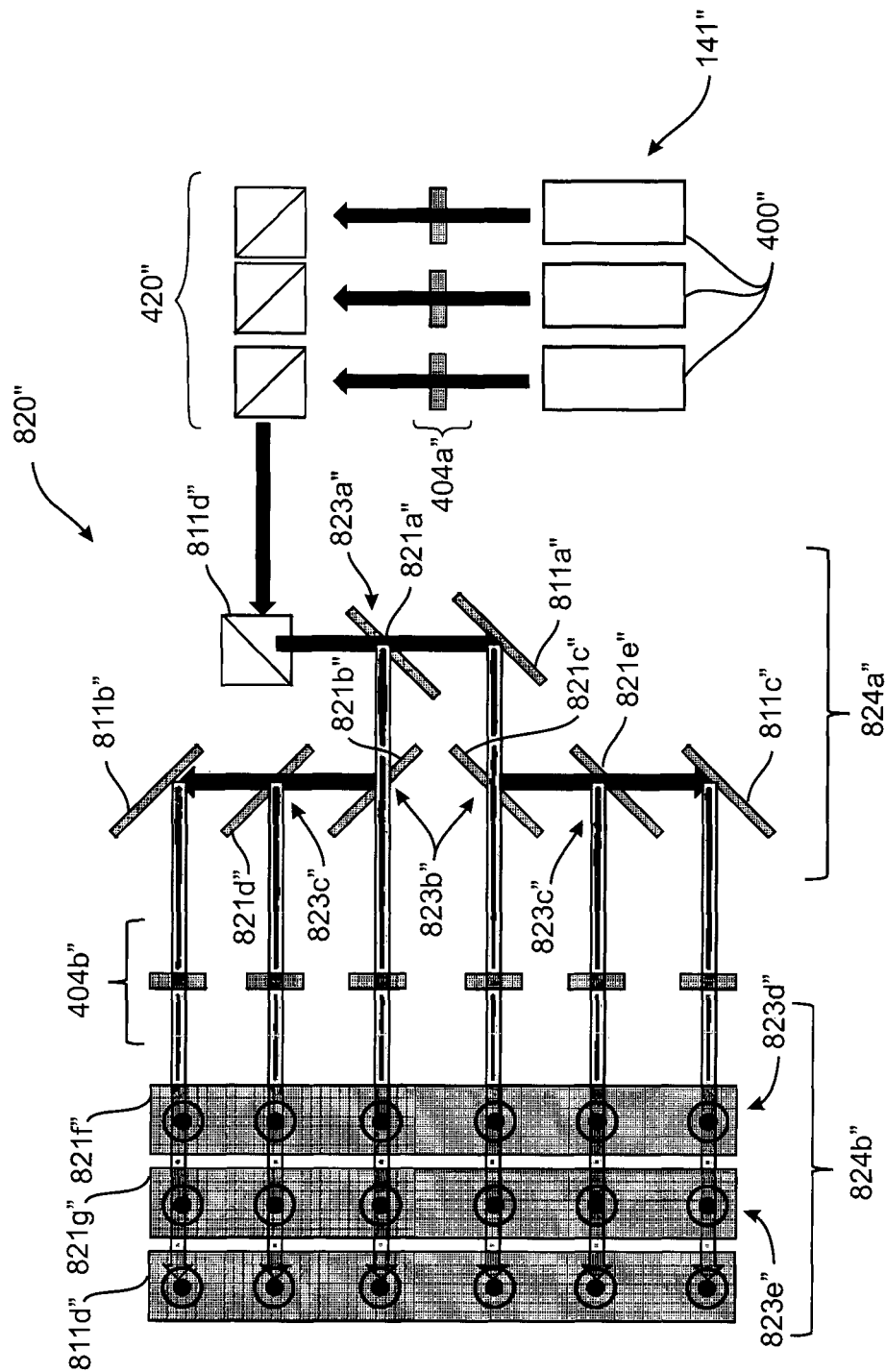
FIG. 28 shows an alternate schematic eighteen-channel beam splitter arrangement in the device according to the second example embodiments of the present invention.

Referring to FIG. 28, the excitation source 400" used in the excitation arrangement 414" may comprise a plurality of excitation sources, as previously described. The excitation arrangement 141" is configured to generate an excitation beam having a plurality of excitation wavelengths in the interval of about 400 nm to about 700 nm for example. The excitation arrangement 141" comprises a first excitation source for transmitting an excitation beam at a red wavelength, a second excitation source for transmitting an excitation beam at a green wavelength, and a third excitation source for transmitting an excitation beam at a blue wavelength. Each of the first, second and third excitation sources 400" comprises a Nichia laser diode. The laser diode is configured to emit an excitation beam at the suitable wavelength. According to an alternative embodiment, the excitation arrangement may comprise a single excitation source for transmitting an excitation beam at a single wavelength.

Each of the excitation beams from the excitation source 400" passes through a respective collimating lens which collimates the excitation beam, and which is respectively part of the first, second and third excitation source. The collimating lenses are part of the excitation sources 400". The collimated excitation beam then passes through a neutral density filter and a laser line clean-up interference filter 404a". The excitation arrangement 141" comprises beam combination optics 420" for combining the three excitation beams from the different excitation sources 400" into a single excitation beam. In one embodiment, the beam combination optics 420" comprise two interference filters only for combining the excitation beams. In another embodiment, the beam combination optics 420" comprise one interference filter and one polarizing cube beam splitter/combiner.

Apertures are found throughout the device. For example, the apertures may take the form of the various apertures in the various beam splitters through which the excitation beam propagates.

The excitation beam then passes through a beam splitter arrangement 820" for splitting the excitation beam into eighteen split excitation beams. The beam splitter arrangement 820" is substantially similar to the arrangement described with reference to FIG. 26, with the exception of plate beam splitters being used in all of the tiers.

A mirror 511d" is used to guide the excitation beam from the excitation arrangement 141" to the beam splitter arrangement 820". The beam splitter arrangement 820" has five tiers 823a"-e", three of which 823a"-c" are primary tiers 824a" and two of which 823d"-e" are secondary tiers 824b". A first tier 823a" comprises one plate beam splitter 821a" and is configured to receive the excitation beam from the collimator and to split the excitation beam into two beams of substantially equal intensities. A second tier 823b" comprises two plate beam splitters 821b"-c". The second tier 823b" is configured to receive two incoming beams from the first tier 823a" and to split each incoming beam into a split excitation beam of about 33% intensity and a split excitation beam of about 67% intensity. A third tier 823c" comprises two plate beam splitters 821d"-e". The third tier 823c" is configured to receive the two split excitation beams of about 67% intensity from the second tier 823b" and to split each incoming beam into two split excitation beams of substantially equal intensities. A fourth tier 823d" of the secondary tiers 824b" comprises a plate beam splitter 821f". The fourth tier 823d" is configured to receive the two 33% intensity split excitation beams from the second tier 823*b*" and four split excitation beams from the third tier 823*c*" and to split each incoming beam into a split excitation beam of about 33% intensity and a split excitation beam of about 67% intensity. A fifth tier 823*e*" comprises a plate beam splitter 821*g*". The fifth tier 823*e*" is configured to receive the six split excitation beams of about 67% intensity from the fourth tier 823*d*" and to split each incoming beam into two split excitation beams of substantially equal intensities. The eighteen split excitation beams of substantially equal intensity and wavelength comprise six split excitation beams of about 33% intensity from the fourth tier 823*d*" and twelve split excitation beams from the fifth tier 823*e*". Mirrors 811*a*"-*d*" guide the split excitation beam from a respective previous tier in a direction that is parallel with the direction of other split excitation beams from the respective previous tier. The beam splitter arrangement 820" further comprises neutral density filter positioned between the primary tiers 823*a*"-*c*" and the secondary tiers 823*d*"-*e*". The split excitation beams from the secondary tiers 823*d*"-*e*" and mirror 811*d*" are in a direction out of the page.

Figure 29:
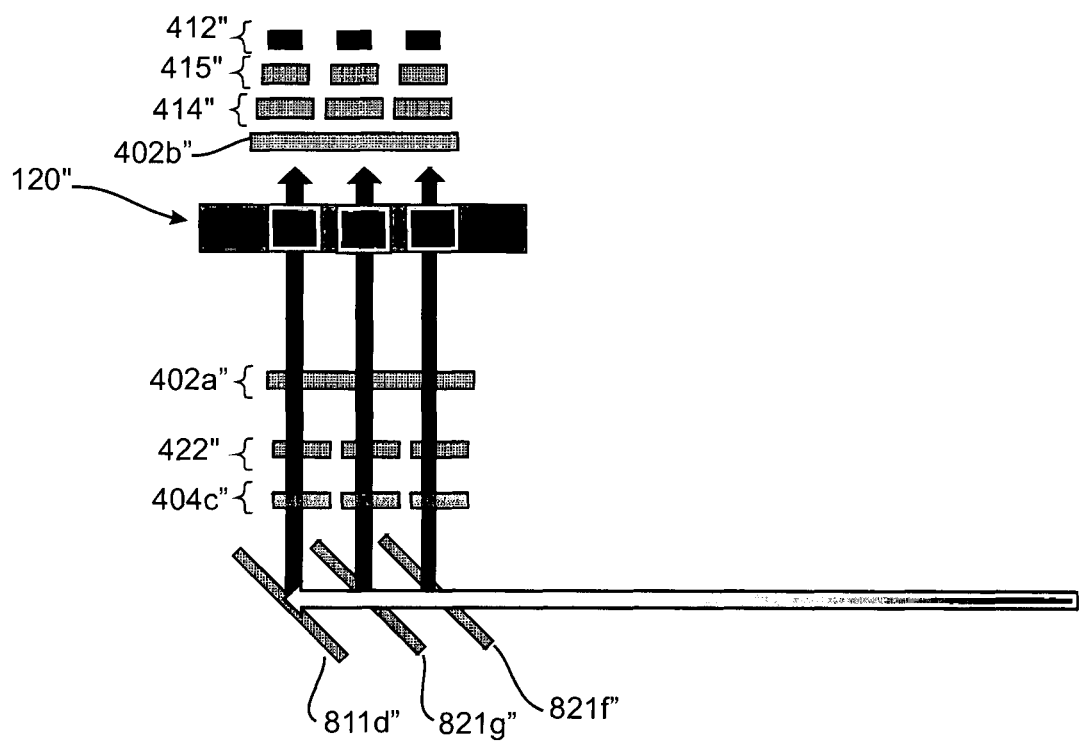
FIG. 29 shows a partial optical arrangement of the device according to the second example embodiments of the present invention.

FIG. 29 shows the arrangement for guiding three of the eighteen excitation beams from the arrangement shown in FIG. 28 to the reaction vessel 120" and for guiding the reaction light from the reaction vessel 120" to the detector arrangement 412". Each excitation beam from the fourth tier 823*d*", fifth tier 823*e*" and mirror 811*d*" are respectively guided through a neutral density filter 404*c*" followed by a polariser 422". Each beam is then passed through a first dichroic or filter element 402*a*", which is configured to pass the excitation beam while reflecting any reaction light. Alternatively, the first dichroic element may be configured to block or attenuate the reaction light. The first dichroic element 402*a*" guides the excitation beam to the reaction vessel 120" to stimulate an emission of reaction light from the reaction vessel 120". In an alternative embodiment, the first dichroic element 402*a*" may not be present. In that embodiment, a bottom surface of the reaction vessel holder 120" may be coated with an optical coating for passing excitation beams, while reflecting reaction light. In another embodiment each excitation beam may additionally be passed through a focusing lens in order to focus the excitation light into the sample. The focusing lenses may be located either side of the first dichroic element 402*a*".

Reaction light from the reaction vessel passes through a second dichroic or filter element 402*b*", which is configured to block or reflect the excitation beams, while passing the reaction light towards the detector assembly 412". The reaction light passes through imaging/focusing lenses 414" for focusing the reaction light onto the detector assembly 412". The reaction light passes through glass filters, which acts as an additional block to excitation beams. Alternatively, the imaging/focusing lenses 414" may be positioned immediately after the reaction vessel holder 120", before the second dichroic element 402*b*".

As previously discussed, where a plurality of excitation wavelengths are used or where the reaction light comprises multiple reaction light wavelengths, the dichroic element may be replaced by a multi-transition interference filter, such as a trichroic element, a notch filter or a multi-bandpass filter for example. The multi-transition interference filter is an interference filter that may be used to block or reflect two wavelengths while being transmissive for a different wavelength. By way of example, where the multi-transition interference filter is a trichroic element and the excitation beam comprises two excitation wavelengths, the trichroic element may be reflective for two excitation beam wavelengths, while being transmissive for the reaction light wavelengths.

In a further form of the second example embodiments, the 18 channel beam splitter arrangement can be configured in a downward looking excitation geometry (as used in the first example embodiments of the device). In this form, the output from the primary tiers of beam splitters into the secondary tiers of beam splitters would be similar to that previously described. The beam splitters of the secondary tiers would be transparent at the reaction light wavelength.

Casing

Figure 30:
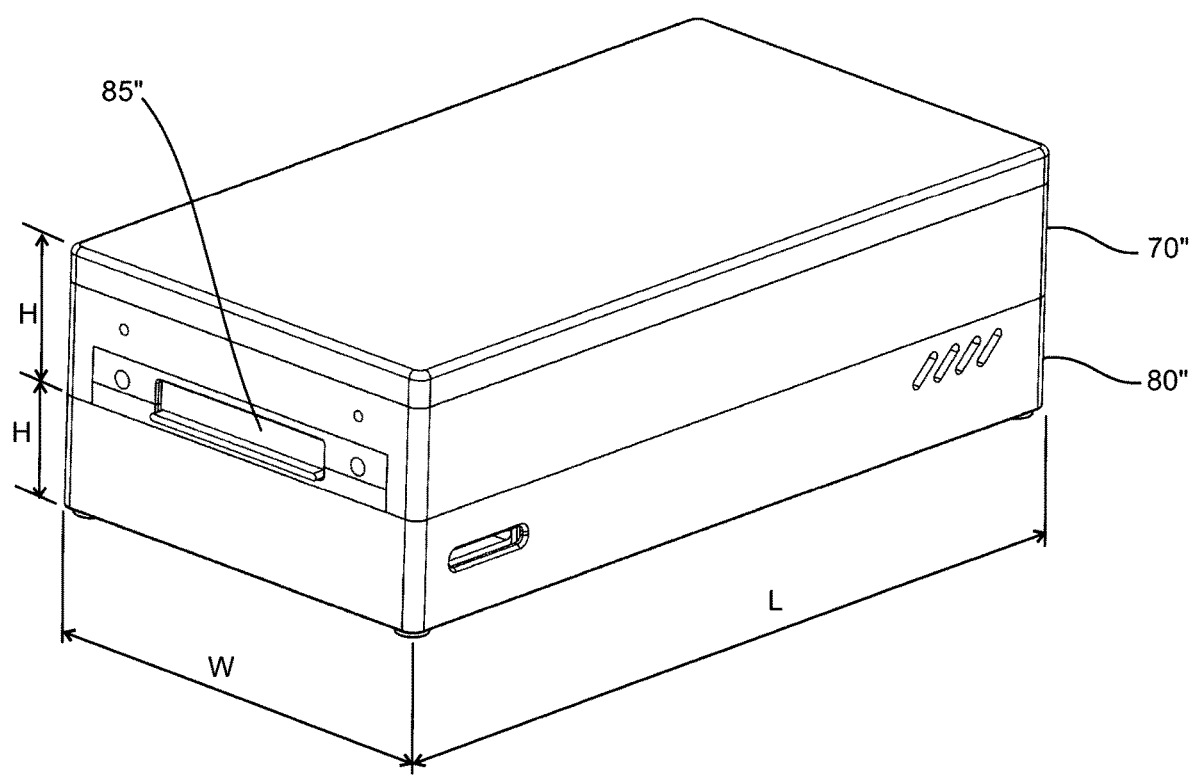
FIG. 30 shows a perspective view of the device according to the second example embodiments of the present invention.

FIG. 30 shows a device for detecting molecule(s) in eighteen reaction vessels. The device comprises an upper casing 70" and a lower casing 80". The reaction vessels are removably insertable into the lower casing 80". The lower casing 80" comprises a door 85" that can be opened to receive the reaction vessel holder. The door 85" may be a sliding door. Alternatively, the upper casing 70" is moveable relative to the lower casing 80" between a closed configuration and an open configuration.

Figure 31:
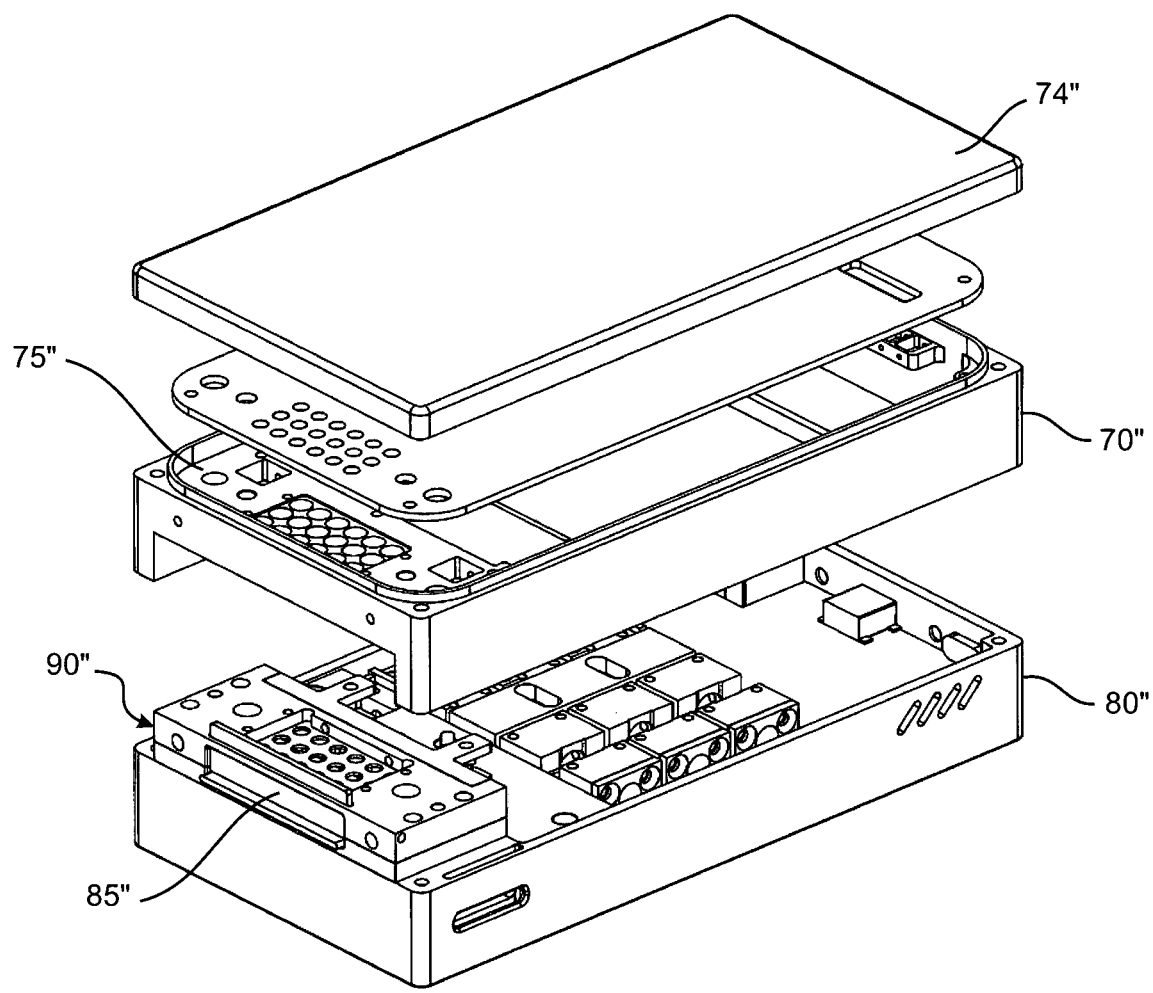
FIG. 31 shows an exploded view of the device of FIG. 30.

Referring to FIG. 31, the upper casing 70" houses the controller, battery, power supply, and the optical assembly for detection of the reaction light. The lower casing 80" houses the excitation source, a power jack, a USB interface hub, the beam splitter arrangement and the reaction vessels. The upper casing comprises a cap 74" which is removably connected to the upper casing 70". The upper casing further comprises a detector assembly housing 75" for housing components of the detector assembly including the imaging lenses and the glass filters. The lower casing 80" comprises an optical assembly housing 90" for housing the excitation arrangement and the guide arrangement.

The optical assembly housing 90" comprises an excitation arrangement housing for housing components of the excitation arrangement and components of the guide arrangement between the excitation arrangement and the reaction vessel holder, and a guide arrangement housing for housing components of the guide arrangement required for guiding the reaction light from the reaction vessel holder to the detector arrangement. The guide arrangement housing is adapted to house the dichroic filters for guiding the reaction light to the detector arrangement. The guide arrangement housing further comprises the door 85" which is configured to receive the reaction vessel holder.

Figure 32:
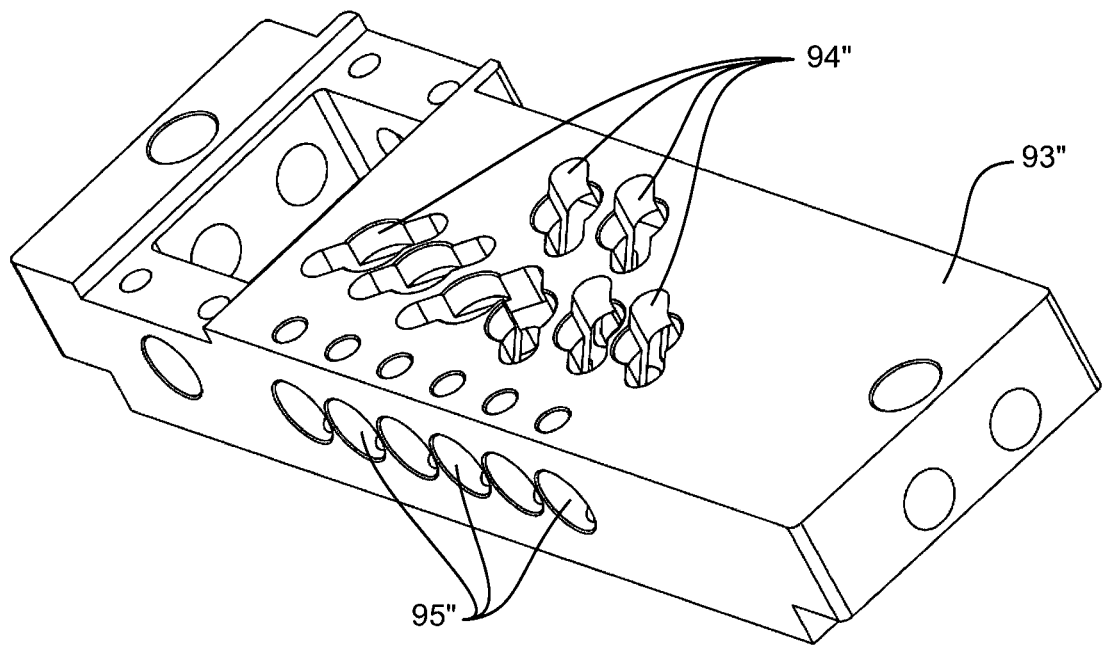
FIG. 32 shows the housing for the primary tier of beam splitters of the device of FIG. 30.
Figure 33:
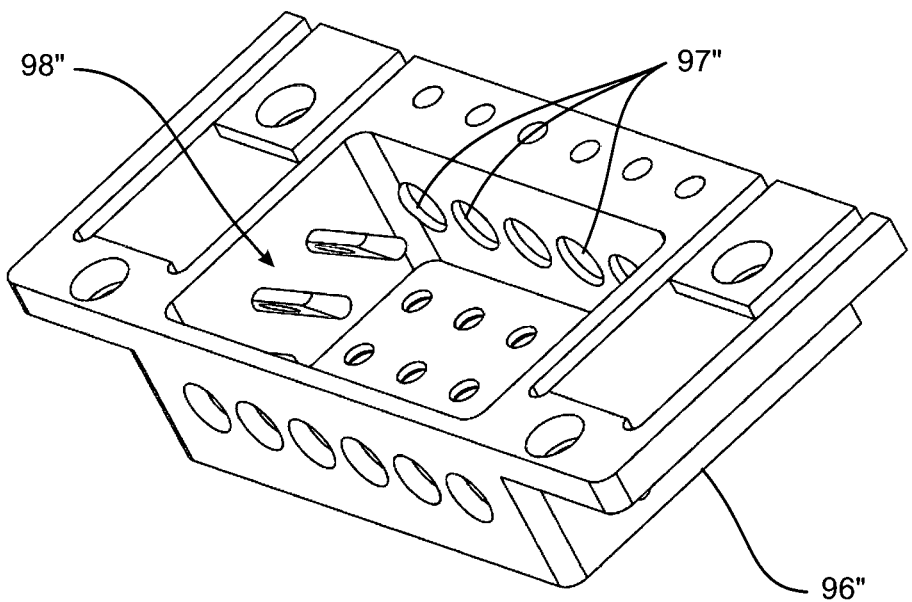
FIG. 33 shows the housing for the secondary tier of beam splitters of the device of FIG. 30.

The excitation arrangement housing comprises in part the secondary tiers housing 96" shown in FIG. 33. The primary tiers housing 93" shown in FIGS. 31 and 32 is located adjacent to the secondary tiers housing 96".

Referring to FIG. 32, the primary tiers housing 93" is for housing the primary tiers of the beam splitter arrangement. The primary tiers housing 93" is block-shaped having a plurality of slots 94", wherein each slot is configured to receive a plate beam splitter. In an alternative embodiment, the primary tiers housing 93" does not comprise slots, and may instead comprise a recess for receiving the beam splitters and the steering mirrors. The housing 93" has a series of apertures and channels 95" to allow the excitation beam to be split and pass to the next tier or to the secondary tiers in the secondary tiers housing 96".

Referring to FIG. 33, the secondary tiers housing 96" for housing the secondary tiers of the beam splitter arrangement comprises a series of apertures 97" for receiving the excitation beam from the primary tiers housing. The secondary tiers housing 96" further comprises a recess 98" for receiving the beam splitters of the secondary tiers. The reaction vessel holder is positioned substantially above the recess 98", and the split excitation beams are directed upwards from the recess 98".

Referring back to FIG. 30, in one embodiment, the dimensions of the device are (length×width×height) 120 mm×64 mm×37 mm. The dimensions of the upper casing 70" are L=120 mm×W=64 mm×H=21 mm, and the dimensions of the lower casing 80" are L=120 mm×W=60 mm×H=16 mm.

Controller

The controller is similar to the controller for the device of the first example embodiments.

Third Example Embodiments of the Device

The third example embodiments of the device are substantially similar to the second example embodiments of the device. One of the differences between the two example embodiments is the beam splitter arrangement. According to the third example embodiments, the secondary tiers in the beam splitter arrangement of the second example embodiments are not present.

Figure 34:
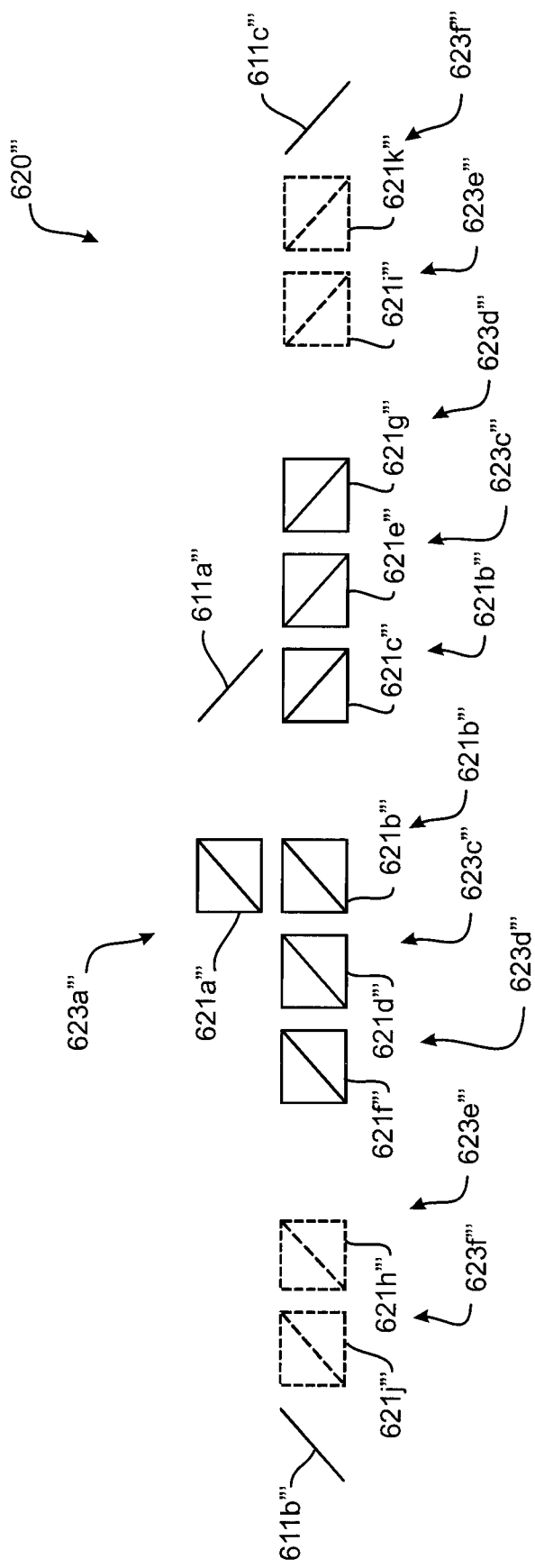
FIG. 34 shows a schematic general beam splitter arrangement of the device according to the third example embodiments of the present invention.

Referring to FIG. 34, the beam splitter arrangement 620''' is configured to split the excitation beam into up to k number of split excitation beams, k being an even integer greater than two, wherein the beam splitters 621a'''-621k''' are arranged in m number of tiers 623a'''-f''', where m is an integer greater than 1 and k=2×m. A first tier 623a''' contains one beam splitter 621a''' that is configured to receive the excitation beam from an excitation arrangement, and to split the incoming beam into two split excitation beams. An $i^{th}$ tier 623b'''-f''', i being an integer ranging from 2 to m, is configured to receive incoming beams from a previous tier 623a'''-e''' and to split each incoming beam into two split excitation beams, wherein in the case where i is less than m, one of the split excitation beams is directed to the next tier and the other split excitation beam is one of the k split excitation beams. The second tier 623b''' comprises two beam splitters 621b'''-c''' for receiving the split excitation beams from the first tier 623a''' and for splitting each incoming beam into two beams, one of which is directed to the third tier 623c''' and the other which is one of the k split excitation beams. The third tier 623c''' comprises two beam splitters 621d'''-e''' for receiving the split excitation beams from the second tier 623b''' and for splitting each incoming beam into two beams, one of which is directed to the fourth tier 623d''' and the other which is one of the k split excitation beams. The fourth tier 623d''' comprises two beam splitters 621f'''-g''' for receiving the split excitation beams from the third tier 623c''' and for splitting each incoming beam into two beams, one of which is directed to the fifth tier and the other which is one of the k split excitation beams. The m−$1^{th}$ tier 623e''' comprises two beam splitters 621h'''-i''' for receiving the split excitation beams from the m−$2^{th}$ tier and for splitting each incoming beam into two beams, one of which is directed to the $m^{th}$ tier 623f''' and the other which is one of the k split excitation beams. The $m^{th}$ tier 623f''' comprises two beam splitters 621j'''-k''' for receiving the split excitation beams from the m−$2^{th}$ tier 623e''' and for splitting each incoming beam into two beams. Each split excitation beams from the $m^{th}$ tier 623f''' is one of the k split excitation beams. The beam splitter arrangement 620''' comprises mirrors 611a'''-c''' to allow a compact positioning of beam splitters 621a'''-k'''. These mirrors are optional, and according to alternative embodiments of the device, the mirrors may not be present.

In a balanced tier configuration, where the beam splitter arrangement is configured to produce k split excitation beams of substantially equal intensity and wavelength, the $i^{th}$ tier 623b''-f''' is configured to split each incoming beam into two split excitation beams having a beam intensity of about $$\frac{100}{m-(i-2)}\%$$

and about $$100\left(1 - \frac{1}{m-(i-2)}\right)\%$$

respectively. The split excitation beam with the higher intensity is directed to the next tier, while the split excitation beam with the lower intensity is one of the k split excitation beams. Each split excitation beams from the $m^{th}$ tier 623f''' is one of the k split excitation beams.

Figure 35:
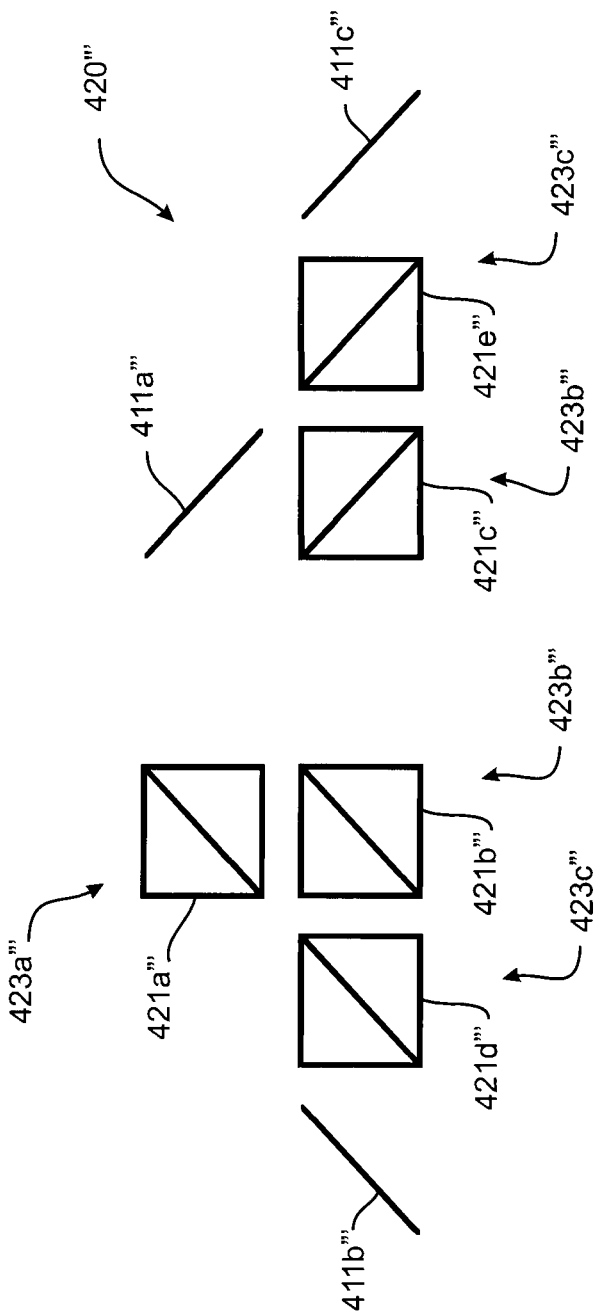
FIG. 35 shows a schematic six-channel beam splitter arrangement of the device according to the second example embodiments of the present invention.
Figure 36:
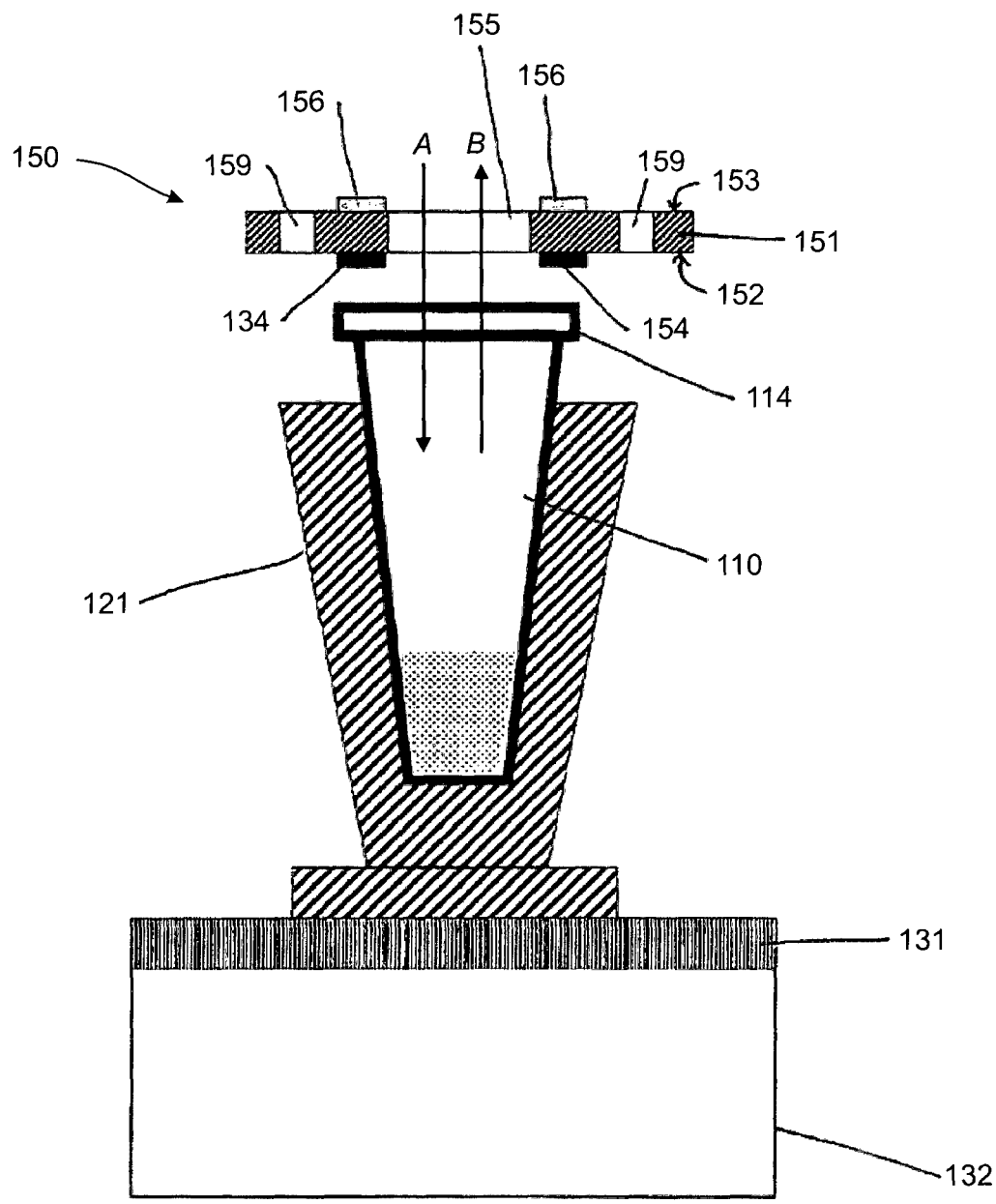
FIG. 36 shows a side view of a reaction vessel held by a vessel receptacle and a lens heater.

Referring to FIG. 35, the beam splitter arrangement 420''' of an embodiment of the device for detecting molecule(s) in six reaction vessels has three tiers 423a'''-c'''. A first tier 423a''' comprises one beam splitter 421a''' and is configured to receive the excitation beam from the collimator and to split the excitation beam into two beams of substantially equal intensities. A second tier 423b''' comprises two beam splitters 421b'''-c'''. The second tier 423b''' is configured to receive two incoming beams from the first tier 423a''' and to split each incoming beam into a split excitation beam of about 33% intensity and a split excitation beam of about 67% intensity. A third tier 423c''' comprises two beam splitters 421d'''-e'''. The third tier 423c''' is configured to receive the two split excitation beams of about 67% intensity from the second tier 423b''' and to split each incoming beam into two split excitation beams of substantially equal intensities. The six split excitation beams of substantially equal intensity and wavelength comprise the split excitation beams of about 33% intensity from the second tier 423b''' and the split excitation beams from the third tier 423c'''. The beam splitter arrangement comprises a first mirror 411a''' for folding the optical path of the split excitation beam from the first beam splitter 421a''' toward the beam splitter 421c'''. The beam splitter arrangement additionally comprises a second mirror 411b''' and a third mirror 411c''' for folding the optical path of the split excitation beams from the beam splitters 421d'''-e''' of the third tier 423c''' respectively in the same direction as the other split excitation beams of the k number of split excitation beams.

According to FIGS. 34 and 35, the beam splitters are shown to be cube beam splitters. However, the beam splitter arrangement could comprise plate beam splitters or a combination of plate and cube beam splitters. As previously described with reference to the first example embodiments and second example embodiments of the device, two or more beam splitters may together be a single monolithic optical component.

The casing of the third example embodiments may be substantially similar to that of the first example embodiments or second example embodiments. The casing would be modified accordingly to accommodate the layout of the beam splitter arrangement.

The Reaction Vessel Cover Heater

Figure 37A:
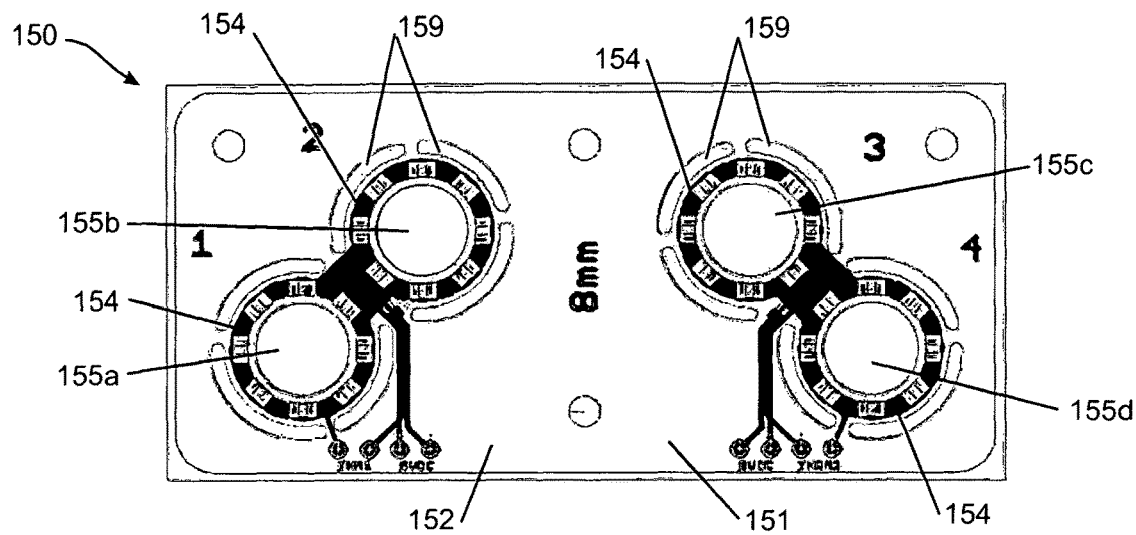
FIG. 37a shows a first layer of the lens heater of an embodiment of the present invention.
Figure 37B:
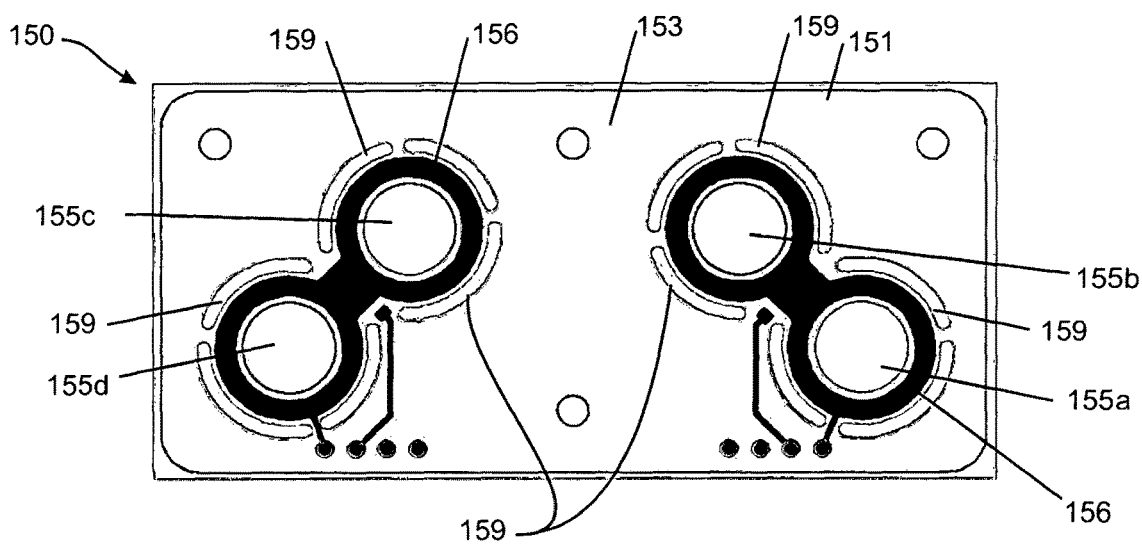
Figure 38:
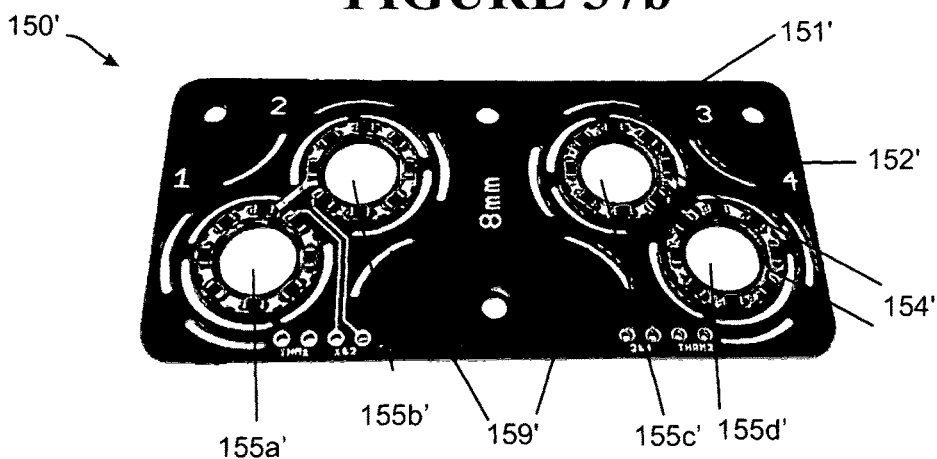
FIG. 38 shows a first layer of the lens heater according to another embodiment of the present invention.

Referring to FIGS. 36 to 39, the device may further comprise a reaction vessel cover heater 150. The function of the reaction vessel cover heater 150 is to prevent the formation of condensation on the transparent or translucent cover 114 of the reaction vessel 110 which may interfere with the optical signals of the excitation path A into and detection path B from the reaction vessel 110. The reaction vessel cover heater 150 achieves this by radiatively heating the cover of the reaction vessel 110. FIGS. 37a to 38 show an embodiment of the reaction vessel cover heaters 150 for heating the cover of four reaction vessels. It will be appreciated that the reaction vessel cover heaters 150 can be modified accordingly to allow heating of less than or more than four covers of reaction vessels.

The reaction vessel cover heater 150 is compact (thin and lightweight) and also low in power consumption while the heating element(s) are capable of attaining a temperature of a desired level (such as about 100° C. to within a few degrees). In addition, the temperature of the reaction vessel cover heater 150 can be actively maintained within the required temperature interval in order that ambient temperature does not influence the actual heater temperature as would be the case if a constant current were passed through the reaction vessel cover heater 150. Further, the method used to regulate the average current through the reaction vessel cover heater 150 is efficient and does not waste electrical energy in a dissipative sense (as is the case for a linear type regulator for example).

The reaction vessel cover heater 150 of embodiments of the present invention is formed from a printed circuit board (PCB) 151 having a thickness of about 0.6 mm. The insulation of the PCB 151 ensures that heat transfer losses from the thermal elements via conduction are minimized. The PCB 151 comprises poor but sufficient thermal conductivity properties which allow a transfer of heat from one side of the PCB 151 to the other side of the PCB 151.

The PCB 151 has a two layer (double sided) configuration with a first layer 152 and second layer 153. Both layers comprise copper traces. An aperture 155a-d for each reaction vessel is formed in the PCB 151 through which the excitation beam on excitation path A and reaction light from the detection path B may pass.

Referring to FIG. 37a, the first layer 152 of the PCB 151 is configured to face the reaction vessels. This layer 152 comprises an arrangement of heating elements 154. The heating elements 154 may be for example surface mount resistors of high temperature application. The heating elements 154 may be arranged in an annular/ring arrangement around each aperture 155a-d. The heating elements 154 around the aperture 155a-d are interconnected with each other via surface copper traces. Further, the heating elements 154 around an aperture 155a-d may be thermally and/or conductively connected via a conductive track with heating elements 154 around an adjacent aperture 155a-d. Alternatively, the heating elements around an aperture 155a-d may be thermally and/or conductively isolated from heating elements 154 around other apertures 155a-d on the PCB 151.

The PCB 151 comprises a series of milled arcs 159 which substantially surround the heating elements 154 and frustrate heat trying to leave the heated area via conduction. The milled arcs may be replaced by an insulative material.

Referring to FIG. 37b, the second layer 153 comprises conductor which is preferably a heat spreading copper trace 156 which substantially follows the general arrangement of the corresponding heating elements 154. This trace 156 on layer 153 uniformly redistributes the heat which flows through the PCB 151 from the heating elements in a direction substantially normal to the surface of the PCB 151. The heat spreading copper trace 156 ensures that each of the interconnected heating elements 154 is at the same temperature through a thermal averaging effect. Further, a copper trace 156 around an aperture may be thermally and/or conductively connected to a copper trace around an adjacent aperture. Alternatively, the copper trace around an aperture may be thermally and/or conductively isolated from copper trace around other apertures on the board.

A closed cell thermally insulating foam is affixed to the heat spreading copper trace 156 to limit and prevent heat loss from the trace 156 and the second layer 153 via radiation and convection.

A platinum resistive thermal device is connected to the heat spreading copper trace 156. The platinum resistive thermal device (RTD) is used in preference to a thermistor due to its high temperature stability and repeatability. Based on the temperature of the heat spreading copper trace 156, the RTD develops a voltage across it which the controller uses to issue the appropriate duty cycle pulse width (PWM) modulated power signal to the heating elements 154. PWM is used as it is a highly efficient means of controlling power to the heating elements 154. Alternatively, the controller may comprise a comparator circuit which is configured to issue an ON or OFF power signal to the heating elements based on the measured temperature and a predetermined temperature value.

Figure 39:
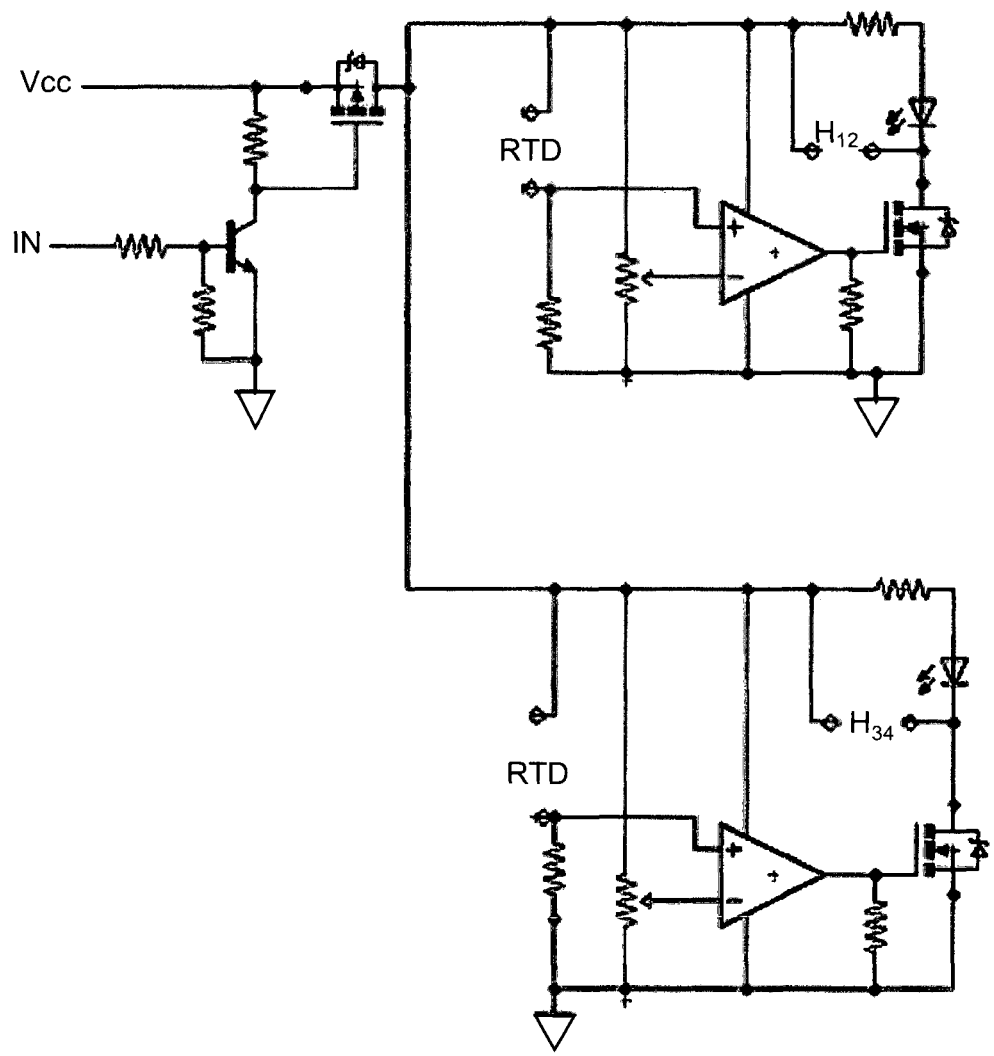
FIG. 39 shows a circuit schematic of the comparator for the lens heater.

Referring to the schematic shown in FIG. 39, the comparator circuit uses a single rail operational amplifier OP-AMP as a comparator to compare the resistance (via generated voltage) of a RTD to a variable voltage as set by a trimming potentiometer (TRIM-POT). The RTD used in this configuration is configured to have a resistance of about 146 ohms at a temperature of about 120° C. The temperature set-point is adjusted by adjusting the trimming potentiometer reference voltage. The operational amplifier then switches the N-Channel MOSFETs on and off as required to maintain the set-point temperature. The top comparator circuit for a pair of heating elements $H_{12}$ for apertures 155a-b is identical to the bottom comparator circuit for a pair of heating elements $H_{34}$ for apertures 155c-d. A single P-channel MOSFET is used to switch power to the heater circuits (controlled by a NPN transistor with micro-controller input IN).

The reaction vessel cover heater is attached to the underside of the upper casing in the recess the sample lenses are located. The reaction vessel cover heater is preferably positioned such that the heating element(s) is/are about 1.5 mm to about 3 mm, and preferably 2 mm from the cover of the reaction vessel. The reaction vessel cover heater is affixed by its extremities to the aluminium housing of the device though the use of stainless steel screws and thermally insulating Teflon washers which act as spacers to separate and thermally insulate the board from the underside of the upper casing.

In the closed configuration, the sample lenses 'look' through the aperture of the reaction vessel cover heater in such a manner that the excitation beam to or the reaction light from the sample does not clip the reaction vessel cover heater. The diameter of each aperture is chosen such that the angle extended from each heating element cannot be seen from the position of the sample in the lower test tube. Preferably, the aperture has a diameter of about 8 mm. This arrangement is used so that energy radiated from the heater elements does not reach and potentially interfere with the temperature of the sample.

FIG. 38 shows an alternative reaction vessel cover heater 150', where like parts are indicated with like reference numerals with an addition of a prime ('). The only difference with the embodiment shown in FIGS. 37a and 37b is the additional milled arcs 159' through the board.

Experiment 1

Use of Hand Held Device for Detecting Protein

Introduction

A broad range of molecular diagnostic tests are based on the detection of proteins. These tests can use different classes of reagents, for example, antibodies or ligands, to indicate the presence or absence of specific proteins in a sample. For example, a protein test, can show presence of troponin in the blood stream indicating heart damage or detection of her-2/neu protein can inform breast cancer treatment. Such tests also can be used to analyse microbial communities. This could be whether a food spoilage organism, like *Salmonella*, is present as well as the level of microorganism contamination of the item.

A common reporter protein used in molecular diagnostic tests is the Green Fluorescent Protein. This protein was first isolated from *Aequorea victoria*, a free-swimming Cnidaria that lives off the coast of North America and is the reason for this jellyfish's bioluminescence. The GFP protein has a natural excitation peak of 395 nm and an emission peak of 509 nm. However, since its cooption for use in biological research the fundamental structure of GFP has been genetically engineered to produce a range of GFP family proteins that emit at a plurality of wavelengths ranging from red to blue.

In the experiments described here we investigated whether our technology could detect a commonly used fluorescent reporter protein (GFP) used in molecular diagnostic tests.

Methods

Instrumentation

All measurements were performed using the One-Sample Hand Held Device (1sHHD) of a preferred embodiment of the invention as described above with reference to FIGS. 1-12. The technology configuration consisted of the thermal control unit.

Test Protein

Biopolymer beads incorporating either Green Fluorescent Protein (GFP) or without GFP were grown in vivo and were supplied as a gift from PolyBactics Ltd (Palmerston North, New Zealand). Biobeads were referred to as GFP or WT, respectively. Beads were suspended at various dilutions in TE pH7.5 buffer.

Microscopy

Biobead images were taken using an Olympus AX70 fluorescent microscope. Solution containing the biobeads was spotted onto a microscope slide, coverslipped and viewed at 4× magnification.

Results

Figure 40:
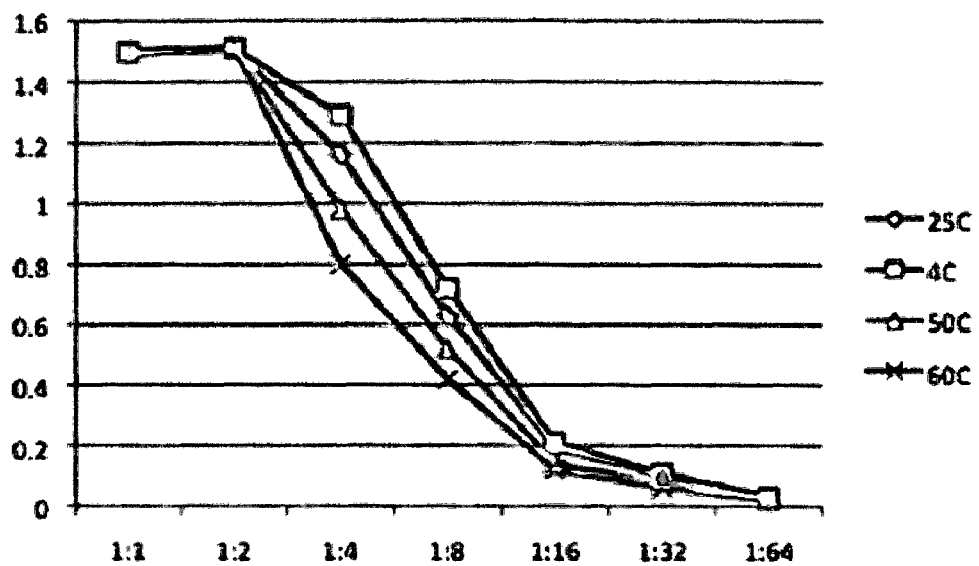
FIG. 40 shows a plot of the fluorescence against the biobead serial dilution of a first batch of biobeads.

A series of experiments using GFP protein biobeads supplied by PolyBatics Ltd were performed in combination with the single-sample device (1sHHD). The beads were serially diluted in TE buffer from neat to 1:64 fold (1:1, 1:2, 1:4, 1:8, 1:16, 1:32, 1:64). The 1sHHD was programmed to hold the sample at a single temperature and fluorescence measured from the sample. Each sample was measured at four different temperatures (4° C., 25° C., 50° C. and 60° C.). Ten microlitres of the sample was place in the reaction chamber and allowed to equilibrate to temperature for 20 seconds. This was followed by measuring fluorescence four times at 25 second intervals. Fluorescence was detected and measurements reflected the GFP biobead dilution (FIG. 40). Each sample was measured at four different temperatures. Interestingly the results suggested temperature affected the intensity of GFP fluorescence pointing to the potential importance of precise temperature control during measurement.

Figure 41:
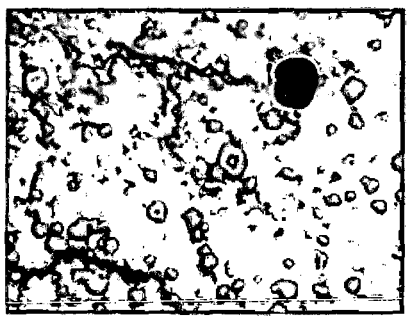
FIG. 41 shows four different views of biobeads using fluorescent microscopy.
Figure 41:
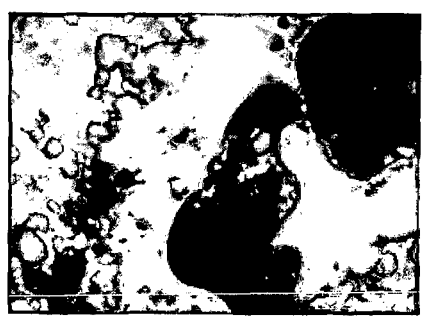
Figure 41:
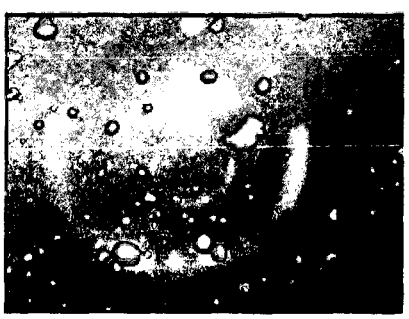
Figure 41:

Two fresh samples of protein biobeads were obtained from PolyBatics Ltd. One of the samples carried the GFP protein while the other (Wild Type or WT) did not. To verify that the WT biobeads did not emit light at the GFP wavelength, dilutions of both biobead samples were viewed by fluorescent microscopy. As seen in FIG. 41, only the GFP-containing biobeads emitted light at the green wavelength. Both WT and GFP biobeads were viewed neat (1:1) and at a 1:16 dilution of the initial biobead solution. The images in FIG. 41 of the biobead samples were taken at 4× magnification.

The 1sHHD was used to measure fluorescence over two-fold serial dilutions of both the GFP and WT biobeads. The reaction chamber temperature was maintained at 25° C. for these measurements. This procedure involved placing 10 µl of sample in the reaction chamber of the 1sHHD. The sample was allowed to equilibrate to 25° C. for 20 seconds. Four fluorescent measurements were then recorded by the 1sHHD at 25 second intervals. Results are given in Table 1. Fluorescence was only detected from the GFP containing biobeads.

TABLE 1

Fluorescence measurements from GFP and WT biobeads

| Biobead Dilution Factor | GFP | WT | TE buffer |
| --- | --- | --- | --- |
| 1:1 | 1.42 | 0.03 | 0.2 |
| 1:2 | 1.43 | 0.03 | |
| 1:4 | 1.44 | 0.02 | |
| 1:8 | 1.45 | 0.02 | |
| 1:16 | 1.45 | 0.02 | |
| 1:32 | 1.45 | 0.02 | |

Figure 42:
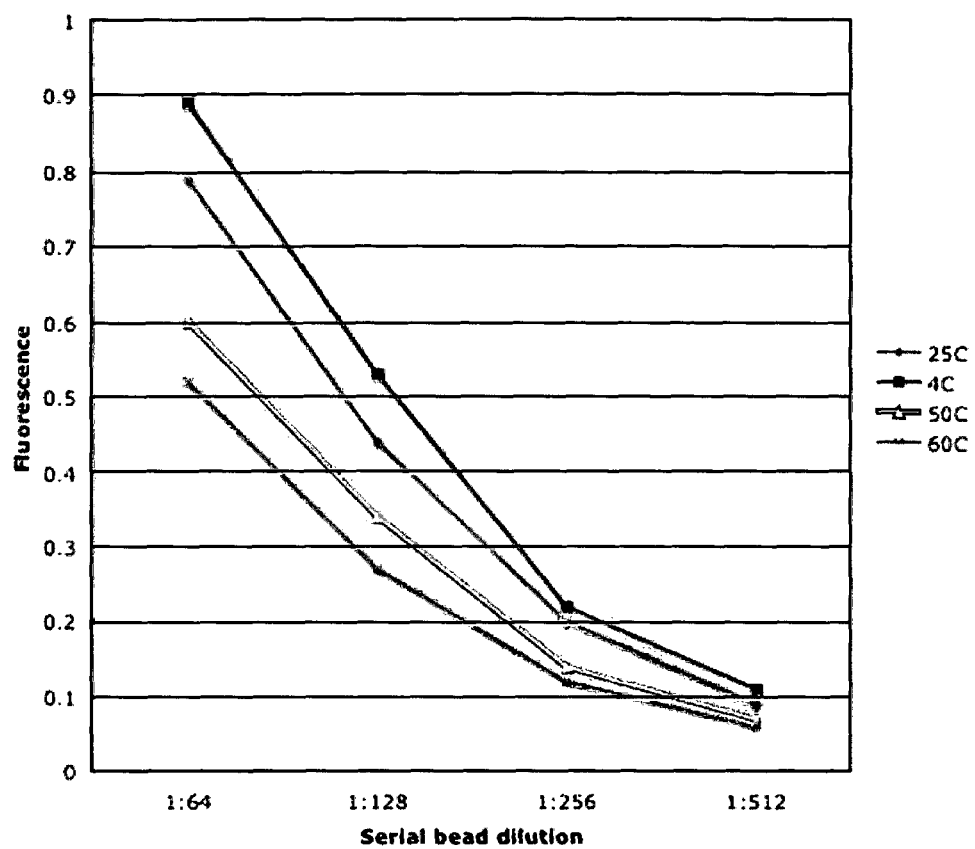
FIG. 42 shows a plot of fluorescence against serial biobead dilution of a second batch of biobeads.

Results from the second batch of GFP biobeads suggested that they were capable of producing greater levels of measureable fluorescence. We tested this hypothesis by extending the two fold dilution series of the biobeads to 1:512 and the 1sHHD used to measure fluorescence as in the previous experiments. Results are given in Table 2 and FIG. 42. These results demonstrated that the second batch of biobeads was more active and that fluorescence detection was affected by temperature.

TABLE 2

Fluorescence from GFP biobeads taken at four different temperatures

| GFP Biobead Dilution | 25° C. | 4° C. | 50° C. | 60° C. |
| --- | --- | --- | --- | --- |
| 1:64 | 0.79 | 0.89 | 0.60 | 0.52 |
| 1:128 | 0.44 | 0.53 | 0.34 | 0.27 |
| 1:256 | 0.20 | 0.22 | 0.14 | 0.12 |
| 1:512 | 0.09 | 0.11 | 0.07 | 0.06 |

Conclusion

The 1sHHD was able to detect GFP protein and fluorescence measurements reflected the quantity of protein present in the sample. These experiments also indicated that temperature has an effect on the strength of the fluorescent signal. The tight temperature control, coupled to optical detection of the 1sHHD was able to demonstrate this. These results indicate that the 1sHHD and other devices containing this technology can be used in protein-based reporting and diagnostic systems.

Experiment 2

Four-Sample Hand Held Device Used for Quantitative PCR

Introduction

The performance of a preferred embodiment Four-Sample Hand Held Device (as described above with reference to FIGS. 1, 2, and 13-23) as a quantitative Polymerase Chain Reaction (Q-PCR) instrument was measured against a standard laboratory-based Q-PCR instrument supplied commercially from Roche. This commercial system was the LightCycler 480.

In this work a series of Q-PCR reactions were run in parallel on both instruments and the cycle threshold (Ct), or the cycle number at which the measured fluorescence crossed a set threshold, was used to compare performance. All reactions comprised of the same Q-PCR Assay components and used the same reagents, plasticware and thermal-cycling conditions. Each experiment was set up from the same master mix and was carried out on both instruments at the same time.

The Q-PCR assay used for this work utilised a transgenic mouse line engineered to express an actin-GFP fusion protein. The assay designed for this work amplified the GFP genomic DNA sequence from this mouse. The assay specifically picked out the target sequence from the complex mixture of sequences that make up the remainder of the mouse genome and reflected conditions of a real-world application for PCR. In fact, the assay designed for this work could have immediate application for general screening programs for transgenic mouse or cell lines.

Methods

Instrumentation:

Two devices were used in the tests outlined below. These were the Q-PCR LightCycler 480 (LC480) from Roche and the Four-sample Hand Held embodiment device (4sHHD) of the present invention.

Mouse Tissue:

All DNA used in this work was extracted from a transgenic mouse line that had incorporated into its genome a GFP-Actin construct. The effect was production of a fusion protein that is incorporated into the cytoskeleton of the mouse's cells causing the animal to fluoresce green when exposed to the appropriate wavelength of light. Only fluorescent green animals were used for this work, thus ensuring they carried the transgene.

Genomic DNA Extraction:

Two genomic DNA extraction systems were used interchangeably throughout these experiments. These were the QIAgen DNeasy Blood and Tissue kit (Cat No. 69504) and the ZyGem prepGEM Tissue kit. DNA was extracted from 17 mg and 22 mg of GFP transgenic mouse liver respectively as per the manufacturer's instructions. This produced two DNA samples, one with a concentration of 14.5 ng/µl and a second with a concentration of 19.9 ng/µl DNA.

Q-PCR Methods:

The CLONTECH eGFP-N1 vector was used to construct the GFP-Actin transgenic mouse line. PCR primers were designed to this vector to amplify the GFP DNA encoding sequence. The NCBI primer design tool, available on the NCBI website (http://ncbi.nlm.nih.gov) was used to design the forward and reverse primers for GFP. Primers are given in Table 3.

TABLE 3

Q-PCR Primers

| Primer Name | Sequence |
|---|---|
| eGFP-Short Forward | TTCAGCCGCTACCCCGACCA (SEQ ID NO: 1) |
| eGFP-Short Reverse | CGGTTCACCAGGGTGTCGCC (SEQ ID NO: 2) |

All reaction mixes used the LightCycler 480 SYBR Green I Master Mix System from Roche (Cat No. 04 707 516001). For each 20 µl reaction the following mix of components were used: 10 µl SYBR Green I Master Mix; 1 µl (20 pmol) of both Forward and Reverse Primer; 7 µl PCR quality $H_2O$; and either 1 µl DNA (between 14 ng and 20 ng) or 1 µl $H_2O$. A Master Mix of Q-PCR reagents consisting of enough reagents to perform a plurality of reactions was set up for each experiment. To do this the volumes required for each component making the final 20 µl reaction were multiplied by the number of reactions needed for the experiment plus one extra to allow for pipetting errors. When a negative control, or blank, was required, 19 µl of the master mix was removed and 1 µl of $H_2O$ was added to the blank to bring the volume to 20 µl.

All Q-PCR reactions were carried out using Roche LightCycler 480 Multiwell Plate plasticware and sealing foils (Cat No. 04 729 692 001: LightCycler 480 Multiwell Plate 96, 50 Plates with Sealing Foils). Unmodified PCR plates and foils were used for experiments conducted on the Roche LC480. For use with the 4sHHD wells were punched from the LightCycler 480 Multiwell Plate to form individual tubes and a custom press used to apply the sealing film to the top of these tubes once loaded with Q-PCR reagent.

Identical thermal-cycle conditions were used on both devices to amplify the target GFP sequence from genomic DNA. These conditions were 95° C. for five minutes followed by 40 cycles of 95° C. for 30 seconds, 60° C. for 30 seconds and 72° C. for 30 seconds. These three temperatures constitute a cycle: DNA denaturation at 95° C., primer annealing at 60° C. and primer extension and fluorescence measurement at 72° C.

Results

Comparison of Q-PCR Results from the LC480 and 4sHHD with Constant DNA Concentration.

Figure 43A:
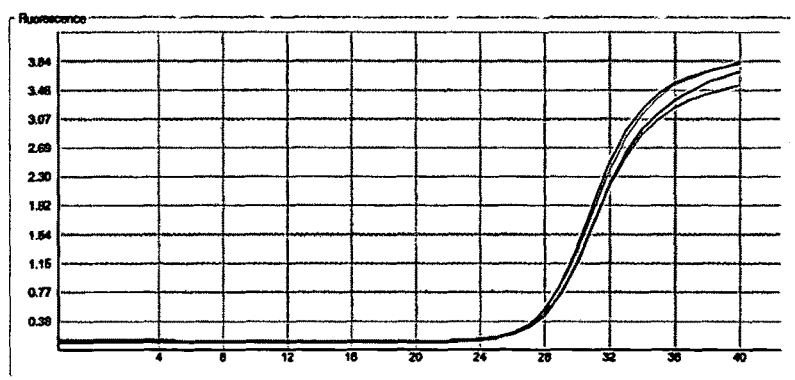
FIG. 43a shows a plot of fluorescence against the cycle number for q-PCR analysis using a device for detecting molecule(s) in four reaction vessels according to an embodiment of the present invention.
Figure 43B:
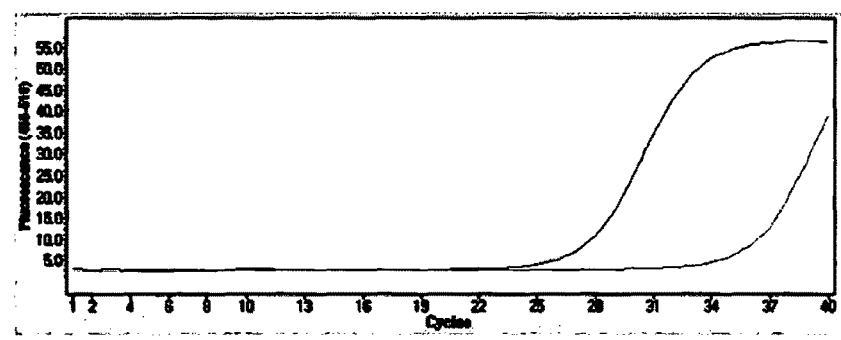
FIG. 43b shows a plot of fluorescence against cycle number for q-PCR analysis using an existing Roche LC480 device.

Side-by-side comparisons of the performance of the LC480 and the 4sHHD were conducted. A single Master Mix was made to run on both instruments. Additionally, once 19 µl of the Master Mix was removed for the blank, or negative control, DNA template was added directly to the Master Mix and all components mixed well. This ensured that all reactions contained exactly the same concentration of DNA at the beginning of the Q-PCR process. Twenty microlitres of Master Mix with DNA was aliquoted into four modified PCR tubes for the 4sHHD and into a single well on an intact 96 well Q-PCR plate. The negative control, containing no DNA, was also included on the 96 well plate to be run on the LC480. Tubes and the plate were sealed with identical sealing foil and each reaction subjected to simultaneous Q-PCR on both devices. An example of the results obtained from these experiments is given in FIG. 43a for the 4sHHD and FIG. 43b for the LC480. In FIG. 43b, the lower curve is for the negative control reaction.

Ct values for each Q-PCR were calculated by hand. Manual Ct determination was performed due to 1) the 4sHHD used for this work did not have software capable of automatically defining Ct and 2) not being able to apply the LC480 software packages to the 4sHHD data. Ct for each reaction curve was calculated by identifying the point at which the curve first rose from the baseline, or threshold, established from fluorescence data from the proceeding cycles. Ct values are given in Table 4.

TABLE 4

Comparison of Ct values for samples with constant amount of DNA

| Run | 4sHHD Ct values | LC480 Ct values |
|---|---|---|
| 080811b | 25 | 25 |
| 290711 | 25 | 25 |
| 290611 | 22 | 20.5 |
| 200611 | 27 | 23.5 |

Relative quantitative DNA analysis comparison between the 4sHHD and LC480

Comparison of Ct values between the 4sHHD device and the LC480 showed they exhibited comparable sensitivity. In each case the cycle number at which PCR product amplification was first detected was similar. Little variance was observed between the four separate reaction chambers of the 4sHHD. In all cases, this led to one Ct value for all four reactions. This is the expected outcome given the same amount of starting DNA was present in each tube.

To compare the ability of the 4sHHD to determine relative quantity of starting DNA to the performance of the LC480, a serial dilution of the genomic DNA was set up for use as Q-PCR template. Four dilutions were used. These were neat, 1:10, 1:100 and 1:1000. One microlitre of each dilution was added to different 19 µl aliquots of Q-PCR Master Mix in tubes and to wells in Q-PCR plates. A blank, or negative control, was included on the Q-PCR plate for running on the LC480. Tubes and plate were sealed with the same sealing foil.

Figure 44A:
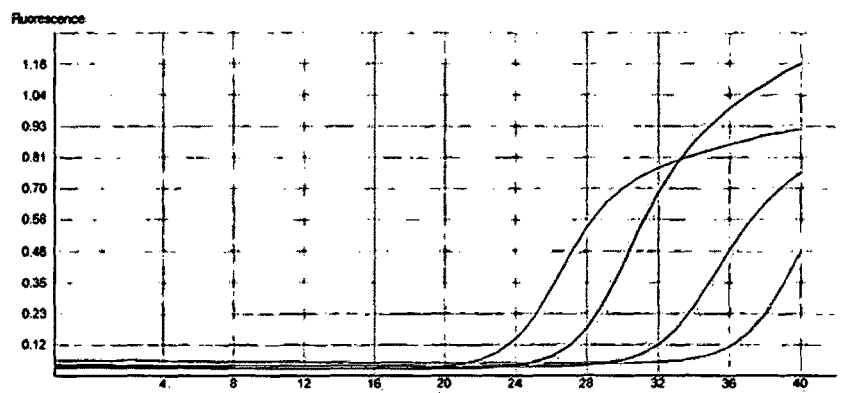
FIG. 44a shows a plot of fluorescence against cycle number for q-PCR analysis using a device for amplification and detection of nucleic acids in four reaction vessels according to an embodiment of the present invention.
Figure 44B:
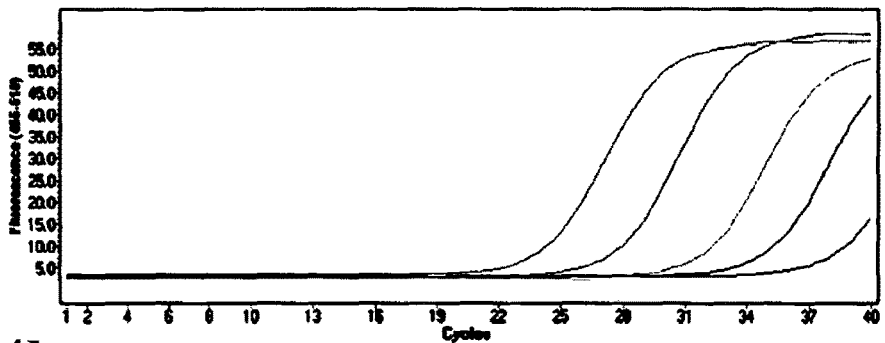
FIG. 44b shows a plot of fluorescence against cycle number for q-PCR analysis using an existing LC480 device.
Figure 45:
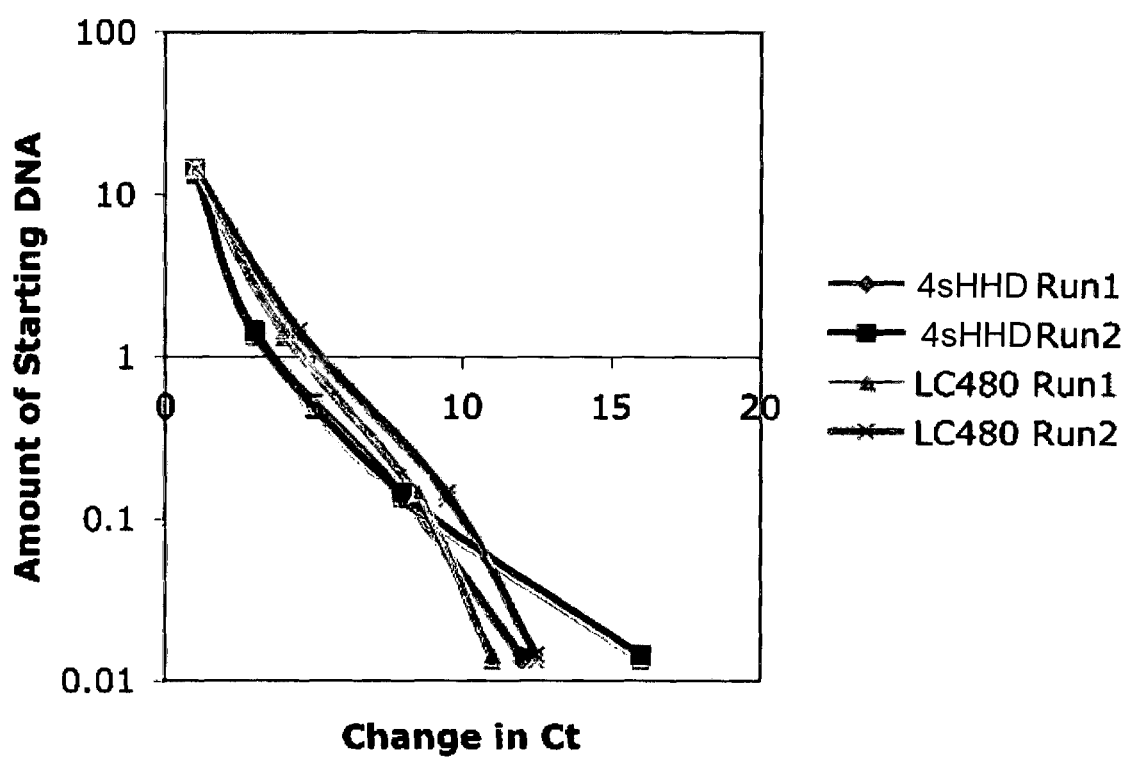
FIG. 45 shows a plot of the initial DNA volume against the cycle threshold for the runs shown in FIGS. 43a to 43b.

PCR was performed on both the 4sHHD and the LC480 and an example of the results given in FIG. 44a (for 4sHHD) and FIG. 44b (for LC480). In FIG. 30b, the bottom curve is for the negative control reaction. Results are given in table 5 and FIG. 45. Once the Ct for each Q-PCR reaction was determined the ΔCt was calculated. This is the difference in Ct between the Q-PCR with the highest amount of starting DNA and the Q-PCR for which ΔCt is being calculated. This is the number of extra cycles required before the reaction fluorescence first crosses the set threshold for the experiment.

TABLE 5

Relative Quantitative Analysis of DNA

| | Run 1: 010811 | | | | Run 2: 020811 | | | |
| | 4sHHD | | LightCycler 480 | | 4sHHD | | LightCycler 480 | |
| Dilution | Ct | ΔCt | Ct | ΔCt | Ct | ΔCt | Ct | ΔCt |
|---|---|---|---|---|---|---|---|---|
| Neat (14.5 ng) | 22 | — | 20.5 | — | 22 | — | 22 | — |
| 1:10 (1.45 ng) | 25 | 3 | 24.5 | 4 | 25 | 3 | 26.5 | 4.5 |
| 1:100 (0.0145 ng) | 30 | 8 | 29 | 8.5 | 30 | 8 | 31.5 | 9.5 |
| 1:1000 (0.00145 ng) | 34 | 12 | 31.5 | 11 | 38 | 16 | 34.5 | 12.5 |

The result from these experiments clearly shows that the amount of target DNA sequence in the Q-PCR reaction affects the point at which the threshold is crossed and that the 4sHHD can measure this effect. Significantly, the 4sHHD performed this task as well as the LC480.

Conclusion

The 4sHHD successfully performs Q-PCR to the same or similar sensitivity as the Roche LC480. These functions include both detection of amplified product for end-point evaluation methods and quantitative analysis of DNA target sequences from a complex mixture of nucleic acids.

Experiment 3

Use of Four-Sample Hand Held Device for Pathogen Detection

Detection assays for six specific human pathogens were carried out using the Four-sample Hand Held Device (4sHHD) of a preferred embodiment of the invention (as described above with reference to FIGS. 1, 2, and 13-23). These tests were performed by the respective national reference laboratories within the Institute for Environmental Science & Research Ltd New Zealand (ESR). The assays tested for E. coli STEC, Influenza, Adenovirus, Enterovirus, Norovirus GII and Astrovirus. Assays had been optimised for a range of commercially available Q-PCR reagents and two different laboratory-based instruments. For this series of experiments, tests were performed in parallel on the laboratory-base instrument and the 4sHHD with no additional optimisation of thermal cycle conditions or reagent chemistry undertaken to accommodate the 4sHHD.

Methods

A summary of reaction conditions, primers and commercial laboratory-based instruments used for each assay is given in Table 6.

TABLE 6

Pathogen tests and reaction conditions

| Target Pathogen | ESR Modified Reaction Conditions for Existing Devices‡ | Primer and Probe Sequences (5'->3')+<br>Forward primer<br>Reverse primer<br>Probe | Reference |
|---|---|---|---|
| *E.coli* STEC | Stratagene Mx3000P<br>1, 4, 7 | GGCCCCTGAATGCGGCTAAT (SEQ ID NO: 15)<br>CACCGGATGGCCAATCCAA (SEQ ID NO: 16)<br>Fam-CGCACACCCAAAGTAGTCGGTTCCG-Tamra (SEQ ID NO: 17) | Thomas et al (2012) Int. J. Food Micro. 153: 288 - 296 |
| Influenza A, Influenza B and H1N1pdm screening panel. | Stratagene Mx3000P<br>2, 5, 8 | See publication<br>See publication<br>See publication | Bo et al (2010) J. Clin. Microbiol. 49: 2614-2619 * |
| Adenovirus | RotorGene 3000<br>3, 6, 9 | GCCACGGTGGGGTTTCTAAACTT (SEQ ID NO: 3)<br>GCCCCAGTGGTCTTACATGCACATC (SEQ ID NO: 4)<br>Fam-TGCACCAGACCCGGGCTCAGGTACTCCGA-Tamra (SEQ ID NO: 5) | Heim et al (2003) J. Med. Virology 70: 228 - 239 |
| Enterovirus | RotorGene 3000<br>2, 6, 10 | GGCCCCTGAATGCGGCTAAT (SEQ ID NO: 6)<br>CACCGGATGGCCAATCCAA (SEQ ID NO: 7)<br>Fam-CGGACACCCAAAGTAGTCGGTTCCG-Tamra (SEQ ID NO: 8) | Donaldson et al (2002) Water Res. 36: 2505-2514 |
| Norovirus GII | RotorGene 3000<br>2, 6, 10 | CARGARBCNATGTTYAGRTGGATGAG (SEQ ID NO: 9)<br>TCGACGCCATCTTCATTCACA (SEQ ID NO: 10)<br>Fam-TGGGAGGGCGATCGCAATCT-Tamra (SEQ ID NO: 11) | Kageyama et al (2003) J. Clin. Microbiol. 41: 1548-1557 |
| Astrovirus | RotorGene 3000<br>2, 6, 10 | CCGAGTAGGATCGAGGGT (SEQ ID NO: 12)<br>GCTTCTGATTAAATCAATTTTAA (SEQ ID NO: 13)<br>Fam-CTTTCTGTCTCTGTTTAGATTATTTTAATCACC-Tamra (SEQ ID NO: 14) | Le Cann et al (2004) Res Microbiol 155: 11-15 |

+Letter code for degenerate primers: Y = C or T, R = A or G, B = not A, N = any.
* Center for Disease Control (USA) developed and World Health Organization recommended screening panel.
‡Reaction Condition Key
PCR assay type
1: PCR from DNA template
2: One-step RT-PCR. Start template is RNA which is transcribed to cDNA and PCR amplified in a single reaction.
3: RT-PCR. RNA transcription to cDNA and PCR amplification are performed in separate reactions
Nucleic Acid Extraction
4: DNeasy Blood & Tissue Kit
5: Zymo Viral RNA kit
6: Roche High-Pure Viral Nucleic Acid Kit
Q-PCR Reagents
7: Roche Lightcycler 480 Probes Master-Mix
8: Ambion AgPath One-Step Real Time PCR Mastermix
9: Invitrogen Platinum Q-PCR SuperMix-UDG
10: Invitrogen Superscript III Platinum One-Step Quantitative RT-PCR System Nucleic acid samples and cDNA was sythesised as per the manufacturer's instructions supplied with the relevant kit (Table 6). Thermal cycling conditions and final reaction volumes for each assay are summarized in Table 7.

TABLE 7

Reaction volumes and thermal cycling conditions for each assay

| Assay | Vol. (μl) | Cycle # | Denature | Annealing | Extension‡ |
|---|---|---|---|---|---|
| E.coli STEC | 20 | 45 | 95° C. 10 sec | 54° C. 15 sec | 72° C. 15 sec |
| Influenza | 25 | 40 | 95° C. 15 sec | 55° C. 30 sec | — |
| Adenovirus | 25 | 45 | 95° C. 15 sec | 55° C. 60 sec | — |
| Enterovirus | 25 | 45 | 95° C. 20 sec | 60° C. 60 sec | — |
| Norovirus GII | 25 | 45 | 95° C. 15 sec | 56° C. 60 sec | — |
| Astrovirus | 25 | 45 | 94° C. 15 sec | 55° C. 60 sec | — |

‡where no information is given, thermal program consists of a two step cycle.

For One-Step RT-PCR assays the 4sHHD and the commercial device were programmed to include a pre-incubation step prior to thermal cycling to permit conversion of RNA template to DNA by the reverse transcriptase enzyme. In this case, once samples were placed into the device the instrument held a specific temperature for 15 minutes. This was followed by raising the temperature to 95° C. to inactivate the reverse transcriptase enzyme and activate the thermal-stable polymerase for PCR. The operator was not required to interact with either PCR device once samples were loaded onto the instrument.

Results

Tests with plasmid control DNA, genomic DNA and viral RNA and DNA were performed in parallel on the reference system and the 4sHHD. All assays were functional on the 4sHHD and the results generated were favourably comparable to those produced from the commercial laboratory-based devices.

The results summarized in table 8 compare the limits-of-detection between the 4sHHD and the Rotorgene 3000 device for four gastrointestinal viruses (Astrovirus, Enterovirus, Norovirus GII and Adenovirus). Q-PCR was carried out using known copy number of target sequence at the start of the assay. To do this, plasmid DNA into which the target sequence had been cloned formed the template sample.

TABLE 8

Limit of detection for Gastrointestinal viruses. Comparison between the 4sHHD and the Rotorgene 3000.

| | Copy | Platform (Ct value) | | |
|---|---|---|---|---|
| Assay | Number | Rotorgene | 4sHHD | Difference* |
| Astrovirus | $10^3$ | 26.26 | 22.11 | 4.2 |
| | $10^4$ | 20.33 | 20.50 | −0.2 |
| | $10^5$ | 17.10 | 19.05 | −2.0 |
| | $10^6$ | 14.77 | 16.66 | −1.9 |
| | | | | Mean = 0.0 |
| Enterovirus | 1 | Neg | Neg | |
| | 10 | Neg | Neg | |
| | 100 | 34.91 | 44.36 | −9.5 |
| | $10^4$ | 28.31 | 33.98 | −5.7 |
| | | | | Mean = −7.6 |
| Norovirus GII | 1 | Neg | Neg | |
| | 10 | 35.72 | 36.63 | −0.9 |
| | 100 | 33.51 | 39.32 | −5.8 |
| | $10^4$ | 25.42 | 29.25 | −3.8 |
| | | | | Mean = −3.5 |
| Adenovirus | 1 | Neg | Neg | |
| | 10 | Neg | Neg | |
| | 100 | 42.43 | 43.64 | −1.2 |

TABLE 8-continued

Limit of detection for Gastrointestinal viruses. Comparison between the 4sHHD and the Rotorgene 3000.

| | Copy | Platform (Ct value) | | |
|---|---|---|---|---|
| Assay | Number | Rotorgene | 4sHHD | Difference* |
| | $10^4$ | 31.32 | 35.03 | −3.7 |
| | | | | Mean = −0.7 |

*Rotorgene Ct minus 4sHHD Ct

A similar experiment was carried out using defined amounts of E. coli STEC genomic DNA. Comparison was made between the performance of the 4sHHD and the Stratagene Mx3000P. Results are given in Table 9.

TABLE 9

Limit of Detection for E.coli STEC assay. Comparison between the Stratagene Mx3000 and 4sHHD

| DNA Amount | Platform (Ct value) | | |
|---|---|---|---|
| (femtograms) | Mx3000P | 4sHHD | Difference* |
| 2000 | 34.86 | 24.61 | 10.3 |
| 200 | 38.66 | 35.66 | 3.0 |
| 20 | 40.72 | 40.00 | 0.7 |
| 2 | Neg | Neg | |

*Mx3000P Ct minus 4sHHD Ct

The influenza screening panel was used in a second limit-of-detection comparison between the 4sHHD and the Stratagene Mx3000P and the results summarized in Table 10. Comparison was relative in that the exact copy number in the original sample was not known. In this case, samples from the same dilution were compared.

TABLE 10

Relative Limit of Detection for the Influenza Screening panel. Comparison between the Stratagene Mx3000P and the 4sHHD.

| | Dilution | Platform (Ct Value) | | |
|---|---|---|---|---|
| Assay | Factor | Mx3000P | 4sHHD‡ | Difference* |
| Influenza A | $10^1$ | 22.54 | 19.50 | 3.0 |
| | $10^2$ | 26.27 | 24.16 | 2.1 |
| | $10^3$ | 29.54 | 26.57 | 3.0 |
| | $10^4$ | 33.38 | 31.06 | 2.3 |
| | $10^5$ | 38.42 | 32.55 | 5.9 |
| | $10^6$ | 38.68 | 36.30 | 2.4 |
| | $10^7$ | Neg | 39.92 | |
| | $10^8$ | Neg | Neg | |
| | | | | Mean = 3.1 |
| Influenza B | $10^1$ | 21.13 | 17.12 | 4.0 |
| | $10^2$ | 21.10 | 19.35 | 1.8 |
| | $10^3$ | 24.95 | 22.38 | 2.6 |
| | $10^4$ | 28.07 | 25.79 | 2.3 |
| | $10^5$ | 35.48 | 29.15 | 6.3 |
| | $10^6$ | 35.01 | 30.55 | 4.5 |
| | $10^7$ | 38.43 | 34.99 | 3.4 |
| | $10^8$ | Neg | 35.49 | |
| | | | | Mean = 3.5 |
| 2009 Pandemic Influenza virus (specific) | $10^1$ | 13.94 | 16.68 | −2.7 |
| | $10^2$ | 17.48 | 18.42 | −0.9 |
| | $10^3$ | 21.55 | — | |
| | $10^4$ | 25.43 | 25.77 | −0.3 |
| | $10^5$ | 27.74 | 31.72 | −4.0 |
| | $10^6$ | 34.31 | 32.97 | 1.3 |
| | $10^7$ | 37.83 | 34.87 | 3.0 |

TABLE 10-continued

Relative Limit of Detection for the Influenza Screening panel.
Comparison between the Stratagene Mx3000P and the 4sHHD.

| Assay | Dilution Factor | Platform (Ct Value) | | Difference* |
|---|---|---|---|---|
| | | Mx3000P | 4sHHD‡ | |
| | $10^8$ | Neg | Neg | |
| | | | | Mean = −0.6 |

*Mx3000P Ct value minus 4sHHD Ct value.
‡Data collected across two runs

In a final set of experiments, clinical samples were tested on both the 4sHHD and the Stratagene Mx3000P or Rotorgene 3000. Clinical samples present significant challenges for testing. These challenges arise from the presence of heterogenious materials, possible reaction inhibitors, sample degradation, etc.

Three types of clinical sample were used in these experiments. These were:
- Human faecal specimens that were known to contain norovirus
- Faecal sample enriched in BHI broth overnight to detect *E. coli* STEC for use without DNA extraction
- Human nasopharyngeal specimens containing influenza virus.

The results presented in Table 10 were generated from human nasopharyngeal samples. These results showed that these clinical samples could be used with the 4sHHD and that the sensitivity of the 4sHHD was the same or better than the Stratagene Mx3000P.

Table 11 gives the results of clinical samples screened for norovirus and *E. coli* STEC in human faecal samples and enriched human faecal samples respectively. These results show clearly that the 4sHHD can be used with clinically relevant samples. One false negative was registered with the 4sHHD, however, this may indicate that some optimisation of the reaction chemistry is required. Normally, in real world application of Q-PCR technologies, optimisation of chemistry to specific platforms is always performed.

TABLE 11

Pathogen testing in clinical samples

| Pathogen | Sample ID | Established Method | | 4sHHD | |
|---|---|---|---|---|---|
| | | Ct | Result | Ct | Result |
| Norovirus GII | 676 | Neg | − | Neg | − |
| | 672 | 13.69 | + | 20.64 | + |
| | 656 | 22.93 | + | 30.37 | + |
| | 670 | 35.22 | + | Neg | − |
| *E.coli* STEC | ERL114012_1 | 23.88 | + | 27.54 | + |
| | ERL114012_2 | 23.84 | + | 33.97 | + |

Conclusion

All of the assays evaluated in this test could be seamlessly migrated to the 4sHHD without further optimisation. This included One-Step RT-PCR protocols in which a separate, non-PCR based enzymatic reaction was performed prior to thermal cycling, demonstrating further utility of the 4sHHD. In addition, the 4sHHD produced comparable results to the larger, laboratory-based instruments, Rotorgene 3000 and Stratagene Mx3000P. Finally, the 4sHHD can be used to detect pathogens in clinically relevant samples.

Experiment 4

Use of Four-Sample Hand Held Device as a Fluorometer to Estimate DNA Concentration Introduction The 4sHHD was investigated as a fluorometer to estimate DNA concentration. Knowing the concentration of nucleic acid is an important part of molecular biology practice. Whether it is undertaking PCR, cloning, sequencing or library construction, knowing the concentration of the nucleic acid sample under investigation is the first step in all of these procedures. Traditionally, nucleic acid concentration was determined by spectrophotometry. Nucleic acid maximally absorbs at 260 nm wavelength. By measuring the absorbance of a solution of nucleic acid at 260 nm, the amount of material present can be calculated using a constant value, dependent on the type of nucleic acid, of $X\mu l/\mu l$ absorbs at 1 OD unit at 260 nm. For DNA, this constant is 50 µg/µl.

Recently, alternative, more sensitive methods for determining nucleic acid concentration have been employed. Specifically, these methods are based on fluorometry. In this technique, an intercollating dye that changes its fluorescent characteristics when bound to nucleic acid is employed. The dye binds to the material present in the sample, the dye excited and emissions within the reporting spectrum measured. Concentration is determined by comparison to a standard curve generated from standards of known nucleic acid concentration.

In this experiment, the 4sHHD of a preferred embodiment of the invention (as described above with reference to FIGS. 1, 2, and 13 to 23) was used as a fluorometer and the importance of controlling sample temperature demonstrated. The 4sHHD further comprised the reaction vessel cover heaters of the preferred embodiment of the present invention (described above with reference to FIG. 38).

Methods

Instrumentation

The 4sHHD was used in this work. Spectrophotometer measurements were undertaken using the MBA 2000 (Perkin-Elmer, USA).

Sample Preparation

All DNA samples were diluted in PCR grade water (Roche Cat no. 03 315 843 001). Standards were generated using the DNA molecular weight marker XIV (Roche Cat no. 11 721 933001) supplied at a concentration of 0.25 µg/µl. For fluorometric measurements, 10 µl of sample or standard was added to 10 µl of SYBR Green I Master Mix (Roche Cat no. 04 707 516001). For spectrophotometric measurements, the DNA standard or sample was added directly to the measuring cuvette and the absorbance measured.

Program to Measure Fluorescence on 4sHHD

To measure fluorescence the 4sHHD was programmed to equilibrate the sample at a set temperature for 30 seconds and then to perform 4 cycles of holding at the measurement temperature for 10 seconds, collecting fluorescence data for 15 seconds and holding at the set temperature for a further 15 seconds. This ensured four measurements at each of the temperatures tested for this experiment.

Results

A serial dilution of molecular weight marker XIV (XIV) was made to construct a standard curve. To do this, 20 µl of XIV was mixed with 180 µl of nuclease-free water and mixed well. This gave the first standard at a concentration of approximately 25 ng/µl. For each subsequent dilution, 100 µl of the standard was mixed with 100 µl of water. In this way, a two-fold decrease in DNA concentration was achieved. Thirteen DNA standards and one water control were generated. A 1:10 dilution of a DNA sample of unknown concentration was also made.

The $OD_{260}$ of each standard and the unknown DNA sample were measured using standard spectrophotometry. $OD_{260}$ measurements and the calculated DNA concentration for each sample are given in table 12. DNA concentration was calculated using the formula:

$$\text{DNA } (\mu g/\mu l) = OD_{260} \times 50 \ \mu g/\mu l \text{ DNA at 1 } OD_{260} \text{ absorbance unit}$$

TABLE 12

$OD_{260}$ measurements and DNA concentration

| Sample or Standard | $OD_{260}$ | $OD_{260}$ less $OD_{260}$ of Blank | Calculated DNA concentration ($\mu g/\mu l$) |
|---|---|---|---|
| 1 | 0.551 | 0.579 | 28.95 |
| 2 | 0.263 | 0.291 | 14.55 |
| 3 | 0.124 | 0.152 | 7.6 |
| 4 | 0.054 | 0.084 | 4.1 |
| 5 | 0.024 | 0.052 | 2.6 |
| 6 | 0 | 0.028 | 1.4 |
| 7 | −0.011 | −0.017 | — |
| 8 | −0.007 | −0.021 | — |
| 9 | −0.020 | −0.008 | — |
| 10 | −0.018 | −0.012 | — |
| 11 | −0.020 | −0.008 | — |
| 12 | −0.017 | −0.011 | — |
| 13 | −0.020 | −0.008 | — |
| 14 (water blank) | −0.028 | — | — |
| 1:10 dilution sample | 1.203 | 1.231 | 61.55 |

Ten microlitres of the diluted sample and each standard was added to a white PCR tube (modified from Roche Multiwell plate and sealing foils Cat no. 04 729 692 001) along with 10 µl of SYBR Green Master Mix 1 and the tubes sealed. Four tubes were placed in the 4sHHD and the fluorescence measured four times at each of the following temperatures: 22° C., 4° C., 60° C. and 95° C. This was repeated until all standard and sample tubes had been processed. Results are given in Table 13 and FIG. 46.

Figure 46:
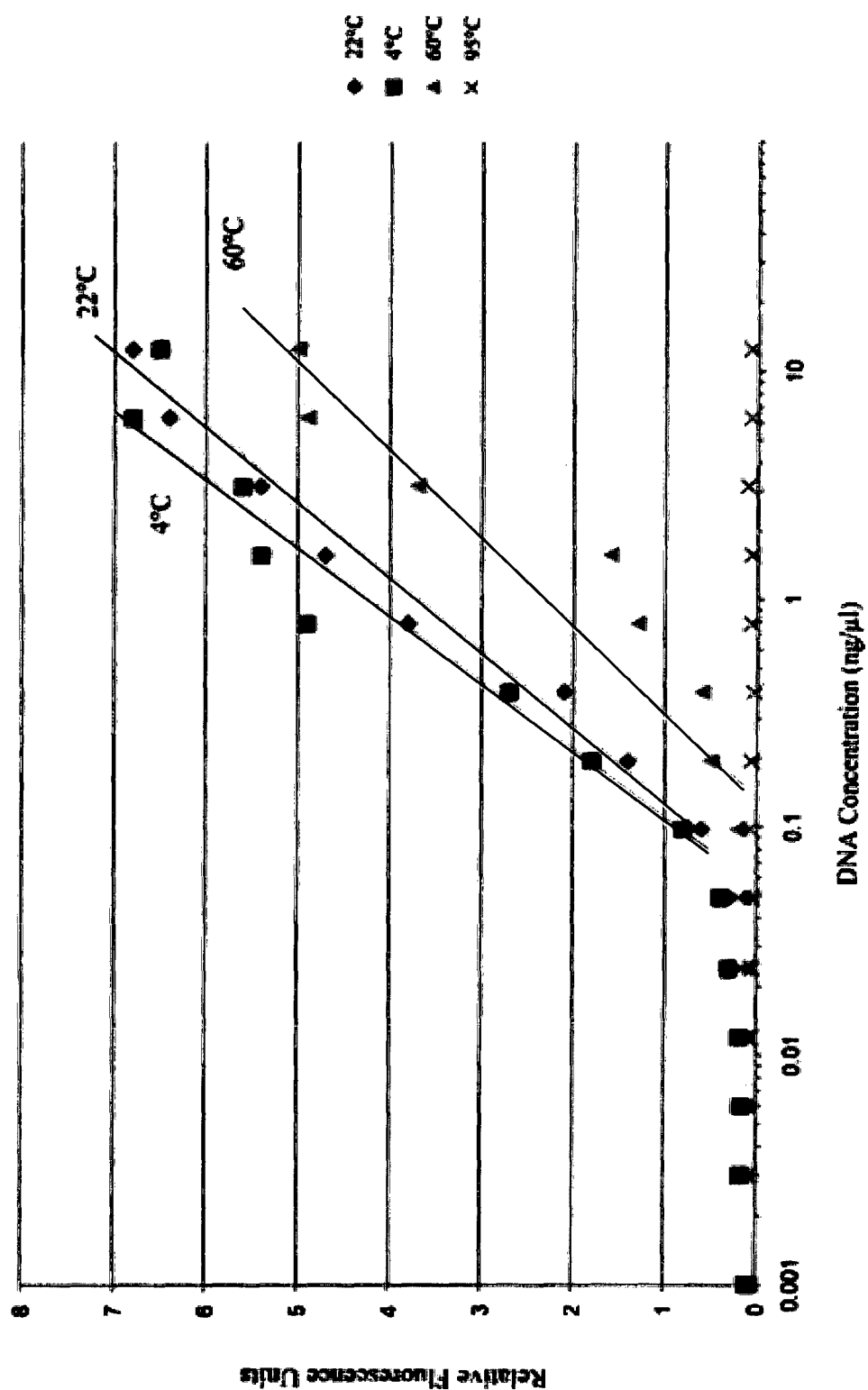
FIG. 46 shows a plot of the relative fluorescence in response to the DNA concentration for standards using a device for detecting molecule(s) in four reaction vessels according to an embodiment of the present invention.

FIG. 46 shows the relative fluorescence in response to the DNA concentration for standards as measured by the 4sHHD.

TABLE 13

Relative fluorescence reading for unknown sample generated using the 4sHHD

|  | 22° C. | 4° C. | 6° C. | 95° C. |
|---|---|---|---|---|
| 1:10 dilution Sample | 2.5 | 3.2 | 1.04 | 0.08 |
| Estimated Concentration from Standard Curve | 0.4 ng/µl | 0.5 ng/µl | 0.35 ng/µl | 0 ng/µl |
| Concentration of original sample (x10) | 4 ng/µl | 5 ng/µl | 3.5 ng/µl | 0 ng/µl |

Conclusion

The 4sHHD successfully measured changes in DNA concentration demonstrating its function as a fluorometer. The precision of specific fluorophore detection was clearly shown by the loss of signal once the DNA was denatured at 95° C. Under these conditions the intercollating dye, SYBR Green, cannot undergo the correct chemical change to emit light of the reporting wavelength. Fluorometry is known to be temperature sensitive as a result of the changing confirmation of DNA at different temperatures. Measurements from the 4sHHD showed this known effect. The usefulness of the 4sHHD to determine DNA concentration of a sample of unknown concentration was also demonstrated, through the fluorometric and spectrophotometric results did not align. It is likely that the spectrophotometer was detecting other molecules present in the sample as a result of the DNA purification process where as fluorometry only measures the nucleic acid in the sample.

SUMMARY OF SEQUENCES

| SEQ ID NO | Sequence | Type | Reference |
|---|---|---|---|
| 1 | Polynucleotide | Artificial, primer | eGFP-Short Forward |
| 2 | Polynucleotide | Artificial, primer | eGFP-Short Reverse |
| 3 | Polynucleotide | Artificial, primer | Adenovirus primer 1 |
| 4 | Polynucleotide | Artificial, primer | Adenovirus primer 2 |
| 5 | Polynucleotide | Artificial, primer | Adenovirus primer 3 |
| 6 | Polynucleotide | Artificial, primer | Enterovirus primer 1 |
| 7 | Polynucleotide | Artificial, primer | Enterovirus primer 2 |
| 8 | Polynucleotide | Artificial, primer | Enterovirus primer 3 |
| 9 | Polynucleotide | Artificial, primer | Norovirus GII primer 1 |
| 10 | Polynucleotide | Artificial, primer | Norovirus GII primer 2 |
| 11 | Polynucleotide | Artificial, primer | Norovirus GII primer 3 |
| 12 | Polynucleotide | Artificial, primer | Astrovirus primer 1 |
| 13 | Polynucleotide | Artificial, primer | Astrovirus primer 2 |
| 14 | Polynucleotide | Artificial, primer | Astrovirus primer 3 |

At least preferred embodiments of the present invention provide a device that is hand holdable and relatively compact. Due to the device's portability, compactness and low power consumption, the device is readily suitable for use in the field. The device provides real-time detection and analysis of molecule(s) in one or more reaction vessels.

Preferred embodiments of the invention have been described by way of example only and modifications may be made thereto without departing from the scope of the invention.

By way of example, the device according to embodiments of the present invention may further include a positioning means (for example a global position system (GPS) module) whereby the controller can be configured to automatically record the current position of the apparatus along with the results of each test. This may be particularly useful where the apparatus is used in the field for environmental testing, for example, so that the source location of a sample can be reliably and easily identified.

By way of further example, besides a test tube reaction vessel, aspects of the device (such as the optical system and/or lens heaters for example) may be configured to be used with other suitable reaction vessels such as a microscope slide or chip for example.

By way of further example, the device according to embodiments of the present invention may further include a transmitter for short- or long-distance wireless communication with a local or remote computing device by way of any suitable means, which may include a Bluetooth communication module for short-range communication with a nearby computing device, or a GSM (Global System for Mobile communication) module for communication with a remote computing device using a mobile telephone network, for example. Alternatively or additionally, the device may have a wired communication arrangement to enable communication and/or transfer of data with a nearby computing device. The computing device could be any suitable type of device, such as a PDA or laptop computer for example.

Alternatively, or additionally, the device according to embodiments of the present invention may be fully self-contained, including a processor programmed or configured to perform thermal cycling or thermal control and/or detection or analysis, and may further include an inbuilt display unit to enable an operator to review results of any detection or analysis performed with the device. The inbuilt display may be a touchscreen display for example. Alternatively, the device may be in communication with a processor programmed or configured to perform thermal cycling or thermal control and/or detection or analysis.

The device according to embodiments of the present invention could be further reduced in size from the sizes shown and described above, by modifying the shape and size of the reaction vessel and housing. Alternatively or additionally, the device could be reduced in size through reducing the size of the battery pack as energy requirements reduce, through reaction vessel changes or improvements in battery technology.

By way of further example, the device according to embodiments of the present invention may comprise suitable memory storage for use where wireless communication is unavailable.

The described components are one example only. Alternative components can be used in embodiments of the invention without affecting the functionality of or departing from the scope of the present invention.

Other modifications include those described in the Summary of the Invention section.

What is claimed is:

1. A device for detecting molecule(s), the device comprising a sample chamber adapted to receive and contact a reaction vessel, the sample chamber comprising:
 a vessel receptacle thermally coupled to a heat exchange device, the vessel receptacle being shaped to receive and substantially encompass the reaction vessel, and having a relatively high thermal conductivity and low thermal mass;
 a housing substantially enclosing the vessel receptacle and having an aperture at or substantially adjacent an open end of the vessel receptacle to permit insertion of the reaction vessel in the vessel receptacle;
 wherein the vessel receptacle is substantially insulated from the housing;
 wherein the heat exchange device comprises a thermoelectric cooling device positioned to be spaced from the sample chamber of a reaction vessel received on the vessel receptacle, wherein the thermoelectric cooling device has a first side that is in thermal communication with the vessel receptacle and a second side that is in thermal communication with a heat sink, wherein the heat sink is configured as a thermal reservoir that is maintained at a substantially constant temperature or within a substantially constant temperature range; and
 wherein the device further comprises:
  a controller associated with the heat exchange device and configured to control a temperature profile of the sample chamber to perform a reaction;
 an excitation assembly for inducing a reaction light in a reaction mixture in the reaction vessel; and
 a detector for optically detecting the reaction light.

2. The device for detecting molecule(s) of claim 1, wherein the heat sink is maintained at a substantially constant temperature or within a substantially constant temperature range above ambient temperature.

3. The device for detecting molecule(s) of claim 2, wherein the heat sink is maintained within a temperature range of 30-40° C.

4. The device for detecting molecule(s) of claim 1, wherein the thermoelectric cooling device is adapted to vary the temperature of the vessel receptacle by transferring heat between the heat sink and the vessel receptacle.

5. The device for detecting molecule(s) of claim 1, wherein the thermoelectric cooling device is a single-stage thermoelectric cooling device.

6. The device for detecting molecule(s) of claim 5, comprising a plurality of single-stage thermoelectric cooling devices having a first side in thermal communication with the vessel receptacle and a second side in thermal communication with the heat sink.

7. The device for detecting molecule(s) of claim 1, wherein the vessel receptacle comprises a substantially conical body having a bore for receiving the reaction vessel, and a substantially planar base that is thermally coupled with the heat exchange device, wherein the conical body diverges from the planar base towards the open end.

8. The device for detecting molecule(s) of claim 1, wherein the vessel receptacle comprises copper, silver, or aluminium, or a combination thereof.

9. The device for detecting molecule(s) of claim 1, wherein thermal conductivity of the vessel receptacle is higher than 200 $Wm^{-1}K^{-1}$.

10. The device for detecting molecule(s) of claim 1, wherein the vessel receptacle has a specific heat capacity of up to about 1.0 $Jg^{-1}K^{-1}$ at 25° C.

11. The device for detecting molecule(s) of claim 1, wherein the vessel receptacle is configured to receive a plurality of reaction vessels.

12. The device for detecting molecule(s) of claim 1, wherein the vessel receptacle is substantially insulated from the housing via an air gap.

13. The device for detecting molecule(s) of claim 1, wherein an insulative material is provided between the vessel receptacle and the housing.

14. The device for detecting molecule(s) of claim 1, wherein the controller comprises a microcontroller communicatively coupled to a controller of the heat exchange device and a temperature sensor at or adjacent the vessel receptacle, forming a closed-loop feedback control system.

15. The device for detecting molecule(s) of claim 1, wherein the excitation assembly and detector are each adapted to be optically coupled with a reaction vessel via the aperture in the housing, by way of respective excitation and detection optical paths.

16. The device for detecting molecule(s) of claim 15, wherein both or either of the excitation and detection optical paths are folded.

17. The device for detecting molecule(s) of claim 16, comprising a dichroic mirror that allows the reaction light emitted from within the reaction vessel substantially co-axial with the aperture to pass substantially without reflection or refraction.

18. The device for detecting molecule(s) of claim 1, wherein the device is suitable or configured for one or more of amplification of nucleic acids including analysis of polymerase chain reactions including quantitative polymerase chain reactions, protein analysis, ligand analysis, or fluorescence analysis of chemical reactions.

19. A portable device for quantitative polymerase chain reactions, the device comprising a sample chamber adapted to receive and contact a reaction vessel, the sample chamber comprising:

a vessel receptacle thermally coupled to a heat exchange device, the vessel receptacle being shaped to receive and substantially encompass a reaction vessel, wherein the heat exchange device comprises a thermoelectric cooling device positioned to be spaced from the sample chamber of a reaction vessel when received on the vessel receptacle, wherein the thermoelectric cooling device has a first side that is in thermal communication with the vessel receptacle and a second side that is in thermal communication with a heat sink, wherein the heat sink is configured as a thermal reservoir that is maintained at a substantially constant temperature or within a substantially constant temperature range; and wherein the portable device further comprises:
- a controller that is configured to vary the temperature of the vessel receptacle by transferring heat between the heat sink and the vessel receptacle to perform a reaction;
- an excitation assembly for inducing a reaction light in a reaction mixture in the reaction vessel; and
- a detector for optically detecting the reaction light.

\* \* \* \* \*

```
                           SEQUENCE LISTING

<160> NUMBER OF SEQ ID NOS: 17

<210> SEQ ID NO 1
<211> LENGTH: 20
<212> TYPE: DNA
<213> ORGANISM: Artificial sequence
<220> FEATURE:
<223> OTHER INFORMATION: Synthetic primer

<400> SEQUENCE: 1
ttcagccgct accccgacca                                                       20

<210> SEQ ID NO 2
<211> LENGTH: 20
<212> TYPE: DNA
<213> ORGANISM: AArtificial sequence
<220> FEATURE:
<223> OTHER INFORMATION: Synthetic primer

<400> SEQUENCE: 2
cggttcacca gggtgtcgcc                                                       20

<210> SEQ ID NO 3
<211> LENGTH: 23
<212> TYPE: DNA
<213> ORGANISM: Artificial sequence
<220> FEATURE:
<223> OTHER INFORMATION: Synthetic primer

<400> SEQUENCE: 3
gccacggtgg ggtttctaaa ctt                                                   23

<210> SEQ ID NO 4
<211> LENGTH: 25
<212> TYPE: DNA
<213> ORGANISM: Artificial sequence
<220> FEATURE:
<223> OTHER INFORMATION: Synthetic primer

<400> SEQUENCE: 4
gccccagtgg tcttacatgc acatc                                                 25

<210> SEQ ID NO 5
<211> LENGTH: 29
<212> TYPE: DNA
<213> ORGANISM: Artificial sequence
<220> FEATURE:
<223> OTHER INFORMATION: Synthetic primer
```

```
<400> SEQUENCE: 5
tgcaccagac ccgggctcag gtactccga                                    29

<210> SEQ ID NO 6
<211> LENGTH: 20
<212> TYPE: DNA
<213> ORGANISM: Artificial sequence
<220> FEATURE:
<223> OTHER INFORMATION: Synthetic primer

<400> SEQUENCE: 6
ggcccctgaa tgcggctaat                                              20

<210> SEQ ID NO 7
<211> LENGTH: 19
<212> TYPE: DNA
<213> ORGANISM: Artificial sequence
<220> FEATURE:
<223> OTHER INFORMATION: Synthetic primer

<400> SEQUENCE: 7
caccggatgg ccaatccaa                                               19

<210> SEQ ID NO 8
<211> LENGTH: 25
<212> TYPE: DNA
<213> ORGANISM: Artificial sequence
<220> FEATURE:
<223> OTHER INFORMATION: Synthetic primer

<400> SEQUENCE: 8
cggacaccca aagtagtcgg ttccg                                        25

<210> SEQ ID NO 9
<211> LENGTH: 26
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: R is A or G
<220> FEATURE:
<221> NAME/KEY: misc_feature
<222> LOCATION: (6)..(6)
<223> OTHER INFORMATION: R is A or G
<220> FEATURE:
<221> NAME/KEY: misc_feature
<222> LOCATION: (7)..(7)
<223> OTHER INFORMATION: B is C, G or T
<220> FEATURE:
<221> NAME/KEY: misc_feature
<222> LOCATION: (9)..(9)
<223> OTHER INFORMATION: N is A, C, G or T
<220> FEATURE:
<221> NAME/KEY: misc_feature
<222> LOCATION: (15)..(15)
<223> OTHER INFORMATION: Y is C or T
<220> FEATURE:
<221> NAME/KEY: misc_feature
<222> LOCATION: (18)..(18)
<223> OTHER INFORMATION: R is A or G

<400> SEQUENCE: 9
cargarbcna tgttyagrtg gatgag                                       26

<210> SEQ ID NO 10
```

```
<211> LENGTH: 21
<212> TYPE: DNA
<213> ORGANISM: Artificial sequence
<220> FEATURE:
<223> OTHER INFORMATION: Synthetic primer

<400> SEQUENCE: 10
tcgacgccat cttcattcac a                                               21

<210> SEQ ID NO 11
<211> LENGTH: 20
<212> TYPE: DNA
<213> ORGANISM: Artificial sequence
<220> FEATURE:
<223> OTHER INFORMATION: Synthetic primer

<400> SEQUENCE: 11
tgggagggcg atcgcaatct                                                 20

<210> SEQ ID NO 12
<211> LENGTH: 18
<212> TYPE: DNA
<213> ORGANISM: Artificial sequence
<220> FEATURE:
<223> OTHER INFORMATION: Synthetic primer

<400> SEQUENCE: 12
ccgagtagga tcgagggt                                                   18

<210> SEQ ID NO 13
<211> LENGTH: 23
<212> TYPE: DNA
<213> ORGANISM: Artificial sequence
<220> FEATURE:
<223> OTHER INFORMATION: Synthetic primer

<400> SEQUENCE: 13
gcttctgatt aaatcaattt taa                                             23

<210> SEQ ID NO 14
<211> LENGTH: 34
<212> TYPE: DNA
<213> ORGANISM: Artificial sequence
<220> FEATURE:
<223> OTHER INFORMATION: Synthetic primer

<400> SEQUENCE: 14
cttttctgtc tctgtttaga ttattttaat cacc                                 34

<210> SEQ ID NO 15
<211> LENGTH: 20
<212> TYPE: DNA
<213> ORGANISM: Artificial sequence
<220> FEATURE:
<223> OTHER INFORMATION: Synthetic primer

<400> SEQUENCE: 15
ggcccctgaa tgcggctaat                                                 20

<210> SEQ ID NO 16
<211> LENGTH: 19
<212> TYPE: DNA
<213> ORGANISM: Artificial sequence
<220> FEATURE:
<223> OTHER INFORMATION: Synthetic primer

<400> SEQUENCE: 16
```
caccggatgg ccaatccaa                                              19

<210> SEQ ID NO 17
<211> LENGTH: 25
<212> TYPE: DNA
<213> ORGANISM: Artificial sequence
<220> FEATURE:
<223> OTHER INFORMATION: Synthetic primer

<400> SEQUENCE: 17
cgcacaccca aagtagtcgg ttccg                                       25